United States Patent
Zhu et al.

(10) Patent No.: US 8,673,900 B2
(45) Date of Patent: *Mar. 18, 2014

(54) GAMMA SECRETASE MODULATORS

(75) Inventors: Zhaoning Zhu, Plainsboro, NJ (US); William J. Greenlee, Teaneck, NJ (US); Xianhai Huang, Warren, NJ (US); Jun Qin, Somerset, NJ (US); Xiaoxiang Liu, River Vale, NJ (US); Hongmei Li, Warren, NJ (US); Wei Zhou, Kenilworth, NJ (US); Anandan Palani, Bridgewater, NJ (US); Xiaohong Zhu, Edison, NJ (US); Monica L. Vicarel, Basking Ridge, NJ (US); Mihirbaran Mandal, Scotch Plains, NJ (US); Zhong-Yue Sun, Parlin, NJ (US); Chad E. Bennett, Metuchen, NJ (US); Troy Michael McCracken, Garwood, NJ (US); Gioconda V. Gallo, Summit, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 202 days.

This patent is subject to a terminal disclaimer.

(21) Appl. No.: 13/128,493

(22) PCT Filed: Nov. 12, 2009

(86) PCT No.: PCT/US2009/064190
§ 371 (c)(1),
(2), (4) Date: Aug. 16, 2011

(87) PCT Pub. No.: WO2010/056849
PCT Pub. Date: May 20, 2010

(65) Prior Publication Data
US 2011/0294756 A1    Dec. 1, 2011

Related U.S. Application Data

(60) Provisional application No. 61/114,233, filed on Nov. 13, 2008.

(51) Int. Cl.
*C07D 471/04* (2006.01)
*C07D 498/04* (2006.01)
*A61K 31/5395* (2006.01)

(52) U.S. Cl.
USPC .......................................... 514/229.2; 544/66

(58) Field of Classification Search
USPC ........................................ 544/66; 514/229.2
See application file for complete search history.

(56) References Cited

U.S. PATENT DOCUMENTS

| 8,357,682 B2 | 1/2013 | Zhu et al. |
| 2005/0042284 A1 | 2/2005 | Hobden et al. |
| 2006/0004013 A1 | 1/2006 | Kimura et al. |
| 2007/0117798 A1 | 5/2007 | Kimura et al. |
| 2007/0117839 A1 | 5/2007 | Kimura et al. |

FOREIGN PATENT DOCUMENTS

| WO | 204/071431 A2 | 8/2004 |
| WO | 2004110350 A2 | 12/2004 |
| WO | 2005110422 A2 | 11/2005 |
| WO | 2006001877 A2 | 1/2006 |
| WO | 2006045554 A1 | 5/2006 |
| WO | 2007060821 A1 | 5/2007 |
| WO | 2008137139 A1 | 11/2008 |
| WO | 2008153793 A1 | 12/2008 |

*Primary Examiner* — Kahsay Habte
(74) *Attorney, Agent, or Firm* — Susan L. Hess; Raynard Yuro; John C. Todaro

(57) ABSTRACT

In many embodiments, the present invention provides novel heterocyclic compounds which are modulators of gamma secretase, methods of preparing such compounds, pharmaceutical compositions containing one or more such compounds, methods of preparing pharmaceutical formulations comprising one or more such compounds, and methods of treatment, prevention, inhibition, or amelioration of one or more disease associated with the central nervous system using such compounds or pharmaceutical compositions.

2 Claims, No Drawings

GAMMA SECRETASE MODULATORS

CROSS REFERENCE TO RELATED APPLICATION

This application is entered into national stage examination under 37 U.S.C. 371 and stems from international patent application No. PCT/US2009/064190 filed on Nov. 12, 2009, which claims priority to application No. 61/114,233 filed Nov. 13, 2008.

FIELD OF THE INVENTION

The present invention relates to certain heterocyclic compounds useful as gamma secretase modulators (including inhibitors, antagonists and the like), pharmaceutical compositions containing the compounds, and methods of treatment using the compounds and compositions to treat various diseases including central nervous system disorders such as, for example, neurodegenerative diseases such as Alzheimer's disease and other diseases relating to the deposition of amyloid protein. They are especially useful for reducing Amyloid beta (hereinafter referred to as A$\beta$) production which is effective in the treatment of diseases caused by A$\beta$ such as, for example, Alzheimers and Down Syndrome.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

A$\beta$ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22, suggest a molecular basis for reversible memory loss.

Nitsch R M, and 16 others. *Antibodies against $\beta$-amyloid slow cognitive decline in Alzheimer's disease*, Neuron, May 22, 2003, 38(4), p. 547-554) suggest that the main components of A$\beta$ protein are A$\beta$40 consisting of 40 amino acids and A$\beta$42 having two additional amino acids at the C-terminal. The A$\beta$40 and A$\beta$42 tend to aggregate (for example, see Jarrell J T et al, *The carboxy terminus of the $\beta$ amyloid protein is critical for the seeding of amyloid formation: implications for the pathogenesis of Alzheimer's disease*, Biochemistry, May 11, 1993, 32(18), p. 4693-4697) and constitute main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer disease and Down syndrome*, Proceeding National Academy of Science USA, June 1985, 82(12), p. 4245-4249.).

Furthermore, it is known that mutations of APP and presenelin genes, which is observed in familial Alzheimer's disease, increase production of A$\beta$40 and A$\beta$42 (for example, see Gouras G K, et al, *Intraneuronal A$\beta$142 accumulation in human brain*, American Journal of Pathology, January 2000, 156(1), p. 15-20. Also, see Scheuner D, et at, Nature Medicine, August 1996, 2(8), p. 864-870; and Forman M S, et al, *Differential effects of the Swedish mutant amyloid precursor protein on $\beta$-amyloid accumulation and secretion in neurons and nonneuronal cells*, Journal of Biological Chemistry, Dec. 19, 1997, 272(51), p. 32247-32253.). Therefore, compounds which reduce production of A$\beta$40 and A$\beta$42 are expected as an agent for controlling progress of Alzheimer's disease or for preventing the disease.

These A$\beta$s are produced when APP is cleaved by beta secretase and subsequently clipped by gamma secretase. In consideration of this, creation of inhibitors of $\gamma$ secretase and $\beta$ secretase has been attempted for the purpose of reducing production of A$\beta$s. Many of these secretase inhibitors already known are peptides or peptidomimetics such as L-685,458. L-685,458, an aspartyl protease transition stale mimic, is a potent inhibitor of amyloid $\beta$-protein precursor $\gamma$-secretase activity, Biochemistry, Aug. 1, 2000, 39(30), p. 8698-8704).

Also of interest in connection with the present invention are: US 2007/0117798 (Eisai, published May 24, 2007); US 2007/0117839 (Eisai, published May 24, 2007); US 2006/0004013 (Eisai, published Jan. 5, 2006); WO 2005/110422 (Boehringer Ingelheim, published Nov. 24, 2005); WO 2006/045554 (Cellzone AG, published May 4, 2006); WO 2004/110350 (Neurogenetics, published Dec. 23, 2004); WO 2004/071431 (Myriad Genetics, published Aug. 26, 2004); US 2005/0042284 (Myriad Genetics, published Feb. 23, 2005) and WO 2006/001877 (Myriad Genetics, published Jan. 5, 2006).

There is a need for new compounds, formulations, treatments and therapies to treat diseases and disorders associated with A$\beta$. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as gamma secretase modulators (including inhibitors, antagonists and the like), methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the A$\beta$ using such compounds or pharmaceutical compositions.

As used herein, Group A represents compounds Q11, R4, T2, U2, W3, X2, Y3, Z2, Aa2, Ab2, Ac6, Af3, Ag4, Ah2, Ai2, Aj4, Ak2, Al2, Am3, Am4, An4, Ao5, Ap15, Aq7, Ar3, 201-203, 206-215, 220-222, 226-227, 229, 231, 233, and 245-394, identified below.

As used herein, Group B represents compounds 201-203, 206-215, 220-222, 226-227, 229, 231, 233, and 253-394, identified below.

The compounds of this invention (Groups A and B) can be useful as gamma secretase modulators and can be useful in the treatment and prevention of diseases such as, for example, Alzheimers disease, mild cognitive impairment (MCI), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci. USA 95, 6448-53 (1998)), Olfactory function loss (Getchell, et. al. Neurobiology of Aging, 663-673, 24, 2003).

This invention provides compounds selected from the group consisting of: the compounds of Group A, or a pharmaceutically acceptable salt, ester, solvate or prodrug thereof.

This invention also provides compounds selected from the group consisting of the compounds of Group A, or a pharmaceutically acceptable salt, ester, or solvate or thereof.

This invention also provides compounds selected from the group consisting of the compounds of Group A.

This invention also provides compounds selected from the group consisting of the compounds of Group B, or a pharmaceutically acceptable salt, ester, solvate or prodrug thereof.

This invention provides compounds selected from the group consisting of the compounds of Group B, or a pharmaceutically acceptable salt, ester, or solvate thereof.

This invention provides compounds selected from the group consisting of the compounds of Group B.

The present invention further includes the compounds of the invention in all its isolated forms.

This invention also provides the compounds of Group A or B in pure and isolated form.

This invention also provides pharmaceutical compositions comprising an effective amount of one or more (e.g., one) compounds of Group A, or a pharmaceutically acceptable salt, ester or solvate thereof, and a pharmaceutically acceptable carrier.

This invention also provides pharmaceutical compositions comprising an effective amount of one or more (e.g., one) compounds of Group B, or a pharmaceutically acceptable salt, ester or solvate thereof, and a pharmaceutically acceptable carrier.

This invention also provides pharmaceutical compositions comprising an effective amount of one or more (e.g., one) compounds of Group A, or a pharmaceutically acceptable salt, ester or solvate thereof, and an effective amount of one or more (e.g., one) other pharmaceutically active ingredients (e.g., drugs), and a pharmaceutically acceptable carrier.

This invention also provides pharmaceutical compositions comprising an effective amount of one or more (e.g., one) compounds of Group B, or a pharmaceutically acceptable salt, ester or solvate thereof, and an effective amount of one or more (e.g., one) other pharmaceutically active ingredients (e.g., drugs), and a pharmaceutically acceptable carrier.

The compounds of Formula A or B can be useful as gamma secretase modulators and can be useful in the treatment and prevention of diseases such as, for example, central nervous system disorders such as Alzheimers disease and Downs Syndrome.

Thus, this invention also provides methods for: (1) method for modulating (including inhibiting, antagonizing and the like) gamma-secretase; (2) treating one or more neurodegenerative diseases: (3) inhibiting the deposition of amyloid protein (e.g., amyloid beta protein) in, on or around neurological tissue (e.g., the brain); (4) Alzheimer's disease; and (5) treating Downs syndrome; wherein each method comprises administering an effective amount of one or more (e.g., one) compounds of Group A to a patient in need of such treatment.

Thus, this invention also provides methods for: (1) method for modulating (including inhibiting, antagonizing and the like) gamma-secretase; (2) treating one or more neurodegenerative diseases; (3) inhibiting the deposition of amyloid protein (e.g., amyloid beta protein) in, on or around neurological tissue (e.g., the brain); (4) Alzheimer's disease; and (5) treating Downs syndrome; wherein each method comprises administering an effective amount of one or more (e.g., one) compounds of formula B to a patient in need of such treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of Group A and the administration of an effective amount of one or more (e.g., one) other pharmaceutical active ingredients (e.g., drugs).

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of Group B and the administration of an effective amount of one or more (e.g., one) other pharmaceutical active ingredients (e.g., drugs).

This invention also provides methods for: (1) treating mild cognitive impairment; (2) treating glaucoma; (3) treating cerebral amyloid angiopathy; (4) treating stroke; (5) treating dementia; (6) treating microgliosis; (7) treating brain inflammation; and (8) treating olfactory function loss; wherein each method comprises administering an effective amount of one or more (e.g., one) compounds of Group AI to a patient in need of such treatment.

This invention also provides methods for: (1) treating mild cognitive impairment; (2) treating glaucoma; (3) treating cerebral amyloid angiopathy; (4) treating stroke; (5) treating dementia; (6) treating microgliosis; (7) treating brain inflammation; and (8) treating olfactory function loss; wherein each method comprises administering an effective amount of one or more (e.g., one) compounds of Group B to a patient in need of such treatment.

This invention also provides a kit comprising, in separate containers, in a single package, pharmaceutical compositions for use in combination, wherein one container comprises an effective amount of a compound of Group A in a pharmaceutically acceptable carrier, and another container (i.e., a second container) comprises an effective amount of another pharmaceutically active ingredient (as described below), the combined quantities of the compound of Group A and the other pharmaceutically active ingredient being effective to treat the diseases or conditions mentioned in any of the above methods.

This invention also provides a kit comprising, in separate containers, in a single package, pharmaceutical compositions for use in combination, wherein one container comprises an effective amount of a compound of Group B in a pharmaceutically acceptable carrier, and another container (i.e., a second container) comprises an effective amount of another pharmaceutically active ingredient (as described below), the combined quantities of the compound of Group BI and the other pharmaceutically active ingredient being effective to treat the diseases or conditions mentioned in any of the above methods.

DETAILED DESCRIPTION

Thus, one embodiment of this invention is directed to compounds of Group A.

Another embodiment of this invention is directed to compounds of Group B.

The compounds of this invention are useful for treating central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

Thus, for example, the compounds of this invention can be used to treat the following diseases or conditions: Alzheimers disease, mild cognitive impairment (MCI), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci. USA 95, 6448-53 (1998)), and Olfactory function loss (Getchell, et. al. Neurobiology of Aging, 663-673, 24, 2003).

Another embodiment of this invention is directed to compound Q11. Another embodiment of this invention is directed to compound R4. Another embodiment of this invention is directed to compound U2. Another embodiment of this invention is directed to compound W3. Another embodiment of this invention is directed to compound X2. Another embodiment of this invention is directed to compound Y3. Another embodiment of this invention is directed to compound Z2. Another embodiment of this invention is directed to compound Aa2. Another embodiment of this invention is directed to compound Ab2. Another embodiment of this invention is directed to compound Ac6. Another embodiment of this invention is directed to compound Af3. Another embodiment of this invention is directed to compound Ag4. Another embodiment of this invention is directed to compound Ah2. Another embodiment of this invention is directed to compound Ai2. Another embodiment of this invention is directed to compound Aj4. Another embodiment of this invention is directed to compound Ak2. Another embodiment of this invention is directed to compound Al2. Another embodiment of this invention is directed to compound Am3. Another embodiment of this invention is directed to compound Am4. Another embodiment of this invention is directed to compound Ao5. Another embodiment of this invention is directed to compound Ap15. Another embodiment of this invention is directed to compound Aq7. Another embodiment of this invention is directed to compound Ar3. Another embodiment of this invention is directed to compound 201. Another embodiment of this invention is directed to compound 202. Another embodiment of this invention is directed to compound 203. Another embodiment of this invention is directed to compound 206. Another embodiment of this invention is directed to compound 207. Another embodiment of this invention is directed to compound 208. Another embodiment of this invention is directed to compound 209. Another embodiment of this invention is directed to compound 210. Another embodiment of this invention is directed to compound 211. Another embodiment of this invention is directed to compound 212. Another embodiment of this invention is directed to compound 213. Another embodiment of this invention is directed to compound 214. Another embodiment of this invention is directed to compound 215. Another embodiment of this invention is directed to compound 220. Another embodiment of this invention is directed to compound 221. Another embodiment of this invention is directed to compound 222. Another embodiment of this invention is directed to compound 226. Another embodiment of this invention is directed to compound 227. Another embodiment of this invention is directed to compound 229. Another embodiment of this invention is directed to compound 231. Another embodiment of this invention is directed to compound 233. Another embodiment of this invention is directed to compound 245, Another embodiment of this invention is directed to compound 246. Another embodiment of this invention is directed to compound 247. Another embodiment of this invention is directed to compound 248. Another embodiment of this invention is directed to compound 249. Another embodiment of this invention is directed to compound 250. Another embodiment of this invention is directed to compound 251. Another embodiment of this invention is directed to compound 252. Another embodiment of this invention is directed to compound 253. Another embodiment of this invention is directed to compound 254. Another embodiment of this invention is directed to compound 255. Another embodiment of this invention is directed to compound 256. Another embodiment of this invention is directed to compound 257. Another embodiment of this invention is directed to compound 258. Another embodiment of this invention is directed to compound 259. Another embodiment of this invention is directed to compound 260. Another embodiment of this invention is directed to compound 261. Another embodiment of this invention is directed to compound 262. Another embodiment of this invention is directed to compound 263. Another embodiment of this invention is directed to compound 264. Another embodiment of this invention is directed to compound 265. Another embodiment of this invention is directed to compound 266. Another embodiment of this invention is directed to compound 267. Another embodiment of this invention is directed to compound 268. Another embodiment of this invention is directed to compound 269. Another embodiment of this invention is directed to compound 270. Another embodiment of this invention is directed to compound 271. Another embodiment of this invention is directed to compound 272. Another embodiment of this invention is directed to compound 273. Another embodiment of this invention is directed to compound 274. Another embodiment of this invention is directed to compound 275. Another embodiment of this invention is directed to compound 276. Another embodiment of this invention is directed to compound 277. Another embodiment of this invention is directed to compound 278. Another embodiment of this invention is directed to compound 279. Another embodiment of this invention is directed to compound 280. Another embodiment of this invention is directed to compound 281. Another embodiment of this invention is directed to compound 282. Another embodiment of this invention is directed to compound 283. Another embodiment of this invention is directed to compound 284. Another embodiment of this invention is directed to compound 285. Another embodiment of this invention is directed to compound 286. Another embodiment of this invention is directed to compound 287. Another embodiment of this invention is directed to compound 288. Another embodiment of this invention is directed to compound 289. Another embodiment of this invention is directed to compound 290. Another embodiment of this invention is directed to compound 291. Another embodiment of this invention is directed to compound 292. Another embodiment of this invention is directed to compound 293. Another embodiment of this invention is directed to compound 294. Another embodiment of this invention is directed to compound 295. Another embodiment of this invention is directed to compound 296. Another embodiment of this invention is directed to compound 297. Another embodiment of this invention is directed to compound 298. Another embodiment of this invention is directed to compound 299. Another embodiment of this invention is directed to compound 300. Another embodiment of this invention is directed to compound 301. Another embodiment of this invention is directed to compound 302. Another embodiment of this invention is directed to compound 303. Another embodiment of this invention is directed to compound 304. Another embodiment of this invention is directed to compound 305. Another embodiment of this invention is directed to compound 306. Another embodiment of this invention is directed to compound 307. Another embodiment of this invention is directed to compound 308. Another embodiment of this invention is directed to compound 309. Another embodiment of this invention is directed to compound 310. Another embodiment of this invention is directed to compound 311. Another embodiment of this invention is directed to compound 312. Another embodiment of this invention is directed to compound 313. Another embodiment of this invention is directed to compound 314. Another embodiment of this invention is directed to compound 315. Another embodiment of this invention is directed to compound 316, Another embodiment of this invention is directed to compound 317. Another embodiment of this invention is directed to compound 318, Another embodiment of this invention is directed to compound 319. Another embodiment of this invention is directed to compound 320. Another embodiment of this invention is directed to compound 321. Another embodiment of this invention is directed to compound 322. Another embodiment of this invention is directed to compound 323. Another embodiment of this invention is directed to compound 324. Another embodiment of this invention is directed to compound 325. Another embodiment of this invention is directed to compound 326. Another embodiment of this invention is directed to compound 327. Another embodiment of this invention is directed to compound 328. Another embodiment of this invention is directed to compound 329. Another embodiment of this invention is directed to compound 330. Another embodiment of this invention is directed to compound 331. Another embodiment of this invention is directed to compound 332. Another embodiment of this invention is directed to compound 333. Another embodiment of this invention is directed to compound 334. Another embodiment of this invention is directed to compound 335. Another embodiment of this invention is directed to compound 336. Another embodiment of this invention is directed to compound 337. Another embodiment of this invention is directed to compound 338. Another embodiment of this invention is directed to compound 339. Another embodiment of this invention is directed to compound 340. Another embodiment of this invention is directed to compound 341. Another embodiment of this invention is directed to compound 342. Another embodiment of this invention is directed to compound 343. Another embodiment of this invention is directed to compound 344. Another embodiment of this invention is directed to compound 345. Another embodiment of this invention is directed to compound 346. Another embodiment of this invention is directed to compound 347. Another embodiment of this invention is directed to compound 348. Another embodiment of this invention is directed to compound 349. Another embodiment of this invention is directed to compound 350. Another embodiment of this invention is directed to compound 351. Another embodiment of this invention is directed to compound 352. Another embodiment of this invention is directed to compound 353. Another embodiment of this invention is directed to compound 354. Another embodiment of this invention is directed to compound 355. Another embodiment of this invention is directed to compound 356. Another embodiment of this invention is directed to compound 357. Another embodiment of this invention is directed to compound 358. Another embodiment of this invention is directed to compound 359. Another embodiment of this invention is directed to compound 360. Another embodiment of this invention is directed to compound 361. Another embodiment of this invention is directed to compound 362. Another embodiment of this invention is directed to compound 363. Another embodiment of this invention is directed to compound 364. Another embodiment of this invention is directed to compound 365. Another embodiment of this invention is directed to compound 366. Another embodiment of this invention is directed to compound 367. Another embodiment of this invention is directed to compound 368. Another embodiment of this invention is directed to compound 369. Another embodiment of this invention is directed to compound 370. Another embodiment of this invention is directed to compound 371. Another embodiment of this invention is directed to compound 372. Another embodiment of this invention is directed to compound 373. Another embodiment of this invention is directed to compound 374. Another embodiment of this invention is directed to compound 375. Another embodiment of this invention is directed to compound 376. Another embodiment of this invention is directed to compound 377. Another embodiment of this invention is directed to compound 378. Another embodiment of this invention is directed to compound 379. Another embodiment of this invention is directed to compound 380. Another embodiment of this invention is directed to compound 381. Another embodiment of this invention is directed to compound 382. Another embodiment of this invention is directed to compound 383. Another embodiment of this invention is directed to compound 384. Another embodiment of this invention is directed to compound 385. Another embodiment of this invention is directed to compound 386. Another embodiment of this invention is directed to compound 387. Another embodiment of this invention is directed to compound 388, Another embodiment of this invention is directed to compound 389. Another embodiment of this invention is directed to compound 390. Another embodiment of this invention is directed to compound 391. Another embodiment of this invention is directed to compound 392. Another embodiment of this invention is directed to compound 393. Another embodiment of this invention is directed to compound 394.

Another embodiment of this invention is directed to a pharmaceutically acceptable salt of compound Q11. Another embodiment of this invention is directed to a pharmaceutically acceptable salt of compound R4. Another embodiment of this invention is directed to a pharmaceutically acceptable salt of compound U2. Another embodiment of this invention is directed to a pharmaceutically acceptable salt of compound W3. Another embodiment of this invention is directed to a pharmaceutically acceptable salt of compound X2. Another embodiment of this invention is directed to a pharmaceutically acceptable salt of compound Y3. Another embodiment of this invention is directed to a pharmaceutically acceptable salt of compound Z2. Another embodiment of this invention is directed to a pharmaceutically acceptable salt of compound Aa2. Another embodiment of this invention is directed to a pharmaceutically acceptable salt of compound Ab2. Another embodiment of this invention is directed to a pharmaceutically acceptable salt of compound Ac6. Another embodiment of this invention is directed to a pharmaceutically acceptable salt of compound Af3. Another embodiment of this invention is directed to a pharmaceutically acceptable salt of compound Ag4. Another embodiment of this invention is directed to a pharmaceutically acceptable salt of compound Ah2. Another embodiment of this invention is directed to a pharmaceutically acceptable salt of compound Ai2. Another embodiment of this invention is directed to a pharmaceutically acceptable salt of compound Aj4. Another embodiment of this invention is directed to a pharmaceutically acceptable salt of compound Ak2. Another embodiment of this invention is directed to a pharmaceutically acceptable salt of compound Al2. Another embodiment of this invention is directed to a pharmaceutically acceptable salt of compound Am3. Another embodiment of this invention is directed to a pharmaceutically acceptable salt of compound Am4. Another embodiment of this invention is directed to a pharmaceutically acceptable salt of compound Ao5. Another embodiment of this invention is directed to a pharmaceutically acceptable salt of compound Ap15. Another embodiment of this invention is directed to a pharmaceutically acceptable salt of compound Aq7. Another embodiment of this invention is directed to a pharmaceutically acceptable salt of compound Ar3. Another embodiment of this invention is directed to a pharmaceutically acceptable salt of compound 201. Another embodiment of this invention is directed to a pharmaceutically acceptable salt of compound 202. Another embodiment of this invention is directed to a pharmaceutically acceptable salt of compound 203. Another embodiment of this invention is directed to a pharmaceutically acceptable salt of compound 206. Another embodiment of this invention is directed to a pharmaceutically acceptable salt of compound 207. Another embodiment of this invention is directed to a pharmaceutically acceptable salt of compound 208. Another embodiment of this invention is directed to a pharmaceutically acceptable salt of compound 209. Another embodiment of this invention is directed to a pharmaceutically acceptable salt of compound 210. Another embodiment of this invention is directed to a pharmaceutically acceptable salt of compound 211. Another embodiment of this invention is directed to a pharmaceutically acceptable salt of compound 212. Another embodiment of this invention is directed to a pharmaceutically acceptable salt of compound 213. Another embodiment of this invention is directed to a pharmaceutically acceptable salt of compound 214. Another embodiment of this invention is directed to a pharmaceutically acceptable salt of compound 215. Another embodiment of this invention is directed to a pharmaceutically acceptable salt of compound 220. Another embodiment of this invention is directed to a pharmaceutically acceptable salt of compound 221. Another embodiment of this invention is directed to a pharmaceutically acceptable salt of compound 222. Another embodiment of this invention is directed to a pharmaceutically acceptable salt of compound 226. Another embodiment of this invention is directed to a pharmaceutically acceptable salt of compound 227. Another embodiment of this invention is directed to a pharmaceutically acceptable salt of compound 229. Another embodiment of this invention is directed to a pharmaceutically acceptable salt of compound 231. Another embodiment of this invention is directed to a pharmaceutically acceptable salt of compound 233. Another embodiment of this invention is directed to a pharmaceutically acceptable salt of compound 245. Another embodiment of this invention is directed to a pharmaceutically acceptable salt of compound 246. Another embodiment of this invention is directed to a pharmaceutically acceptable salt of compound 247. Another embodiment of this invention is directed to a pharmaceutically acceptable salt of compound 248. Another embodiment of this invention is directed to a pharmaceutically acceptable salt of compound 249. Another embodiment of this invention is directed to a pharmaceutically acceptable salt of compound 250. Another embodiment of this invention is directed to a pharmaceutically acceptable salt of compound 251. Another embodiment of this invention is directed to a pharmaceutically acceptable salt of compound 252. Another embodiment of this invention is directed to a pharmaceutically acceptable salt of compound 253. Another embodiment of this invention is directed to a pharmaceutically acceptable salt of compound 254. Another embodiment of this invention is directed to a pharmaceutically acceptable salt of compound 255. Another embodiment of this invention is directed to a pharmaceutically acceptable salt of compound 256. Another embodiment of this invention is directed to a pharmaceutically acceptable salt of compound 257. Another embodiment of this invention is directed to a pharmaceutically acceptable salt of compound 258. Another embodiment of this invention is directed to a pharmaceutically acceptable salt of compound 259. Another embodiment of this invention is directed to a pharmaceutically acceptable salt of compound 260. Another of embodiment of this invention is directed to a pharmaceutically acceptable salt of compound 261. Another embodiment of this invention is directed to a pharmaceutically acceptable salt of compound 262. Another embodiment of this invention is directed to a pharmaceutically acceptable salt of compound 263. Another embodiment of this invention is directed to a pharmaceutically acceptable salt of compound 264. Another embodiment of this invention is directed to a pharmaceutically acceptable salt of compound 265. Another embodiment of this invention is directed to a pharmaceutically acceptable salt of compound 266. Another embodiment of this invention is directed to a pharmaceutically acceptable salt of compound 267. Another embodiment of this invention is directed to a pharmaceutically acceptable salt of compound 268. Another embodiment of this invention is directed to a pharmaceutically acceptable salt of compound 269. Another embodiment of this invention is directed to a pharmaceutically acceptable salt of compound 270. Another embodiment of this invention is directed to a pharmaceutically acceptable salt of compound 271. Another embodiment of this invention is directed to a pharmaceutically acceptable salt of compound 272. Another embodiment of this invention is directed to a pharmaceutically acceptable salt of compound 273. Another embodiment of this invention is directed to a pharmaceutically acceptable salt of compound 274. Another embodiment of this invention is directed to a pharmaceutically acceptable salt of compound 275. Another embodiment of this invention is directed to a pharmaceutically acceptable salt of compound 276. Another embodiment of this invention is directed to a pharmaceutically acceptable salt of compound 277. Another embodiment of this invention is directed to a pharmaceutically acceptable salt of compound 278. Another embodiment of this invention is directed to a pharmaceutically acceptable salt of compound 279. Another embodiment of this invention is directed to a pharmaceutically acceptable salt of compound 280. Another embodiment of this invention is directed to a pharmaceutically acceptable salt of compound 281. Another embodiment of this invention is directed to a pharmaceutically acceptable salt of compound 282. Another embodiment of this invention is directed to a pharmaceutically acceptable salt of compound 283. Another embodiment of this invention is directed to a pharmaceutically acceptable salt of compound 284. Another embodiment of this invention is directed to a pharmaceutically acceptable salt of compound 285. Another embodiment of this invention is directed to a pharmaceutically acceptable salt of compound 286. Another embodiment of this invention is directed to a pharmaceutically acceptable salt of compound 287. Another embodiment of this invention is directed to a pharmaceutically acceptable salt of compound 288. Another embodiment of this invention is directed to a pharmaceutically acceptable salt of compound 289. Another embodiment of this invention is directed to a pharmaceutically acceptable salt of compound 290. Another of embodiment of this invention is directed to a pharmaceutically acceptable salt of compound 291. Another embodiment of this invention is directed to a pharmaceutically acceptable salt of compound 292. Another embodiment of this invention is directed to a pharmaceutically acceptable salt of compound 293. Another embodiment of this invention is directed to a pharmaceutically acceptable salt of compound 294. Another embodiment of this invention is directed to a pharmaceutically acceptable salt of compound 295. Another embodiment of this invention is directed to a pharmaceutically acceptable salt of compound 296. Another embodiment of this invention is directed to a pharmaceutically acceptable salt of compound 297. Another embodiment of this invention is directed to a pharmaceutically acceptable salt of compound 298. Another embodiment of this invention is directed to a pharmaceutically acceptable salt of compound 299. Another embodiment of this invention is directed to a pharmaceutically acceptable salt of compound 300. Another of embodiment of this invention is directed to a pharmaceutically acceptable salt of compound 301. Another embodiment of this invention is directed to a pharmaceutically acceptable salt of compound 302. Another embodiment of this invention is directed to a pharmaceutically acceptable salt of compound 303. Another embodiment of this invention is directed to a pharmaceutically acceptable salt of compound 304. Another embodiment of this invention is directed to a pharmaceutically acceptable salt of compound 305. Another embodiment of this invention is directed to a pharmaceutically acceptable salt of compound 306. Another embodiment of this invention is directed to a pharmaceutically acceptable salt of compound 307. Another embodiment of this invention is directed to a pharmaceutically acceptable salt of compound 308. Another embodiment of this invention is directed to a pharmaceutically acceptable salt of compound 309. Another embodiment of this invention is directed to a pharmaceutically acceptable salt of compound 310. Another of embodiment of this invention is directed to a pharmaceutically acceptable salt of compound 311. Another embodiment of this invention is directed to a pharmaceutically acceptable salt of compound 312. Another embodiment of this invention is directed to a pharmaceutically acceptable salt of compound 313. Another embodiment of this invention is directed to a pharmaceutically acceptable salt of compound 314. Another embodiment of this invention is directed to a pharmaceutically acceptable salt of compound 315. Another embodiment of this invention is directed to a pharmaceutically acceptable salt of compound 316. Another embodiment of this invention is directed to a pharmaceutically acceptable salt of compound 317. Another embodiment of this invention is directed to a pharmaceutically acceptable salt of compound 318. Another embodiment of this invention is directed to a pharmaceutically acceptable salt of compound 319. Another embodiment of this invention is directed to a pharmaceutically acceptable salt of compound 320. Another of embodiment of this invention is directed to a pharmaceutically acceptable salt of compound 321. Another embodiment of this invention is directed to a pharmaceutically acceptable salt of compound 322. Another embodiment of this invention is directed to a pharmaceutically acceptable salt of compound 323. Another embodiment of this invention is directed to a pharmaceutically acceptable salt of compound 324. Another embodiment of this invention is directed to a pharmaceutically acceptable salt of compound 325. Another embodiment of this invention is directed to a pharmaceutically acceptable salt of compound 326. Another embodiment of this invention is directed to a pharmaceutically acceptable salt of compound 327. Another embodiment of this invention is directed to a pharmaceutically acceptable salt of compound 328. Another embodiment of this invention is directed to a pharmaceutically acceptable salt of compound 329. Another embodiment of this invention is directed to a pharmaceutically acceptable salt of compound 330. Another of embodiment of this invention is directed to a pharmaceutically acceptable salt of compound 331. Another embodiment of this invention is directed to a pharmaceutically acceptable salt of compound 332. Another embodiment of this invention is directed to a pharmaceutically acceptable salt of compound 333. Another embodiment of this invention is directed to a pharmaceutically acceptable salt of compound 334. Another embodiment of this invention is directed to a pharmaceutically acceptable salt of compound 335. Another embodiment of this invention is directed to a pharmaceutically acceptable salt of compound 336. Another embodiment of this invention is directed to a pharmaceutically acceptable salt of compound 337. Another embodiment of this invention is directed to a pharmaceutically acceptable salt of compound 338. Another embodiment of this invention is directed to a pharmaceutically acceptable salt of compound 339. Another embodiment of this invention is directed to a pharmaceutically acceptable salt of compound 340. Another of embodiment of this invention is directed to a pharmaceutically acceptable salt of compound 341, Another embodiment of this invention is directed to a pharmaceutically acceptable salt of compound 342. Another embodiment of this invention is directed to a pharmaceutically acceptable salt of compound 343. Another embodiment of this invention is directed to a pharmaceutically acceptable salt of compound 344. Another embodiment of this invention is directed to a pharmaceutically acceptable salt of compound 345. Another embodiment of this invention is directed to a pharmaceutically acceptable salt of compound 346. Another embodiment of this invention is directed to a pharmaceutically acceptable salt of compound 347. Another embodiment of this invention is directed to a pharmaceutically acceptable salt of compound 348. Another embodiment of this invention is directed to a pharmaceutically acceptable salt of compound 349. Another embodiment of this invention is directed to a pharmaceutically acceptable salt of compound 350. Another embodiment of this invention is directed to a pharmaceutically acceptable salt of compound 351. Another embodiment of this invention is directed to a pharmaceutically acceptable salt of compound 352. Another embodiment of this invention is directed to a pharmaceutically acceptable salt of compound 353. Another embodiment of this invention is directed to a pharmaceutically acceptable salt of compound 354. Another embodiment of this invention is directed to a pharmaceutically acceptable salt of compound 355. Another embodiment of this invention is directed to a pharmaceutically acceptable salt of compound 356. Another embodiment of this invention is directed to a pharmaceutically acceptable salt of compound 357. Another embodiment of this invention is directed to a pharmaceutically acceptable salt of compound 358. Another embodiment of this invention is directed to a pharmaceutically acceptable salt of compound 359. Another embodiment of this invention is directed to a pharmaceutically acceptable salt of compound 360. Another of embodiment of this invention is directed to a pharmaceutically acceptable salt of compound 361. Another embodiment of this invention is directed to a pharmaceutically acceptable salt of compound 362. Another embodiment of this invention is directed to a pharmaceutically acceptable salt of compound 363. Another embodiment of this invention is directed to a pharmaceutically acceptable salt of compound 364. Another embodiment of this invention is directed to a pharmaceutically acceptable salt of compound 365. Another embodiment of this invention is directed to a pharmaceutically acceptable salt of compound 366. Another embodiment of this invention is directed to a pharmaceutically acceptable salt of compound 367. Another embodiment of this invention is directed to a pharmaceutically acceptable salt of compound 368. Another embodiment of this invention is directed to a pharmaceutically acceptable salt of compound 369. Another embodiment of this invention is directed to a pharmaceutically acceptable salt of compound 370. Another embodiment of this invention is directed to a pharmaceutically acceptable salt of compound 371. Another embodiment of this invention is directed to a pharmaceutically acceptable salt of compound 372. Another embodiment of this invention is directed to a pharmaceutically acceptable salt of compound 373. Another embodiment of this invention is directed to a pharmaceutically acceptable salt of compound 374. Another embodiment of this invention is directed to a pharmaceutically acceptable salt of compound 375. Another embodiment of this invention is directed to a pharmaceutically acceptable salt of compound 376. Another embodiment of this invention is directed to a pharmaceutically acceptable salt of compound 377. Another embodiment of this invention is directed to a pharmaceutically acceptable salt of compound 378. Another embodiment of this invention is directed to a pharmaceutically acceptable salt of compound 379. Another embodiment of this invention is directed to a pharmaceutically acceptable salt of compound 380. Another embodiment of this invention is directed to a pharmaceutically acceptable salt of compound 381. Another embodiment of this invention is directed to a pharmaceutically acceptable salt of compound 382. Another embodiment of this invention is directed to a pharmaceutically acceptable salt of compound 383. Another embodiment of this invention is directed to a pharmaceutically acceptable salt of compound 384. Another embodiment of this invention is directed to a pharmaceutically acceptable salt of compound 385. Another embodiment of this invention is directed to a pharmaceutically acceptable salt of compound 386. Another embodiment of this invention is directed to a pharmaceutically acceptable salt of compound 387. Another embodiment of this invention is directed to a pharmaceutically acceptable salt of compound 388. Another embodiment of this invention is directed to a pharmaceutically acceptable salt of compound 389. Another embodiment of this invention is directed to a pharmaceutically acceptable salt of compound 390. Another of embodiment of this invention is directed to a pharmaceutically acceptable salt of compound 391. Another embodiment of this invention is directed to a pharmaceutically acceptable salt of compound 392. Another embodiment of this invention is directed to a pharmaceutically acceptable salt of compound 393. Another embodiment of this invention is directed to a pharmaceutically acceptable salt of compound 394.

Another embodiment of this invention is directed to a pharmaceutically acceptable ester of compound Q11. Another embodiment of this invention is directed to a pharmaceutically acceptable ester of compound R4. Another embodiment of this invention is directed to a pharmaceutically acceptable ester of compound U2. Another embodiment of this invention is directed to a pharmaceutically acceptable ester of compound W3. Another embodiment of this invention is directed to a pharmaceutically acceptable ester of compound X2. Another embodiment of this invention is directed to a pharmaceutically acceptable ester of compound Y3. Another embodiment of this invention is directed to a pharmaceutically acceptable ester of compound Z2. Another embodiment of this invention is directed to a pharmaceutically acceptable ester of compound Aa2. Another embodiment of this invention is directed to a pharmaceutically acceptable ester of compound Ab2. Another embodiment of this invention is directed to a pharmaceutically acceptable ester of compound Ac6. Another embodiment of this invention is directed to a pharmaceutically acceptable ester of compound Af3. Another embodiment of this invention is directed to a pharmaceutically acceptable ester of compound Ag4. Another embodiment of this invention is directed to a pharmaceutically acceptable ester of compound Ah2. Another embodiment of this invention is directed to a pharmaceutically acceptable ester of compound Ai2. Another embodiment of this invention is directed to a pharmaceutically acceptable ester of compound Aj4. Another embodiment of this invention is directed to a pharmaceutically acceptable ester of compound Ak2. Another embodiment of this invention is directed to a pharmaceutically acceptable ester of compound Al2. Another embodiment of this invention is directed to a pharmaceutically acceptable ester of compound Am3. Another embodiment of this invention is directed to a pharmaceutically acceptable ester of compound Am4. Another embodiment of this invention is directed to a pharmaceutically acceptable ester of compound Ao5. Another embodiment of this invention is directed to a pharmaceutically acceptable ester of compound Ap15. Another embodiment of this invention is directed to a pharmaceutically acceptable ester of compound Aq7. Another embodiment of this invention is directed to a pharmaceutically acceptable ester of compound Ar3. Another embodiment of this invention is directed to a pharmaceutically acceptable ester of compound 201. Another embodiment of this invention is directed to a pharmaceutically acceptable ester of compound 202. Another embodiment of this invention is directed to a pharmaceutically acceptable ester of compound 203. Another embodiment of this invention is directed to a pharmaceutically acceptable ester of compound 206. Another embodiment of this invention is directed to a pharmaceutically acceptable ester of compound 207. Another embodiment of this invention is directed to a pharmaceutically acceptable ester of compound 208. Another embodiment of this invention is directed to a pharmaceutically acceptable ester of compound 209. Another embodiment of this invention is directed to a pharmaceutically acceptable ester of compound 210. Another embodiment of this invention is directed to a pharmaceutically acceptable ester of compound 211. Another embodiment of this invention is directed to a pharmaceutically acceptable ester of compound 212. Another embodiment of this invention is directed to a pharmaceutically acceptable ester of compound 213. Another embodiment of this invention is directed to a pharmaceutically acceptable salt of compound 214. Another embodiment of this invention is directed to a pharmaceutically acceptable ester of compound 215. Another embodiment of this invention is directed to a pharmaceutically acceptable ester of compound 220. Another embodiment of this invention is directed to a pharmaceutically acceptable ester of compound 221. Another embodiment of this invention is directed to a pharmaceutically acceptable ester of compound 222. Another embodiment of this invention is directed to a pharmaceutically acceptable ester of compound 226. Another embodiment of this invention is directed to a pharmaceutically acceptable ester of compound 227. Another embodiment of this invention is directed to a pharmaceutically acceptable ester of compound 229. Another embodiment of this invention is directed to a pharmaceutically acceptable ester of compound 231. Another embodiment of this invention is directed to a pharmaceutically acceptable ester of compound 233. Another embodiment of this invention is directed to a pharmaceutically acceptable ester of compound 245. Another embodiment of this invention is directed to a pharmaceutically acceptable salt of compound 246. Another embodiment of this invention is directed to a pharmaceutically acceptable ester of compound 247. Another embodiment of this invention is directed to a pharmaceutically acceptable ester of compound 248. Another embodiment of this invention is directed to a pharmaceutically acceptable ester compound 249. Another embodiment of this invention is directed to a pharmaceutically acceptable ester of compound 250. Another embodiment of this invention is directed to a pharmaceutically acceptable ester compound 251. Another embodiment of this invention is directed to a pharmaceutically acceptable ester of compound 252. Another embodiment of this invention is directed to a pharmaceutically acceptable ester of compound 253. Another embodiment of this invention is directed to a pharmaceutically acceptable ester of compound 254. Another embodiment of this invention is directed to a pharmaceutically acceptable ester of compound 255. Another embodiment of this invention is directed to a pharmaceutically acceptable ester of compound 256. Another embodiment of this invention is directed to a pharmaceutically acceptable ester of compound 257. Another embodiment of this invention is directed to a pharmaceutically acceptable ester of compound 258. Another embodiment of this invention is directed to a pharmaceutically acceptable ester of compound 259. Another embodiment of this invention is directed to a pharmaceutically acceptable ester of compound 260. Another embodiment of this invention is directed to a pharmaceutically acceptable ester of compound 261. Another embodiment of this invention is directed to a pharmaceutically acceptable ester of compound 262. Another embodiment of this invention is directed to a pharmaceutically acceptable ester of compound 263. Another embodiment of this invention is directed to a pharmaceutically acceptable salt of compound 264. Another embodiment of this invention is directed to a pharmaceutically acceptable ester of compound 265. Another embodiment of this invention is directed to a pharmaceutically acceptable ester of compound 266. Another embodiment of this invention is directed to a pharmaceutically acceptable ester of compound 267. Another embodiment of this invention is directed to a pharmaceutically acceptable ester of compound 268. Another embodiment of this invention is directed to a pharmaceutically acceptable ester of compound 269. Another embodiment of this invention is directed to a pharmaceutically acceptable ester of compound 270. Another of embodiment of this invention is directed to a pharmaceutically acceptable ester of compound 271. Another embodiment of this invention is directed to a pharmaceutically acceptable ester of compound 272. Another embodiment of this invention is directed to a pharmaceutically acceptable ester of compound 273. Another embodiment of this invention is directed to a pharmaceutically acceptable ester of compound 274. Another embodiment of this invention is directed to a pharmaceutically acceptable ester of compound 275. Another embodiment of this invention is directed to a pharmaceutically acceptable ester of compound 276. Another embodiment of this invention is directed to a pharmaceutically acceptable ester of compound 277. Another embodiment of this invention is directed to a pharmaceutically acceptable ester of compound 278. Another embodiment of this invention is directed to a pharmaceutically acceptable ester of compound 279. Another embodiment of this invention is directed to a pharmaceutically acceptable ester of compound 280. Another embodiment of this invention is directed to a pharmaceutically acceptable ester of compound 281. Another embodiment of this invention is directed to a pharmaceutically acceptable ester of compound 282. Another embodiment of this invention is directed to a pharmaceutically acceptable ester of compound 283. Another embodiment of this invention is directed to a pharmaceutically acceptable ester of compound 284. Another embodiment of this invention is directed to a pharmaceutically acceptable ester of compound 285. Another embodiment of this invention is directed to a pharmaceutically acceptable ester of compound 286. Another embodiment of this invention is directed to a pharmaceutically acceptable ester of compound 287. Another embodiment of this invention is directed to a pharmaceutically acceptable ester of compound 288. Another embodiment of this invention is directed to a pharmaceutically acceptable ester of compound 289. Another embodiment of this invention is directed to a pharmaceutically acceptable ester of compound 290. Another embodiment of this invention is directed to a pharmaceutically acceptable ester of compound 291. Another embodiment of this invention is directed to a pharmaceutically acceptable ester of compound 292. Another embodiment of this invention is directed to a pharmaceutically acceptable ester of compound 293. Another embodiment of this invention is directed to a pharmaceutically acceptable ester of compound 294. Another embodiment of this invention is directed to a pharmaceutically acceptable ester of compound 295. Another embodiment of this invention is directed to a pharmaceutically acceptable ester of compound 296. Another embodiment of this invention is directed to a pharmaceutically acceptable ester of compound 297. Another embodiment of this invention is directed to a pharmaceutically acceptable ester of compound 298. Another embodiment of this invention is directed to a pharmaceutically acceptable ester of compound 299. Another embodiment of this invention is directed to a pharmaceutically acceptable ester of compound 300. Another embodiment of this invention is directed to a pharmaceutically acceptable ester of compound 301. Another embodiment of this invention is directed to a pharmaceutically acceptable ester of compound 302. Another embodiment of this invention is directed to a pharmaceutically acceptable ester of compound 303. Another embodiment of this invention is directed to a pharmaceutically acceptable ester of compound 304. Another embodiment of this invention is directed to a pharmaceutically acceptable ester of compound 305. Another embodiment of this invention is directed to a pharmaceutically acceptable ester of compound 306. Another embodiment of this invention is directed to a pharmaceutically acceptable ester of compound 307. Another embodiment of this invention is directed to a pharmaceutically acceptable ester of compound 308. Another embodiment of this invention is directed to a pharmaceutically acceptable ester of compound 309. Another embodiment of this invention is directed to a pharmaceutically acceptable ester of compound 310. Another embodiment of this invention is directed to a pharmaceutically acceptable ester of compound 311. Another embodiment of this invention is directed to a pharmaceutically acceptable ester of compound 312. Another embodiment of this invention is directed to a pharmaceutically acceptable ester of compound 313. Another embodiment of this invention is directed to a pharmaceutically acceptable ester of compound 314. Another embodiment of this invention is directed to a pharmaceutically acceptable ester of compound 315. Another embodiment of this invention is directed to a pharmaceutically acceptable ester of compound 316. Another embodiment of this invention is directed to a pharmaceutically acceptable ester of compound 317. Another embodiment of this invention is directed to a pharmaceutically acceptable ester of compound 318. Another embodiment of this invention is directed to a pharmaceutically acceptable ester of compound 319. Another embodiment of this invention is directed to a pharmaceutically acceptable ester of compound 320. Another embodiment of this invention is directed to a pharmaceutically acceptable ester of compound 321. Another embodiment of this invention is directed to a pharmaceutically acceptable ester of compound 322. Another embodiment of this invention is directed to a pharmaceutically acceptable ester of compound 323. Another embodiment of this invention is directed to a pharmaceutically acceptable ester of compound 324. Another embodiment of this invention is directed to a pharmaceutically acceptable ester of compound 325. Another embodiment of this invention is directed to a pharmaceutically acceptable ester of compound 326. Another embodiment of this invention is directed to a pharmaceutically acceptable ester of compound 327. Another embodiment of this invention is directed to a pharmaceutically acceptable ester of compound 328. Another embodiment of this invention is directed to a pharmaceutically acceptable ester of compound 329. Another embodiment of this invention is directed to a pharmaceutically acceptable ester of compound 330. Another embodiment of this invention is directed to a pharmaceutically acceptable ester of compound 331. Another embodiment of this invention is directed to a pharmaceutically acceptable ester of compound 332. Another embodiment of this invention is directed to a pharmaceutically acceptable ester of compound 333. Another embodiment of this invention is directed to a pharmaceutically acceptable ester of compound 334. Another embodiment of this invention is directed to a pharmaceutically acceptable ester of compound 335. Another embodiment of this invention is directed to a pharmaceutically acceptable ester of compound 336. Another embodiment of this invention is directed to a pharmaceutically acceptable ester of compound 337. Another embodiment of this invention is directed to a pharmaceutically acceptable ester of compound 338. Another embodiment of this invention is directed to a pharmaceutically acceptable ester of compound 339. Another embodiment of this invention is directed to a pharmaceutically acceptable ester of compound 340. Another of embodiment of this invention is directed to a pharmaceutically acceptable ester of compound 341. Another embodiment of this invention is directed to a pharmaceutically acceptable ester of compound 342. Another embodiment of this invention is directed to a pharmaceutically acceptable ester of compound 343. Another embodiment of this invention is directed to a pharmaceutically acceptable ester of compound 344. Another embodiment of this invention is directed to a pharmaceutically acceptable ester of compound 345. Another embodiment of this invention is directed to a pharmaceutically acceptable ester of compound 346. Another embodiment of this invention is directed to a pharmaceutically acceptable ester of compound 347. Another embodiment of this invention is directed to a pharmaceutically acceptable ester of compound 348. Another embodiment of this invention is directed to a pharmaceutically acceptable ester of compound 349. Another embodiment of this invention is directed to a pharmaceutically acceptable ester of compound 350. Another embodiment of this invention is directed to a pharmaceutically acceptable ester of compound 351. Another embodiment of this invention is directed to a pharmaceutically acceptable ester of compound 352. Another embodiment of this invention is directed to a pharmaceutically acceptable ester of compound 353. Another embodiment of this invention is directed to a pharmaceutically acceptable ester of compound 354. Another embodiment of this invention is directed to a pharmaceutically acceptable ester of compound 355. Another embodiment of this invention is directed to a pharmaceutically acceptable ester of compound 356. Another embodiment of this invention is directed to a pharmaceutically acceptable ester of compound 357. Another embodiment of this invention is directed to a pharmaceutically acceptable ester of compound 358. Another embodiment of this invention is directed to a pharmaceutically acceptable ester of compound 359. Another embodiment of this invention is directed to a pharmaceutically acceptable ester of compound 360. Another embodiment of this invention is directed to a pharmaceutically acceptable ester of compound 361. Another embodiment of this invention is directed to a pharmaceutically acceptable ester of compound 362. Another embodiment of this invention is directed to a pharmaceutically acceptable ester of compound 363. Another embodiment of this invention is directed to a pharmaceutically acceptable ester of compound 364. Another embodiment of this invention is directed to a pharmaceutically acceptable ester of compound 365. Another embodiment of this invention is directed to a pharmaceutically acceptable ester of compound 366. Another embodiment of this invention is directed to a pharmaceutically acceptable ester of compound 367. Another embodiment of this invention is directed to a pharmaceutically acceptable ester of compound 368. Another embodiment of this invention is directed to a pharmaceutically acceptable ester of compound 369. Another embodiment of this invention is directed to a pharmaceutically acceptable ester of compound 370. Another of embodiment of this invention is directed to a pharmaceutically acceptable ester of compound 371. Another embodiment of this invention is directed to a pharmaceutically acceptable ester of compound 372. Another embodiment of this invention is directed to a pharmaceutically acceptable ester of compound 373. Another embodiment of this invention is directed to a pharmaceutically acceptable ester of compound 374. Another embodiment of this invention is directed to a pharmaceutically acceptable ester of compound 375. Another embodiment of this invention is directed to a pharmaceutically acceptable ester of compound 376. Another embodiment of this invention is directed to a pharmaceutically acceptable ester of compound 377. Another embodiment of this invention is directed to a pharmaceutically acceptable ester of compound 378. Another embodiment of this invention is directed to a pharmaceutically acceptable ester of compound 379. Another embodiment of this invention is directed to a pharmaceutically acceptable ester of compound 380. Another embodiment of this invention is directed to a pharmaceutically acceptable ester of compound 381. Another embodiment of this invention is directed to a pharmaceutically acceptable ester of compound 382. Another embodiment of this invention is directed to a pharmaceutically acceptable ester of compound 383. Another embodiment of this invention is directed to a pharmaceutically acceptable ester of compound 384. Another embodiment of this invention is directed to a pharmaceutically acceptable ester of compound 385. Another embodiment of this invention is directed to a pharmaceutically acceptable ester of compound 386. Another embodiment of this invention is directed to a pharmaceutically acceptable ester of compound 387. Another embodiment of this invention is directed to a pharmaceutically acceptable ester of compound 388. Another embodiment of this invention is directed to a pharmaceutically acceptable ester of compound 389. Another embodiment of this invention is directed to a pharmaceutically acceptable ester of compound 390. Another embodiment of this invention is directed to a pharmaceutically acceptable ester of compound 391. Another embodiment of this invention is directed to a pharmaceutically acceptable ester of compound 392. Another embodiment of this invention is directed to a pharmaceutically acceptable ester of compound 393. Another embodiment of this invention is directed to a pharmaceutically acceptable ester of compound 394.

Another embodiment of this invention is directed to a solvate of compound Q11. Another embodiment of this invention is directed to a solvate of compound R4. Another embodiment of this invention is directed to a solvate of compound U2. Another embodiment of this invention is directed to a solvate of compound W3. Another embodiment of this invention is directed to a solvate of compound X2. Another embodiment of this invention is directed to a solvate of compound Y3. Another embodiment of this invention is directed to a solvate of compound Z2. Another embodiment of this invention is directed to a solvate of compound Aa2. Another embodiment of this invention is directed to a solvate of compound Ab2. Another embodiment of this invention is directed to a solvate of compound Ac6. Another embodiment of this invention is directed to a solvate of compound Af3. Another embodiment of this invention is directed to a solvate of compound Ag4. Another embodiment of this invention is directed to a solvate of compound Ah2. Another embodiment of this invention is directed to a solvate of compound Ai2. Another embodiment of this invention is directed to a solvate of compound Aj4. Another embodiment of this invention is directed to a solvate of compound Ak2. Another embodiment of this invention is directed to a solvate of compound Al2. Another embodiment of this invention is directed to a solvate of compound Am3. Another embodiment of this invention is directed to a solvate of compound Am4. Another embodiment of this invention is directed to a solvate of compound Ao5. Another embodiment of this invention is directed to a solvate of compound Ap15. Another embodiment of this invention is directed to a solvate of compound Aq7. Another embodiment of this invention is directed to a solvate of compound Ar3. Another embodiment of this invention is directed to a solvate of compound 201. Another embodiment of this invention is directed to a solvate of compound 202. Another embodiment of this invention is directed to a solvate of compound 203. Another embodiment of this invention is directed to a solvate of compound 206. Another embodiment of this invention is directed to a solvate of compound 207. Another embodiment of this invention is directed to a solvate of compound 208. Another embodiment of this invention is directed to a solvate of compound 209. Another embodiment of this invention is directed to a solvate of compound 210. Another embodiment of this invention is directed to a solvate of compound 211. Another embodiment of this invention is directed to a solvate of compound 212. Another embodiment of this invention is directed to a solvate of compound 213. Another embodiment of this invention is directed to a solvate of compound 214. Another embodiment of this invention is directed to a solvate of compound 215. Another embodiment of this invention is directed to a solvate of compound 220. Another embodiment of this invention is directed to a solvate of compound 221. Another embodiment of this invention is directed to a solvate of compound 222. Another embodiment of this invention is directed to a solvate of compound 226. Another embodiment of this invention is directed to a solvate of compound 227. Another embodiment of this invention is directed to a solvate of compound 229. Another embodiment of this invention is directed to a solvate of compound 231. Another embodiment of this invention is directed to a solvate of compound 233. Another embodiment of this invention is directed to a solvate of compound 245. Another embodiment of this invention is directed to a solvate of compound 246. Another embodiment of this invention is directed to a solvate of compound 247. Another embodiment of this invention is directed to a solvate of compound 248. Another embodiment of this invention is directed to a solvate of compound 249. Another embodiment of this invention is directed to a solvate of compound 250. Another embodiment of this invention is directed to a solvate of compound 251. Another embodiment of this invention is directed to a solvate of compound 252. Another embodiment of this invention is directed to a solvate of compound 253. Another embodiment of this invention is directed to a solvate of compound 254. Another embodiment of this invention is directed to a solvate of compound 255. Another embodiment of this invention is directed to a solvate of compound 256. Another embodiment of this invention is directed to a solvate of compound 257. Another embodiment of this invention is directed to a solvate of compound 258. Another embodiment of this invention is directed to a solvate of compound 259. Another embodiment of this invention is directed to a solvate of compound 260. Another embodiment of this invention is directed to a solvate of compound 261. Another embodiment of this invention is directed to a solvate of compound 262. Another embodiment of this invention is directed to a solvate of compound 263. Another embodiment of this invention is directed to a solvate of compound 264. Another embodiment of this invention is directed to a solvate of compound 265. Another embodiment of this invention is directed to a solvate of compound 266. Another embodiment of this invention is directed to a solvate of compound 267. Another embodiment of this invention is directed to a solvate of compound 268. Another embodiment of this invention is directed to a solvate of compound 269. Another embodiment of this invention is directed to a solvate of compound 270. Another embodiment of this invention is directed to a solvate of compound 271. Another embodiment of this invention is directed to a solvate of compound 272. Another embodiment of this invention is directed to a solvate of compound 273. Another embodiment of this invention is directed to a solvate of compound 274. Another embodiment of this invention is directed to a solvate of compound 275. Another embodiment of this invention is directed to a solvate of compound 276. Another embodiment of this invention is directed to a solvate of compound 277. Another embodiment of this invention is directed to a solvate of compound 278. Another embodiment of this invention is directed to a solvate of compound 279. Another embodiment of this invention is directed to a solvate of compound 280. Another embodiment of this invention is directed to a solvate of compound 281. Another embodiment of this invention is directed to a solvate of compound 282. Another embodiment of this invention is directed to a solvate of compound 283. Another embodiment of this invention is directed to a solvate of compound 284. Another embodiment of this invention is directed to a solvate of compound 285. Another embodiment of this invention is directed to a solvate of compound 286. Another embodiment of this invention is directed to a solvate of compound 287. Another embodiment of this invention is directed to a solvate of compound 288. Another embodiment of this invention is directed to a solvate of compound 289. Another embodiment of this invention is directed to a solvate of compound 290. Another embodiment of this invention is directed to a solvate of compound 291. Another embodiment of this invention is directed to a solvate of compound 292. Another embodiment of this invention is directed to a solvate of compound 293. Another embodiment of this invention is directed to a solvate of compound 294. Another embodiment of this invention is directed to a solvate of compound 295. Another embodiment of this invention is directed to a solvate of compound 296. Another embodiment of this invention is directed to a solvate of compound 297. Another embodiment of this invention is directed to a solvate of compound 298.

Another embodiment of this invention is directed to a solvate of compound 299. Another embodiment of this invention is directed to a solvate of compound 300. Another embodiment of this invention is directed to a solvate of compound 301. Another embodiment of this invention is directed to a solvate of compound 302. Another embodiment of this invention is directed to a solvate of compound 303. Another embodiment of this invention is directed to a solvate of compound 304. Another embodiment of this invention is directed to a solvate of compound 305. Another embodiment of this invention is directed to a solvate of compound 306. Another embodiment of this invention is directed to a solvate of compound 307. Another embodiment of this invention is directed to a solvate of compound 308. Another embodiment of this invention is directed to a solvate of compound 309. Another embodiment of this invention is directed to a solvate of compound 310. Another embodiment of this invention is directed to a solvate of compound 311. Another embodiment of this invention is directed to a solvate of compound 312. Another embodiment of this invention is directed to a solvate of compound 313. Another embodiment of this invention is directed to a solvate of compound 314. Another embodiment of this invention is directed to a solvate of compound 315. Another embodiment of this invention is directed to a solvate of compound 316. Another embodiment of this invention is directed to a solvate of compound 317. Another embodiment of this invention is directed to a solvate of compound 318. Another embodiment of this invention is directed to a solvate of compound 319. Another embodiment of this invention is directed to a solvate of compound 320. Another embodiment of this invention is directed to a solvate of compound 321. Another embodiment of this invention is directed to a solvate of compound 322. Another embodiment of this invention is directed to a solvate of compound 323. Another embodiment of this invention is directed to a solvate of compound 324. Another embodiment of this invention is directed to a solvate of compound 325. Another embodiment of this invention is directed to a solvate of compound 326. Another embodiment of this invention is directed to a solvate of compound 327. Another embodiment of this invention is directed to a solvate of compound 328. Another embodiment of this invention is directed to a solvate of compound 329. Another embodiment of this invention is directed to a solvate of compound 330. Another embodiment of this invention is directed to a solvate of compound 331. Another embodiment of this invention is directed to a solvate of compound 332. Another embodiment of this invention is directed to a solvate of compound 333. Another embodiment of this invention is directed to a solvate of compound 334. Another embodiment of this invention is directed to a solvate of compound 335. Another embodiment of this invention is directed to a solvate of compound 336. Another embodiment of this invention is directed to a solvate of compound 337. Another embodiment of this invention is directed to a solvate of compound 338. Another embodiment of this invention is directed to a solvate of compound 339. Another embodiment of this invention is directed to a solvate of compound 340. Another embodiment of this invention is directed to a solvate of compound 341. Another embodiment of this invention is directed to a solvate of compound 342. Another embodiment of this invention is directed to a solvate of compound 343. Another embodiment of this invention is directed to a solvate of compound 344. Another embodiment of this invention is directed to a solvate of compound 345. Another embodiment of this invention is directed to a solvate of compound 346. Another embodiment of this invention is directed to a solvate of compound 347. Another embodiment of this invention is directed to a solvate of compound 348. Another embodiment of this invention is directed to a solvate of compound 349. Another embodiment of this invention is directed to a solvate of compound 350. Another embodiment of this invention is directed to a solvate of compound 351. Another embodiment of this invention is directed to a solvate of compound 352. Another embodiment of this invention is directed to a solvate of compound 353. Another embodiment of this invention is directed to a solvate of compound 354. Another embodiment of this invention is directed to a solvate of compound 355. Another embodiment of this invention is directed to a solvate of compound 356. Another embodiment of this invention is directed to a solvate of compound 357. Another embodiment of this invention is directed to a solvate of compound 358. Another embodiment of this invention is directed to a solvate of compound 359. Another embodiment of this invention is directed to a solvate of compound 360. Another embodiment of this invention is directed to a solvate of compound 361. Another embodiment of this invention is directed to a solvate of compound 362. Another embodiment of this invention is directed to a solvate of compound 363. Another embodiment of this invention is directed to a solvate of compound 364. Another embodiment of this invention is directed to a solvate of compound 365. Another embodiment of this invention is directed to a solvate of compound 366. Another embodiment of this invention is directed to a solvate of compound 367. Another embodiment of this invention is directed to a solvate of compound 368. Another embodiment of this invention is directed to a solvate of compound 369. Another embodiment of this invention is directed to a solvate of compound 370. Another embodiment of this invention is directed to a solvate of compound 371. Another embodiment of this invention is directed to a solvate of compound 372. Another embodiment of this invention is directed to a solvate of compound 373. Another embodiment of this invention is directed to a solvate of compound 374. Another embodiment of this invention is directed to a solvate of compound 375. Another embodiment of this invention is directed to a solvate of compound 376. Another embodiment of this invention is directed to a solvate of compound 377. Another embodiment of this invention is directed to a solvate of compound 378. Another embodiment of this invention is directed to a solvate of compound 379. Another embodiment of this invention is directed to a solvate of compound 380. Another embodiment of this invention is directed to a solvate of compound 381. Another embodiment of this invention is directed to a solvate of compound 382. Another embodiment of this invention is directed to a solvate of compound 383. Another embodiment of this invention is directed to a solvate of compound 384. Another embodiment of this invention is directed to a solvate of compound 385. Another embodiment of this invention is directed to a solvate of compound 386. Another embodiment of this invention is directed to a solvate of compound 387. Another embodiment of this invention is directed to a solvate of compound 388. Another embodiment of this invention is directed to a solvate of compound 389. Another embodiment of this invention is directed to a solvate of compound 390. Another embodiment of this invention is directed to a solvate of compound 391. Another embodiment of this invention is directed to a solvate of compound 392. Another embodiment of this invention is directed to a solvate of compound 393. Another embodiment of this invention is directed to a solvate of compound 394.

In the embodiments below Groups A and B are as defined above.

Another embodiment of this invention is directed to a compound selected from the group consisting of the compounds of Group A (and in another embodiment the compounds are selected from the compounds of Group B).

Another embodiment of this invention is directed to a pharmaceutically acceptable salt of a compound selected from the group consisting of the compounds of Group A (and in another embodiment the compounds are selected from the compounds of Group B).

Another embodiment of this invention is directed to a pharmaceutically acceptable ester of a compound selected from the group consisting of the compounds of Group A (and in another embodiment the compounds are selected from the compounds of Group B).

Another embodiment of this invention is directed to a solvate of a compound selected from the group consisting of the compounds of Group A (and in another embodiment the compounds are selected from the compounds of Group B).

Another embodiment of this invention is directed to a compound selected from the group consisting of the compounds of Group A (and in another embodiment the compounds are selected from the compounds of Group B) in pure and isolated form.

Another embodiment of this invention is directed to a compound selected from the group consisting of the compounds of Group A (and in another embodiment the compounds are selected from the compounds of Group B) in pure form.

Another embodiment of this invention is directed to a compound selected from the group consisting of the compounds of Group A (and in another embodiment the compounds are selected from the compounds of Group B) in isolated form.

Another embodiment of this invention is directed to a pharmaceutical composition comprising a therapeutically effective amount of at least one compound selected from the group consisting of the compounds of Group A (and in another embodiment the compounds are selected from the compounds of Group B) or a pharmaceutically acceptable salt, solvate, or ester thereof, and at least one pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B) and a pharmaceutically acceptable carrier.

Another embodiment of this invention is directed to a pharmaceutical composition comprising an effective amount of a pharmaceutically acceptable salt of one or more (e.g., one) compounds selected from the group consisting of the compounds of Group A (and in another embodiment the compounds are selected from the compounds of Group B) and a pharmaceutically acceptable carrier.

Another embodiment of this invention is directed to a pharmaceutical composition comprising an effective amount of a pharmaceutically acceptable ester of one or more (e.g., one) compounds selected from the group consisting of the compounds of Group A (and in another embodiment the compounds are selected from the compounds of Group B) and a pharmaceutically acceptable carrier.

Another embodiment of this invention is directed to a pharmaceutical composition comprising an effective amount of a solvate of one or more (e.g., one) compounds selected from the group consisting of the compounds of Group A (and in another embodiment the compounds are selected from the compounds of Group B) and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising a therapeutically effective amount of at least one compound selected from the group consisting of the compounds of Group A (and in another embodiment the compounds are selected from the compounds of Group B), or a pharmaceutically acceptable salt, solvate, or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more BACE inhibitors, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more cholinesterase inhibitors (e.g., acetyl- and/or butyrylcholinesterase inhibitors), and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more muscarinic antagonists (e.g., $m_1$ or $m_2$ antagonists), and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of Exelon (rivastigmine), and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of Cognex (tacrine), and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of a Tau kinase inhibitor, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more Tau kinase inhibitor (e.g., GSK3beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one anti-Abeta vaccine (active immunization), and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more APP ligands, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more fibrates (for example, clofibrate, Clofibride, Etofibrate, Aluminium Clofibrate), and a pharmaceutically acceptable carrier Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more LXR agonists, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more LRP mimics, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more 5-HT6 receptor antagonists, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more nicotinic receptor agonists, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more H3 receptor antagonists, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more histone deacetylase inhibitors, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more hsp90 inhibitors, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more m1 muscarinic receptor agonists, and a pharmaceutically acceptable carrier.

Another embodiment of this invention is directed to combinations, i.e., a pharmaceutical composition, comprising a pharmaceutically acceptable carrier, an effective (i.e., therapeutically effective) amount of one or more compounds selected from the group consisting of the compounds of Group A (and in another embodiment the compounds are selected from the compounds of Group B), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more one mGluR2/3 antagonists, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more PAI-1 inhibitors, and a pharmaceutically acceptable carrier.

Another embodiment of this invention is directed to a pharmaceutical composition comprising an effective amount of one or more (e.g., one) compounds selected from the group consisting of the compounds of Group A (and in another embodiment the compounds are selected from the compounds of Group B), and effective amount of one or more agents that can induce Abeta efflux such as gelsolin, and a pharmaceutically acceptable carrier.

The compounds selected from the group consisting of the compounds of Group A (and in another embodiment the compounds are selected from the compounds of Group B) can be useful as gamma secretase modulators and can be useful in the treatment and prevention of diseases such as, for example, central nervous system disorders (such as Alzheimers disease and Downs Syndrome), mild cognitive impairment, glaucoma, cerebral amyloid angiopathy, stroke, dementia, microgliosis, brain inflammation, and olfactory function loss.

Another embodiment of this invention is directed to a method of treating a central nervous system disorder comprising administering a therapeutically effective amount of at least one compound selected from the group consisting of the compounds of Group A (and in another embodiment the compounds are selected from the compounds of Group B) to a patient in need of such treatment.

Another embodiment of this invention is directed to a method of treating a central nervous system disorder comprising administering a therapeutically effective amount of a pharmaceutical composition comprising a therapeutically effective amount of at least one compound selected from the group consisting of the compounds of Group A (and in another embodiment the compounds are selected from the compounds of Group B), or a pharmaceutically acceptable salt, solvate, or ester thereof, and at least one pharmaceutically acceptable carrier.

Another embodiment of this invention is directed to a method of treating a central nervous system disorder comprising administering a therapeutically effective amount of a pharmaceutical composition comprising a therapeutically effective amount of at least one compound selected from the group consisting of the compounds of Group A (and in another embodiment the compounds are selected from the compounds of Group B), or a pharmaceutically acceptable salt, solvate, or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Another embodiment of this invention is directed to a method for modulating (including inhibiting, antagonizing and the like) gamma-secretase comprising administering an effective amount of one or more (e.g., one) compounds selected from the group consisting of the compounds of Group A (and in another embodiment the compounds are selected from the compounds of Group B) to a patient in need of such treatment.

Another embodiment of this invention is directed to a method for modulating (including inhibiting, antagonizing and the like) gamma-secretase, comprising administering an effective amount of a compound selected from the group consisting of the compounds of Group A (and in another embodiment the compounds are selected from the compounds of Group B) to a patient in need of treatment.

Another embodiment of this invention is directed to a method of treating one or more neurodegenerative diseases, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating one or more neurodegenerative diseases, comprising administering an effective amount of a compound selected from the group consisting of the compounds of Group A (and in another embodiment the compounds are selected from the compounds of Group B) to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of a compound selected from the group consisting of the compounds of Group A (and in another embodiment the compounds are selected from the compounds of Group B) to a patient in need of treatment.

Another embodiment of this invention is directed to a method of treating Alzheimer's disease, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating Alzheimer's disease, comprising administering an effective amount of a compound selected from the group consisting of the compounds of Group A (and in another embodiment the compounds are selected from the compounds of Group B) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds selected from the group consisting of the compounds of Group A (and in another embodiment the compounds are selected from the compounds of Group B) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound selected from the group consisting of the compounds of Group A (and in another embodiment the compounds are selected from the compounds of Group B) to a patient in need of treatment.

Another embodiment of this invention is directed to a method of treating mild cognitive impairment, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating glaucoma, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating cerebral amyloid angiopathy, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating stroke, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating dementia, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating microgliosis, comprising administering an effective amount of one or more (e.g., one) compounds selected from the group consisting of Group A (and in another embodiment the compounds are selected from the compounds of Group B) to a patient in need of treatment.

Another embodiment of this invention is directed to a method of treating brain inflammation, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating olfactory function loss, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating Downs syndrome, comprising administering an effective amount of one or more (e.g., one) compounds selected from the group consisting of the compounds of Group A (and in another embodiment the compounds are selected from the compounds of Group B) to a patient in need of treatment.

Another embodiment of this invention is directed to a method of treating Downs syndrome, comprising administering an effective amount of a compound selected from the group consisting of the compounds of Group A (and in another embodiment the compounds are selected from the compounds of Group B) to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds selected from the group consisting of the compounds of Group A (and in another embodiment the compounds are selected from the compounds of Group B) and the administration of an effective amount of one or more (e.g., one) other pharmaceutical active ingredients (e.g., drugs). The compounds selected from the group consisting of the compounds of Group A (and in another embodiment the compounds are selected from the compounds of Group B) and the other drugs can be administered separately (i.e., each is in its own separate dosage form), or the compounds selected from the group consisting of the compounds of Group A (and in another embodiment the compounds are selected from the compounds of Group B) can be combined with the other drugs in the same dosage form.

Thus, other embodiments of this invention are directed to any one of the methods of treatment, or methods of inhibiting, described herein, wherein an effective amount of the compound selected from the group consisting of the compounds of Group A (and in another embodiment the compounds are selected from the compounds of Group B) is used in combination with an effective amount of one or more other pharmaceutically active ingredients (e.g., drugs). The other pharmaceutically active ingredients (i.e., drugs) are selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues: histamine H3 antagonists; AMPA agonists; PDE4 inhibitors; GABA$_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Another embodiment of this invention is directed to a method of treating Alzheimer's disease, comprising administering an effective amount of one or more (e.g., one) compounds selected from the group consisting of the compounds of Group A (and in another embodiment the compounds are selected from the compounds of Group B), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of a compound selected from the group consisting of the compounds of Group A (and in another embodiment the compounds are selected from the compounds of Group B), in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of one or more (e.g., one) compounds selected from the group consisting of the compounds of Group A (and in another embodiment the compounds are selected from the compounds of Group B), in combination with an effective amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective amount of one or more (e.g., one) compounds selected from the group consisting of the compounds of Group A (and in another embodiment the compounds are selected from the compounds of Group B), in combination with an effective amount of one or more BACE inhibitors.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of Exelon (rivastigmine).

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of Cognex (tacrine).

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of a Tau kinase inhibitor.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds selected from the group consisting of the compounds of Group A (and in another embodiment the compounds are selected from the compounds of Group B), in combination with an effective amount of one anti-Abeta vaccination (active immunization).

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more APP ligands.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more agents that upregulate insulin degrading enzyme and/or neprilysin.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds selected from the group consisting of the compounds of Group A (and in another embodiment the compounds are selected from the compounds of Group B), in combination with an effective amount of one or more fibrates (for example, clofibrate, Clofibride, Etofibrate, Aluminium Clofibrate).

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more LXR agonists.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more LRP mimics.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more 5-HT6 receptor antagonists.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more nicotinic receptor agonists.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more H3 receptor antagonists.

This invention also provides a method of treating Alzheimer's disease, comprising administering an effective amount of one or more compounds selected from the group consisting of the compounds of Group A (and in another embodiment the compounds are selected from the compounds of Group B), in combination with an effective amount of one or more histone deacetylase inhibitors.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more hsp90 inhibitors.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more m1 muscarinic receptor agonists.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more 5-HT6 receptor antagonists mGluR1 or mGluR5 positive allosteric modulators or agonists Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more mGluR2/3 antagonists.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more anti-inflammatory agents that can reduce neuroinflammation.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more Prostaglandin EP2 receptor antagonists.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more PAI-1 inhibitors.

Another embodiment of this invention is directed to a method of treating Alzheimer's disease, comprising administering an effective amount of one or more compounds selected from the group consisting of the compounds of Group A (and in another embodiment the compounds are selected from the compounds of Group B), in combination with an effective amount of one or more agents that can induce Abeta efflux such as gelsolin.

Another embodiment of this invention is directed to a method of treating Downs syndrome, comprising administering an effective amount of one or more (e.g., one) compounds selected from the group consisting of the compounds of Group A (and in another embodiment the compounds are selected from the compounds of Group B), in combination with an effective amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective amount of a compound selected from the group consisting of the compounds of Group A (and in another embodiment the compounds are selected from the compounds of Group B), in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a kit comprising, in separate containers, in a single package, pharmaceutical compositions for use in combination, wherein one container comprises an effective amount of a compound selected from the group consisting of the compounds of Group A (and in another embodiment the compounds are selected from the compounds of Group B) in a pharmaceutically acceptable carrier, and another container (i.e., a second container) comprises an effective amount of another pharmaceutically active ingredient (as described above), the combined quantities of the compound selected from the group consisting of the compounds of Group A (and in another embodiment the compounds are selected from the compounds of Group B) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase, or (e) mild cognitive impairment, or (f) glaucoma, or (g) cerebral amyloid angiopathy, or (h) stroke, or (i) dementia, or (j) microgliosis, or (k) brain inflammation, or (l) olfactory function loss.

This invention also provides a kit comprising, in separate containers, in a single package, pharmaceutical compositions for use in combination, wherein one container comprises an effective amount of a compound selected from the group consisting of the compounds of Group A (and in another embodiment the compounds are selected from the compounds of Group B) in a pharmaceutically acceptable carrier, and another container (i.e., a second container) comprises an effective amount of another pharmaceutically active ingredient (as described above), the combined quantities of the compound selected from the group consisting of the compounds of Group A (and in another embodiment the compounds are selected from the compounds of Group B) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

As used herein, the following terms, unless otherwise indicated, shall be understood to have the following meanings:

"ADDP" means 1,1'-(azodicarbonyl)dipiperidine.
"DCM" means dichloromethane.
"(DHQ)$_2$PHAL" means

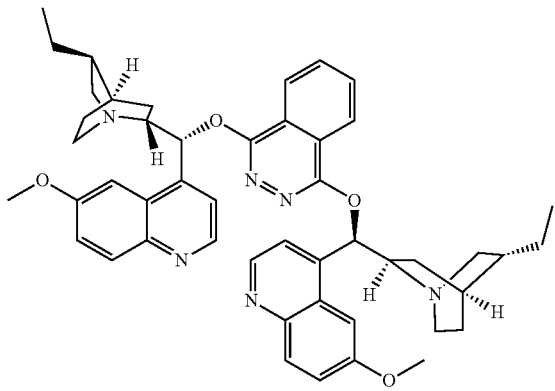 [SMILES: CC[C@@H]1CN2CC[C@@H]1C[C@@H]2[C@H](Oc1nnc(O[C@H](c2ccnc3ccc(OC)cc23)[C@H]2C[C@@H]3CCN2C[C@@H]3CC)c2ccccc12)c1ccnc2ccc(OC)cc12]

"DIAD" means di-isopropylazodicarboxylate
"DIEA" means di-isopropylethylamine
"DMF" means dimethylformamide.

"EDCI" means N-ethyl-N'-dimethylaminopropyl carbodiimide
"EtOAc" means ethyl acetate
"TEA" means triethylamine
"TFA" means trifluoroacetic acid
"At least one" means one or more than one, for example, 1, 2 or 3, or in another example, 1 or 2, or in another example 1.
"One or more" with reference to the use of the compounds of this invention means that one or more than one compound is used, for example, 1, 2 or 3, or in another example, 1 or 2, or in another example 1.
"Patient" includes both human and animals.
"Mammal" means humans and other mammalian animals.
It is noted that the carbons of the compounds of Group A or B and other formulas herein may be replaced with 1 to 3 silicon atoms so tong as all valency requirements are satisfied.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkenyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine. "Halo" refers to fluoro, chloro, bromo or iodo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$NC(O)—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

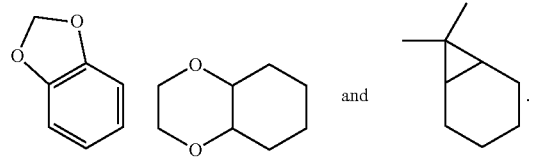

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a heterocyclyl ring wherein a single moiety (e.g =O) simultaneously replaces two available hydrogens on the same carbon atom on a ring system. An example of such moiety is pyrrolidone:

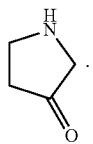

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

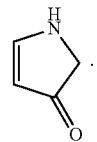

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

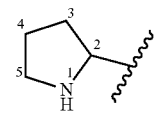

there is no —OH attached directly to carbons marked 2 and 5.

It should also be noted that tautomeric forms such as, for example, the moieties:

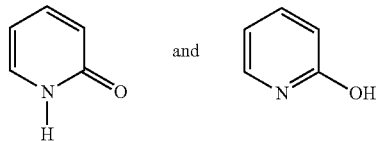 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof, Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent (or in a compound of Group A or B), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Group A or B or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethytaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$) alkyl, and the like.

Similarly, if a compound of Group A or B contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Group A or B incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$alkyl and $Y^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(11, article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Group A or B can form salts which are also within the scope of this invention. Reference to a compound of Group A or B herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Group A or B contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of Group A or B may be formed, for example, by reacting a compound of Group A or B with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Group A or B, and salts, solvates, esters and prodrugs thereof, may exist in their tautomeric form (for example, as an amide, enol, keto or imino ether). All such tautomeric forms are contemplated herein as part of the present invention.

The compounds Group A or B may contain asymmetric or chiral centers, and, therefore, exist in different stereoisomeric forms. It is intended that all stereoisomeric forms of the compounds Group A or B as well as mixtures thereof, including racemic mixtures, form part of the present invention. In addition, the present invention embraces all geometric and positional isomers. For example, if a compound Group A or B incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds Group A or B may be atropisomers (e.g., substituted biaryls) and are considered as part of this invention. Enantiomers can also be separated by use of chiral HPLC column.

It is also possible that the compounds Group A or B may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Group A or B incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of the invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of the invention can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of the invention, in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Group A or B, and of the salts, solvates, esters and prodrugs of the compounds of Group A or B, are intended to be included in the present invention.

The compounds according to the invention can have pharmacological properties; in particular, the compounds of Group A or B can be modulators of gamma secretase (including inhibitors, antagonists and the like).

More specifically, the compounds of Group A or B can be useful in the treatment of a variety of disorders of the central nervous system including, for example, including, but not limited to, Alzheimer's disease, AIDS-related dementia, Parkinson's disease, amyotrophic lateral sclerosis, retinitis pigmentosa, spinal muscular atrophy and cerebellar degeneration and the like.

Another aspect of this invention is a method of treating a mammal (e.g., human) having a disease or condition of the central nervous system by administering a therapeutically effective amount of at least one compound of Group A or B, or a pharmaceutically acceptable salt, solvate, ester or prodrug of said compound to the mammal.

A preferred dosage is about 0.001 to 500 mg/kg of body weight/day of the compound of Group A or B. An especially preferred dosage is about 0.01 to 25 mg/kg of body weight/day of a compound of Group A or B, or a pharmaceutically acceptable salt or solvate of said compound.

The compounds of this invention may also be useful in combination (administered together or sequentially) with one or more additional agents listed above.

The compounds of this invention may also be useful in combination (administered together or sequentially) with one or more compounds selected from the group consisting of Aβ antibody inhibitors, gamma secretase inhibitors and beta secretase inhibitors.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of Group A or B, or a pharmaceutically acceptable salt, solvate, ester or prodrug thereof, and an amount of one or more additional agents listed above wherein the amounts of the compounds/treatments result in desired therapeutic effect.

The pharmacological properties of the compounds of this invention may be confirmed by a number of pharmacological assays. Certain assays are exemplified later in this document.

This invention is also directed to pharmaceutical compositions which comprise at least one compound of Group A or B, or a pharmaceutically acceptable salt, solvate, ester or prodrug of said compound and at least one pharmaceutically acceptable carrier.

Another embodiment of this invention is directed to a pharmaceutically acceptable salt of a compound of Group A or B.

Another embodiment of this invention is directed to a pharmaceutically acceptable ester of a compound of Group A or B.

Another embodiment of this invention is directed to a solvate of a compound of Group A or B.

Another embodiment of this invention is directed to a compound of Group A or B in isolated form.

Another embodiment of this invention is directed to a compound of Group A or B in pure form.

Another embodiment of this invention is directed to a compound of Group A or B in pure and isolated form.

Another embodiment of this invention is directed to a pharmaceutical composition comprising an effective amount of one or more (e.g., one) compounds of Group A or B and a pharmaceutically acceptable carrier.

Another embodiment of this invention is directed to a pharmaceutical composition comprising an effective amount of a pharmaceutically acceptable salt of one or more (e.g., one) compounds of Group A or B and a pharmaceutically acceptable carrier.

Another embodiment of this invention is directed to a pharmaceutical composition comprising an effective amount of a pharmaceutically acceptable ester of one or more (e.g., one) compounds of Group A or B and a pharmaceutically acceptable carrier.

Another embodiment of this invention is directed to a pharmaceutical composition comprising an effective amount of a solvate of one or more (e.g., one) compounds of Group A or B and a pharmaceutically acceptable carrier.

Another embodiment of this invention is directed to a pharmaceutical composition comprising an effective amount of one or more (e.g., one) compounds of Group A or B, and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g., one) compounds of Group A or B, and effective amount of one or more BACE inhibitors, and a pharmaceutically acceptable carrier.

Another embodiment of this invention is directed to a pharmaceutical composition comprising an effective amount of one or more (e.g., one) compounds of Group A or B, and effective amount of one or more cholinesterase inhibitors (e.g., acetyl- and/or butyrylchlolinesterase inhibitors), and a pharmaceutically acceptable carrier.

The compounds of Group A or B can be useful as gamma secretase modulators and can be useful in the treatment and prevention of diseases such as, for example, central nervous system disorders such as Alzheimers disease and Downs Syndrome.

Thus, another embodiment of this invention is directed to a method for modulating (including inhibiting, antagonizing and the like) gamma-secretase comprising administering an effective amount of one or more (e.g., one) compounds of Group A or B to a patient in need of such treatment.

Another embodiment of this invention is directed to a method for modulating (including inhibiting, antagonizing and the like) gamma-secretase, comprising administering an effective amount of a compound of Group A or B to a patient in need of treatment.

Another embodiment of this invention is directed to a method of treating one or more neurodegenerative diseases, comprising administering an effective amount of one or more (e.g., one) compounds of Group A or B to a patient in need of treatment.

Another embodiment of this invention is directed to a method of treating one or more neurodegenerative diseases, comprising administering an effective amount of a compound of Group A or B to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of one or more (e.g., one) compounds of Group A or B to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of a compound of Group A or B to a patient in need of treatment.

Another embodiment of this invention is directed to a method of treating Alzheimer's disease, comprising administering an effective amount of one or more (e.g., one) compounds of Group A or B to a patient in need of treatment.

Another embodiment of this invention is directed to a method of treating Alzheimer's disease, comprising administering an effective amount of a compound of Group A or B to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of Group A or B and the administration of an effective amount of one or more (e.g., one) other pharmaceutical active ingredients (e.g., drugs). The compounds of Group A or B and the other drugs can be administered separately (i.e., each is in its own separate dosage form), or the compounds of Group A or B I can be combined with the other drugs in the same dosage form.

Thus, other embodiments of this invention are directed to any one of the methods of treatment, or methods of inhibiting, described herein, wherein an effective amount of the compound of Group A or B is used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylcholinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Another embodiment of this invention is directed to a method of treating Alzheimer's disease, comprising administering an effective amount of one or more (e.g., one) compounds of Group A or B, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of a compound of Group A or B, in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of one or more (e.g., one) compounds of Group A or B, in combination with an effective amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective amount of one or more (e.g., one) compounds of Group A or B, in combination with an effective amount of one or more BACE inhibitors.

Another embodiment of this invention is directed to a method of treating Alzheimer's disease, comprising administering an effective amount of one or more compounds of Group A or B, in combination with an effective amount of Exelon (rivastigmine).

Another embodiment of this invention is directed to a method of treating Alzheimer's disease, comprising administering an effective amount of one or more compounds of Group A or B, in combination with an effective amount of Cognex (tacrine).

Another embodiment of this invention is directed to a method of treating Alzheimer's disease, comprising administering an effective amount of one or more compounds of Group A or B, in combination with an effective amount of a Tau kinase inhibitor.

Another embodiment of this invention is directed to a method of treating Alzheimer's disease, comprising administering an effective amount of one or more compounds of Group A or B, in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds of Group A or B, in combination with an effective amount of one anti-Abeta vaccination (active immunization).

Another embodiment of this invention is directed to a method of treating Alzheimer's disease, comprising administering an effective amount of one or more compounds of Group A or B, in combination with an effective amount of one or more APP ligands.

Another embodiment of this invention is directed to a method of treating Alzheimer's disease, comprising administering an effective amount of one or more compounds of Group A or B, in combination with an effective amount of one or more agents that upregulate insulin degrading enzyme and/or neprilysin.

Another embodiment of this invention is directed to a method of treating Alzheimer's disease, comprising administering an effective amount of one or more compounds of Group A or B, in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds of Group A or B, in combination with an effective amount of one or more fibrates (for example, clofibrate, Clofibride, Etofibrate, Aluminium Clofibrate).

Another embodiment of this invention is directed to a method of treating Alzheimer's disease, comprising administering an effective amount of one or more compounds of Group A or B, in combination with an effective amount of one or more LXR agonists.

Another embodiment of this invention is directed to a method of treating Alzheimer's disease, comprising administering an effective amount of one or more compounds of Group A or B, in combination with an effective amount of one or more LRP mimics.

Another embodiment of this invention is directed to a method of treating Alzheimer's disease, comprising administering an effective amount of one or more compounds of Group A or B, in combination with an effective amount of one or more 5-HTS receptor antagonists.

Another embodiment of this invention is directed to a method of treating Alzheimer's disease, comprising administering an effective amount of one or more compounds of Group A or B, in combination with an effective amount of one or more nicotinic receptor agonists.

Another embodiment of this invention is directed to a method of treating Alzheimer's disease, comprising administering an effective amount of one or more compounds of Group A or B, in combination with an effective amount of one or more H3 receptor antagonists.

This invention also provides a method of treating Alzheimer's disease, comprising administering an effective amount of one or more compounds of Group A or B, in combination with an effective amount of one or more histone deacetylase inhibitors.

Another embodiment of this invention is directed to a method of treating Alzheimer's disease, comprising administering an effective amount of one or more compounds of Group A or B, in combination with an effective amount of one or more hsp90 inhibitors.

Another embodiment of this invention is directed to a method of treating Alzheimer's disease, comprising administering an effective amount of one or more compounds of Group A or B, in combination with an effective amount of one or more m1 muscarinic receptor agonists.

Another embodiment of this invention is directed to a method of treating Alzheimer's disease, comprising administering an effective amount of one or more compounds of Group A or B, in combination with an effective amount of one or more 5-HT6 receptor antagonists mGluR1 or mGluR5 positive allosteric modulators or agonists Another embodiment of this invention is directed to a method of treating Alzheimer's disease, comprising administering an effective amount of one or more compounds of Group A or B, in combination with an effective amount of one or more mGluR2/3 antagonists.

Another embodiment of this invention is directed to a method of treating Alzheimer's disease, comprising administering an effective amount of one or more compounds of Group A or B, in combination with an effective amount of one or more anti-inflammatory agents that can reduce neuroinflammation.

Another embodiment of this invention is directed to a method of treating Alzheimer's disease, comprising administering an effective amount of one or more compounds of Group A or B, in combination with an effective amount of one or more Prostaglandin EP2 receptor antagonists.

This invention also provides a method of treating Alzheimer's disease, comprising administering an effective amount of one or more compounds of Group A or B, in combination with an effective amount of one or more PAM inhibitors.

This invention also provides a method of treating Alzheimer's disease, comprising administering an effective amount of one or more compounds of Group A or B, in combination with an effective amount of one or more agents that can induce Abeta efflux such as gelsolin.

This invention also provides a method of treating Downs syndrome, comprising administering an effective amount of one or more (e.g., one) compounds of Group A or B to a patient in need of treatment.

This invention also provides a method of treating Downs syndrome, comprising administering an effective amount of a compound of Group A or B to a patient in need of treatment.

This invention also provides a method of treating Downs syndrome, comprising administering an effective amount of one or more (e.g., one) compounds of Group A or B, in combination with an effective amount of one or more cholinesterase inhibitors (such as, for example, ($\pm$)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Downs syndrome, comprising administering an effective amount of a compound of Group A or B, in combination with an effective amount of one or more (e.g., one) cholinesterase inhibitors (such as, for example, ($\pm$)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating mild cognitive impairment, comprising administering an effective amount of one or more (e.g., one) compounds of Group A or B to a patient in need of treatment.

This invention also provides a method of treating glaucoma, comprising administering an effective amount of one or more (e.g., one) compounds of Group A or B to a patient in need of treatment.

This invention also provides a method of treating cerebral amyloid angiopathy, comprising administering an effective amount of one or more (e.g., one) compounds of Group A or B to a patient in need of treatment.

This invention also provides a method of treating stroke, comprising administering an effective amount of one or more (e.g., one) compounds of Group A or B to a patient in need of treatment.

This invention also provides a method of treating dementia, comprising administering an effective amount of one or more (e.g., one) compounds of Group A or B to a patient in need of treatment.

This invention also provides a method of treating microgliosis, comprising administering an effective amount of one or more (e.g., one) compounds of Group A or B to a patient in need of treatment.

This invention also provides a method of treating brain inflammation, comprising administering an effective amount of one or more (e.g., one) compounds of Group A or B to a patient in need of treatment.

This invention also provides a method of treating olfactory function loss, comprising administering an effective amount of one or more (e.g., one) compounds of Group A or B to a patient in need of treatment.

This invention also provides combinations (i.e., pharmaceutical compositions) comprising an effective amount of one or more (e.g., one) compounds of Group A or B, in combination with an effective amount of one or more compounds selected from the group consisting of cholinesterase inhibitors (such as, for example, ($\pm$)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), A$\beta$ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of a compound of Group A or B in a pharmaceutically acceptable carrier, and another container (i.e., a second container) comprises an effective amount of another pharmaceutically active ingredient (as described above), the combined quantities of the compound of Group A or B and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment of this invention is directed to a compound of Group A or B in isolated form.

Another embodiment of this invention is directed to a compound of Group A or B in pure form.

Another embodiment of this invention is directed to a compound of Group A or B in pure and isolated form.

Another embodiment is directed to a pharmaceutical composition comprising an effective amount of one or more (e.g., one) compounds of Group A or B, and a pharmaceutically acceptable carrier.

Another embodiment is directed to a pharmaceutical composition comprising an effective amount of a pharmaceutically acceptable salt of one or more (e.g., one) compounds of Group A or B, and a pharmaceutically acceptable carrier.

Another embodiment is directed to a pharmaceutical composition comprising an effective amount of a pharmaceutically acceptable ester of one or more (e.g., one) compounds of Group A or B, and a pharmaceutically acceptable carrier.

Another embodiment is directed to a pharmaceutical composition comprising an effective amount of a solvate of one or more (e.g., one) compounds of Group A or B, and a pharmaceutically acceptable carrier.

Another embodiment of this invention is directed to a pharmaceutical composition comprising an effective amount of one or more (e.g., one) compounds of Group A or B, and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g., one) compounds of Group A or B, and effective amount of one or more BACE inhibitors, and a pharmaceutically acceptable carrier.

Another embodiment of this invention is directed to a pharmaceutical composition comprising an effective amount of one or more (e.g., one) compounds of Group A or B, and an effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds of Group A or B, and effective amount of one or more muscarinic antagonists (e.g., $m_1$ agonists or $m_2$ antagonists), and a pharmaceutically acceptable carrier.

Another embodiment of this invention is directed to a pharmaceutical composition comprising an effective amount of one or more (e.g., one) compounds of Group A or B, and effective amount of Exelon (rivastigmine), and a pharmaceutically acceptable carrier.

Another embodiment of this invention is directed to a pharmaceutical composition comprising an effective amount of one or more (e.g., one) compounds of Group A or B, and effective amount of Cognex (tacrine), and a pharmaceutically acceptable carrier.

Another embodiment of this invention is directed to a pharmaceutical composition comprising an effective amount of one or more (e.g., one) compounds of Group A or B, and effective amount of a Tau kinase inhibitor, and a pharmaceutically acceptable carrier.

Another embodiment of this invention is directed to a pharmaceutical composition comprising an effective amount of one or more (e.g., one) compounds of Group A or B, and effective amount of one or more Tau kinase inhibitor (e.g., GSK3beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds of Group A or B, and effective amount of one anti-Abeta vaccine (active immunization), and a pharmaceutically acceptable carrier.

Another embodiment of this invention is directed to a pharmaceutical composition comprising an effective amount of one or more (e.g., one) compounds of Group A or B, and effective amount of one or more APP ligands, and a pharmaceutically acceptable carrier.

Another embodiment of this invention is directed to a pharmaceutical composition comprising an effective amount of one or more (e.g., one) compounds of Group A or B, and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds of Group A or B, and effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds of Group A or B, and effective amount of one or more fibrates (for example, clofibrate, Clofibride, Etofibrate, Aluminium Clofibrate), and a pharmaceutically acceptable carrier.

Another embodiment of this invention is directed to a pharmaceutical composition comprising an effective amount of one or more (e.g., one) compounds of Group A or B, and effective amount of one or more LXR agonists, and a pharmaceutically acceptable carrier.

Another embodiment of this invention is directed to a pharmaceutical composition comprising an effective amount of one or more (e.g., one) compounds of Group A or B, and effective amount of one or more LRP mimics, and a pharmaceutically acceptable carrier.

Another embodiment of this invention is directed to a pharmaceutical composition comprising an effective amount of one or more (e.g., one) compounds of Group A or B, and effective amount of one or more 5-HT6 receptor antagonists, and a pharmaceutically acceptable carrier.

Another embodiment of this invention is directed to a pharmaceutical composition comprising an effective amount of one or more (e.g., one) compounds of Group A or B, and effective amount of one or more nicotinic receptor agonists, and a pharmaceutically acceptable carrier.

Another embodiment of this invention is directed to a pharmaceutical composition comprising an effective amount of one or more (e.g., one) compounds of Group A or B, and effective amount of one or more H3 receptor antagonists, and a pharmaceutically acceptable carrier.

Another embodiment of this invention is directed to a pharmaceutical composition comprising an effective amount of one or more (e.g., one) compounds of Group A or B, and effective amount of one or more histone deacetylase inhibitors, and a pharmaceutically acceptable carrier.

Another embodiment of this invention is directed to a pharmaceutical composition comprising an effective amount of one or more (e.g., one) compounds of Group A or B, and effective amount of one or more hsp90 inhibitors, and a pharmaceutically acceptable carrier.

Another embodiment of this invention is directed to a pharmaceutical composition comprising an effective amount of one or more (e.g., one) compounds of Group A or B, and effective amount of one or more m1 muscarinic receptor agonists, and a pharmaceutically acceptable carrier.

Another embodiment of this invention is directed to a pharmaceutical composition comprising an effective amount of one or more (e.g., one) compounds of Group A or B, and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds of Group A or B, and effective amount of one or more one mGluR2/3 antagonists, and a pharmaceutically acceptable carrier.

Another embodiment of this invention is directed to a pharmaceutical composition comprising an effective amount of one or more (e.g., one) compounds of Group A or B, and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds of Group A or B, and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds of Group A or B, and effective amount of one or more PAI-1 inhibitors, and a pharmaceutically acceptable carrier.

Another embodiment of this invention is directed to a pharmaceutical composition comprising an effective amount of one or more (e.g., one) compounds of Group A or B, and effective amount of one or more agents that can induce Abeta efflux such as gelsolin, and a pharmaceutically acceptable carrier.

The compounds of Group A or B can be useful as gamma secretase modulators and can be useful in the treatment and prevention of diseases such as, for example, central nervous system disorders (such as Alzheimers disease and Downs Syndrome), and treating mild cognitive impairment, glaucoma, cerebral amyloid angiopathy, stroke, dementia, microgliosis, brain inflammation, and olfactory function loss.

Thus, another embodiment of this invention is directed to a method for modulating (including inhibiting, antagonizing and the like) gamma-secretase comprising administering an effective (i.e., therapeutically effective) amount of one or more (e.g., one) compounds of Group A or B to a patient in need of such treatment.

Another embodiment of this invention is directed to a method for modulating (including inhibiting, antagonizing and the like) gamma-secretase, comprising administering an effective (i.e., therapeutically effective) amount of a compound of Group A or B to a patient in need of treatment.

Another embodiment of this invention is directed to a method of treating one or more neurodegenerative diseases, comprising administering an effective (i.e., therapeutically effective) amount of one or more (e.g., one) compounds of Group A or B to a patient in need of treatment.

Another embodiment of this invention is directed to a method of treating one or more neurodegenerative diseases, comprising administering an effective (i.e., therapeutically effective) amount of a compound of Group A or B to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds of Group A or B to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound of Group A or B to a patient in need of treatment.

Another embodiment of this invention is directed to a method of treating Alzheimer's disease, comprising administering an effective (i.e., therapeutically effective) amount of one or more (e.g., one) compounds of Group A or B to a patient in need of treatment.

Another embodiment of this invention is directed to a method of treating Alzheimer's disease, comprising administering an effective (i.e., therapeutically effective) amount of a compound of Group A or B to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds of Group A or B to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound of Group A or B to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of Group A or B, and the administration of one or more (e.g., one) other pharmaceutical active ingredients (e.g., drugs). The compounds of Group A or B, and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein the compounds of Group A or B are used in combination with an effective amount of one or more other pharmaceutically active ingredients selected from the group consisting of: BACE inhibitors (beta secretase inhibitors); muscarinic antagonists (e.g., $m_1$ agonists or $m_2$ antagonists); cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of Group A or B, and the administration of one or more (e.g., one) other pharmaceutical active ingredients (e.g., drugs). The compounds of Group A or B, and the other drugs can be administered separately (i.e., each is in its own separate dosage form), or the compounds of Group A or B can be combined with the other drugs in the same dosage form.

Thus, other embodiments of this invention are directed to any one of the methods of treatment, or methods of inhibiting, described herein, wherein the compounds of Group A or B are used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyryl-chlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics: nicotinic receptor agonists: H3 receptor antagonists; histone deacetylase inhibitors; hsp90 inhibitors; m1 muscarinic receptor agonists; 5-HTS receptor antagonists: mGluR1; mGluR5; positive allosteric modulators or agonists: mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Other embodiments of this invention are directed to any one of the methods of treatment, or methods of inhibiting, described herein, wherein the compounds of Group A or B are used in combination with an effective amount of one or more other pharmaceutically active ingredients selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyryl-chlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; GABA$_A$ inverse agonists; inhibitors of amyloid aggregation; glycogen synthase kinase beta inhibitors; promoters of alpha secretase activity; PDE-10 inhibitors; and cholesterol absorption inhibitors (e.g., ezetimibe).

Other embodiments of this invention are directed to any one of the methods of treatment, or methods of inhibiting, described herein, wherein the compounds of Group A or B are used in combination with an effective amount of one or more other pharmaceutically active ingredients selected from the group consisting of: Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe): fibrates (such as, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Another embodiment of this invention is directed to a method of treating Alzheimer's disease, comprising administering an effective (i.e., therapeutically effective) amount of one or more (e.g., one) compounds of Group A or B, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of a compound of Group A or B, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of one or more (e.g., one) compounds of Group A or B selected from the group consisting of in combination with an effective (i.e., therapeutically effective) amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective (i.e., therapeutically effective) amount of one or more (e.g., one) compounds of Group A or B, in combination with an effective (i.e., therapeutically effective) amount of one or more BACE inhibitors.

Another embodiment of this invention is directed to a method of treating Alzheimer's disease, comprising administering an effective (i.e., therapeutically effective) amount of a compound of Group A or B, in combination with an effective (i.e., therapeutically effective) amount of one or more BACE inhibitors.

Another embodiment of this invention is directed to a method of treating Downs syndrome, comprising administering an effective (i.e., therapeutically effective) amount of one or more (e.g., one) compounds of Group A or B to a patient in need of treatment.

Another embodiment of this invention is directed to a method of treating Downs syndrome, comprising administering an effective (i.e., therapeutically effective) amount of a compound of Group A or B, to a patient in need of treatment.

Another embodiment of this invention is directed to a method of treating Downs syndrome, comprising administering an effective (i.e., therapeutically effective) amount of one or more (e.g., one) compounds of Group A or B, in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective (i.e., therapeutically effective) amount of a compound of Group A or B, in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to combinations (i.e., pharmaceutical compositions) comprising an effective (i.e., therapeutically effective) amount of one or more (e.g., one) compounds of Group A or B in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of one or more (e.g., one) compounds of Group A or B in a pharmaceutically acceptable carrier, and another container (i.e., a second container) comprises an effective amount of another pharmaceutically active ingredient (as described above), the combined quantities of the compounds of Group A or B and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

This invention also provides a kit comprising, in separate containers, in a single package, pharmaceutical compositions for use in combination, wherein one container comprises an effective amount of a compound selected from the group consisting of the compounds of Group A or B in a pharmaceutically acceptable carrier, and another container (i.e., a second container) comprises an effective amount of another pharmaceutically active ingredient (as described above), the combined quantities of the compound of Group A or B and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Examples of cholinesterase inhibitors are tacrine, donepezil, rivastigmine, galantamine, pyridostigmine and neostigmine, with tacrine, donepezil, rivastigmine and galantamine being preferred.

Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 24, 2005), US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 12, 2006), US2007/0099898 published May 3, 2007 (see also WO2007/050721 published May 3, 2007), WO2007/053506 published May 10, 2007 (see also US2007/099875 published May 3, 2007). U.S. application Ser. No. 11/759,336 filed Jun. 7, 2007, U.S. Application Ser. No. 60/874,362 filed Dec. 12, 2006, and U.S. Application Ser. No. 60/874,419 filed Dec. 12, 2006, the disclosures of each being incorporated herein by reference thereto.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Group A or B, or a pharmaceutically acceptable salt, solvate, ester or prodrug of said compound and a pharmaceutically acceptable carrier, vehicle or diluent.

Yet another aspect of this invention is a kit comprising an amount of at least one compound of Group A or B, or a pharmaceutically acceptable salt, solvate, ester or prodrug of said compound and an amount of at least one additional agent listed above, wherein the amounts of the two or more ingredients result in desired therapeutic effect.

The invention disclosed herein is exemplified by the following illustrative example which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 7 min-95% CH$_3$CN, 7.5 min-10% CH$_3$CN, 9 min-stop. The observed parent ion is given.

Method Q

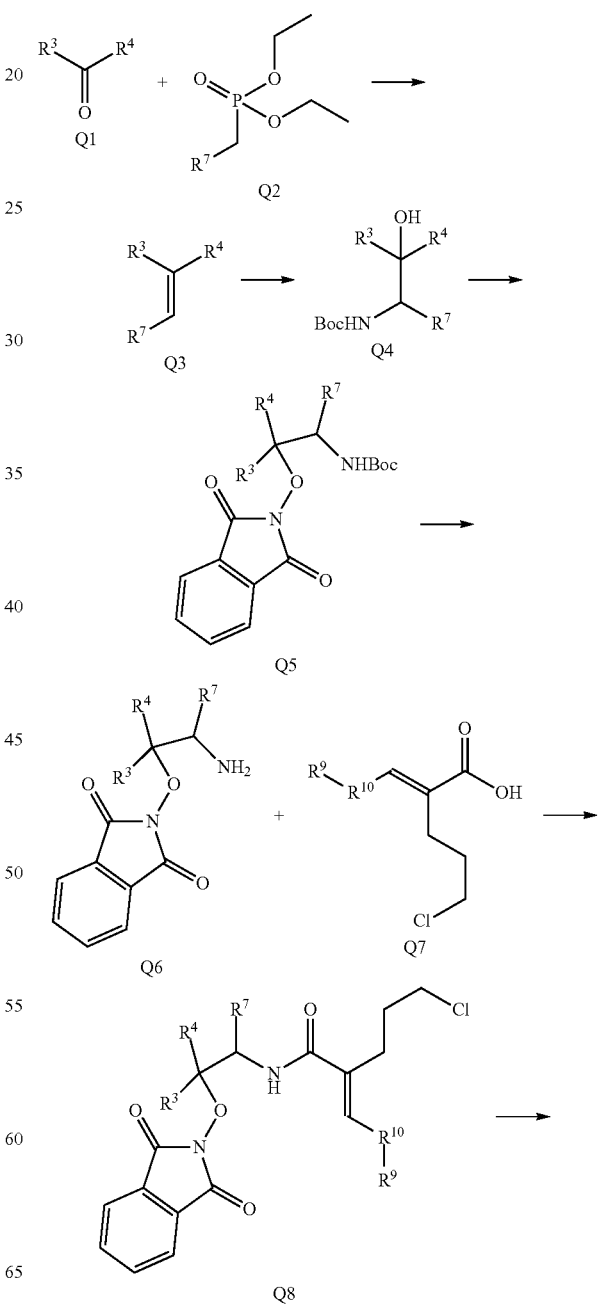

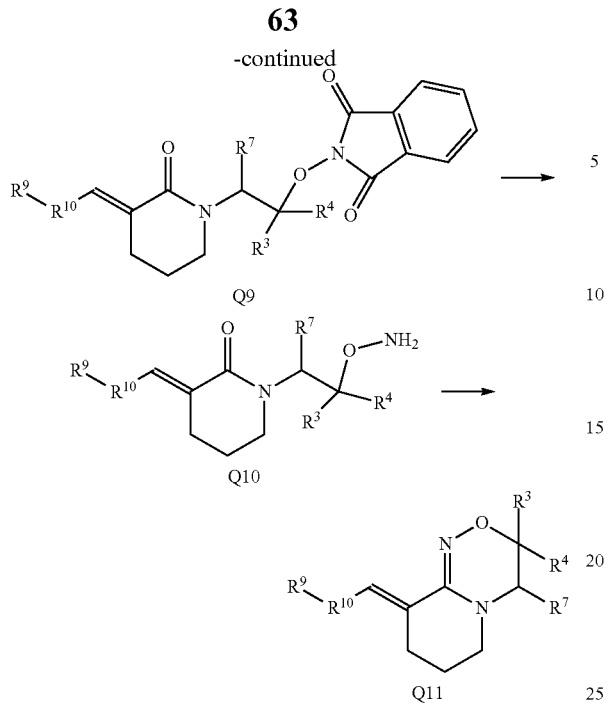

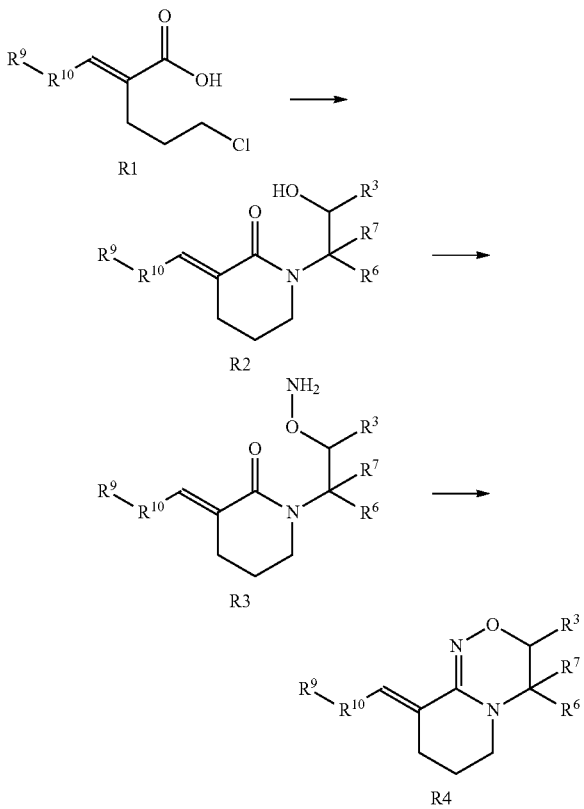

Method Q, Step 6

Compound Q8 (R⁷=4-F-Phenyl, R¹⁰=3-MeO-Phenyl, R⁹=4-(4-Methyl-imidazol-1-yl), R³=R⁴=Me) will be treated with NaH in DMF to give Q9 (R⁷=4-F-Phenyl, R¹⁰=3-MeO-Phenyl, R⁹=4-(4-Methyl-imidazol-1-yl), R³=R⁴=M after workup and purification.

Method Q, Step 7

Compound Q9 (R⁷=4-F-Phenyl, R¹⁰=3-MeO-Phenyl, R⁹=4-(4-Methyl-imidazol-1-yl), R³=R⁴=Me) will be treated with hydrazine in methanol to give compound Q10 (R7=4-F-Phenyl, R¹⁰=3-MeO-Phenyl, R⁹=4-(4-Methyl-imidazol-1-yl), R³=R⁴=Me) after workup and purification.

Method Q, Step 8

Compound Q10 (R⁷=4-F-Phenyl, R¹⁰=3-MeO-Phenyl, R⁹=4-(4-Methyl-imidazol-1-yl), R³=R⁴=Me) will be converted to Q11 (R⁷=4-F-Phenyl, R¹⁰=3-MeO-Phenyl, R⁹=4-(4-Methyl-imidazol-1-yl), R³=R⁴=Me) through refluxing with P₂O₅ in ethanol.

The following compounds will be synthesized using method similar to method Q.

Method R

Method Q, Step 1

Q1 (R³=R⁴=Me) and Q2 (R⁷=4F-Phenyl) will react in THF in the presence of KOtBu to give compound Q3 (R⁷=4-F-Phenyl, R³=R⁴=Me) after work up and purification.

Method Q, Step 2

Q3 (R⁷=4-F-Phenyl, R³=R⁴=Me) will be converted to Q4 (R⁷=4-F-Phenyl, R³=R⁴=Me) using a method similar to L. Barboni and C. Lambertucci; *J. Med. Chem.* 2001, 44, 1576;

To a stirred solution of tert-butyl carbamate (2.32 g, 15.3 mmol) in 2-propanol (20 mL), a solution of NaOH (604 mg) in water (37 mL), tert-butyl hypochlorite (1.73 mL) and (DHQ)₂PHAL (198 mg) in 2-propanol (17.3 mL) will be sequentially added. After stirring at room temperature for 10 min, 4.95 mmol of compound Q3 will be added, followed by K₂OsO₂(OH)₄ (73 mg). After stirring at room temperature for 7 h, the reaction will be worked up by cooling in a ice bath and addition of saturated Na₂SO₃ (49.5 mL). After further stirring for 15 min, the reaction mixture will be extracted with EtOAc, and the organic phase will be washed with brine, dried (Na₂SO₄) and evaporated. The residue will be chromatographed on silica gel (hexanes-EtOAc) to give Q4 (R⁷=4-F-Phenyl, R³=R⁴=Me).

Method Q, Step 3

To a THF solution of Q4 (R⁷=4-F-Phenyl, R³=R⁴=Me) will be added N-hydroxylphthalimide, ADDP and triphenylphosphine. The reaction will be stirred overnight to give compound Q5 (R⁷=4-F-Phenyl, R³=R⁴=Me) after workup and purification.

Method Q, Step 4

Compound Q5 (R⁷=4-F-Phenyl, R³=R⁴=Me) will be treated with TFA in DCM to give compound Q6 (R⁷=4-F-Phenyl, R³=R⁴=Me).

Method Q, Step 5

Compound Q6 will be coupled with Q7 (R⁷=4-F-Phenyl, R¹⁰=3-MeO-Phenyl, R⁹=4-(4-Methyl-imidazol-1-yl), R³=R⁴=Me) using EDCl/TEA/DMF conditions to give Q8 (R⁷=4-F-Phenyl, R¹⁰=3-MeO-Phenyl, R⁹=4-(4-Methyl-imidazol-1-yl), R³=R⁴=Me) after workup and purification.

Method R, Step 1

To a stirring mixture of 2-amino-1-(3,4,5-trifluorophenyl) ethanol (1 mmol), acid R1 (R¹⁰=3-MeO-Phenyl, R⁹=4-(4-Methyl-imidazol-1-yl), 1.0 mmol), HOBT (1.5 mmol) and DIEA (6 mmol) in anhydrous DMF (5 mL) was added EDCl (1.5 mmol). The solution resulted was then stirred overnight at rt. Upon evaporating DMF under high vacuum, the residue was taken up into EtOAc (100 mL) and saturated NaHCO₃ (30 mL). The EtOAc layer was collected and dried over Na₂SO₄. After remove EtOAc, the residue was dissolved in THF (10 mL). To this THF solution was then added NaOMe (2 mmol, 4.2 M in MeOH). The mixture resulted was stirred over night at rt. After which, the THF was removed and residue was partitioned between EtOAc and H$_2$O. The EtOAc layer was collected and dried over Na$_2$SO$_4$. After evaporating EtOAc, the residue was purified through flash chromatography to afford the desired lactam R2 (R$^6$=R$^7$=H, R$^3$=3,4,5-tri-F-Phenyl, R$^{10}$=3-MeO-Phenyl, R$^9$=4-(4-Methyl-imidazol-1-yl)).

$^1$HNMR: δ (ppm) 7.93 (1H, bs), 7.81 (1H, bs), 7.34-7.37 (2H, m), 7.19 (1H, d, J=6.8 Hz), 7.11 (2H, m), 7.04 (bs, 1H), 5.18 (1H, bs), 3.97 (3H, s), 3.94 (1 h, m), 3.60-3.70 (1H, m), 3.50 (1H, m), 3.3-3.4 (1H, m), 2.89 (2H, m), 2.39 (3H, s), 2.14 (2H, m).

Method R, Step 2

The lactam R2 (R$^6$=R$^7$=H, R$^3$=3,4,5-tri-F-Phenyl, R$^{10}$=3-MeO-Phenyl, R$^9$=4-(4-Methyl-imidazol-1-yl)), 0.5 mmol) was mixed with PPh$_3$ (1 mmol) and N-hydroxylphthalimide (1 mmol) in anhydrous THF (5 mL) under N$_2$. The mixture was then cooled to −10 C. DIAD (1 mmol) was then added dropwisely. The mixture was allowed to warm up to rt and stir was continued for overnight, After which, the THF was removed, and the residue was taken up in EtOAc (50 mL). The EtOAc layer was further washed with NaHCO$_3$ (2×30 mL) and then dried over Na$_2$SO$_4$. After removal of the EtOAc, the residue was dissolved in EtOH (10 mL). NH$_2$NH$_2$ (1 mmol) was then added to the solution. After further stirring for overnight, the EtOH was removed and residue was dissolved in CH$_2$Cl$_2$ (50 mL). The CH$_2$Cl$_2$ layer was washed consecutively with H$_2$O and brine, then, dried over Na$_2$SO$_4$. The CH$_2$Cl$_2$ was then removed and the residue was purified through flash chromatography to afford the desired hydroxylamine R3 (R$^6$=R$^7$=H, R$^3$=3,4,5-tri-F-Phenyl, R$^{10}$=3-MeO-Phenyl, R$^9$=4-(4-Methyl-imidazol-1-yl)).

$^1$HNMR, δ (ppm): 7.80 (1H, bs), 7.71 (1H, s), 7.23-7.25 (1H, m), 7.01-7.1 (3H, m), 6.92 (1H, s), 5.45 (2H, b), 4.90 (1H, m), 3.85 (3H, s), 3.80 (1H, m), 3.5-3.6 (1H, m), 3.26-3.38 (2H, m), 2.80 (2H, m), 2.29 (3H, s), 1.80-1.90 (2H, m).

Method R, Step 3

The hydroxylamine R3 (R$^6$=R$^7$=H, R$^3$=3,4,5-tri-F-Phenyl, R$^{10}$=3-MeO Phenyl, R$^9$=4-(4-Methyl-imidazol-1-yl)), 10 mg) was dissolved in EtOH (1 mL). This solution was then added to a premixed mixture of P$_2$O$_5$ (30 mg) and EtOH (1 mL). The resulted mixture was then stirred at 80° C. overnight. After the reaction mixture was cooled down, it was diluted with CH$_2$Cl$_2$ (50 mL) and H2O. Excess K$_2$CO$_3$ was then added to adjust the pH to ~9-10. The organic layer was then collected and dried over Na$_2$SO$_4$. After evaporating the CH$_2$Cl$_2$, the residue was purified with flash chromatography to afford the desired final product R4 (R$^6$=R$^7$=H, R$^3$=3,4,5-tri-F-Phenyl, R$^{10}$=3-MeO-Phenyl, R$^9$=4-(4-Methyl-imidazol-1-yl)). LCMS, retention time: 2.67 min, MS observed, 469.3.

$^1$HNMR, δ (ppm): 7.68 (1H, s), 7.47 (1H, bs), 7.23 (1H, d, J=10 Hz), 7.03 (2H, m), 6.90-6.96 (3H, m), 4.70 (1H, dd, J=8.4 and 3.2 Hz), 3.83 (3H, s), 3.47 (4H, m), 2.73 (2H, m), 2.28 (3H, s), 1.91 (2H, m).

Method T

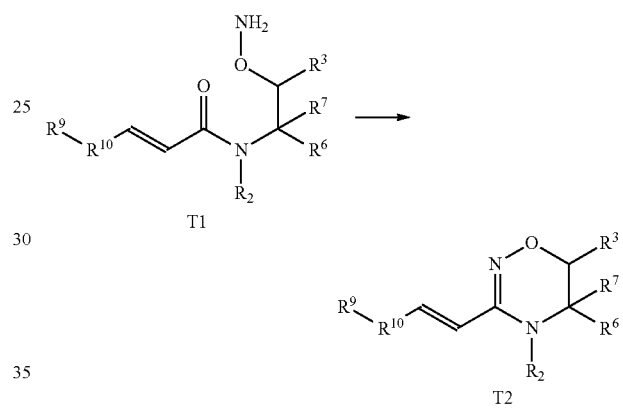

Compound T1 (R$^2$=Me, R$^3$=R$^6$=H, R$^7$=p-F-phenyl, R$^{10}$=3-MeO-Phenyl, R$^9$4-(4-Methyl-imidazol-1-yl)), synthesized using a method similar to method R, will be converted to T2 (R$^2$=Me, R$^3$=R$^6$=H, R$^7$=p-F-phenyl, R$^{10}$=3-MeO-Phenyl, R$^9$=4-(4-Methyl-imidazol-1-yl)), using a method similar to method R.

The following compounds were synthesized using a method similar to that listed in the last column:

| # | Compound | Rt (min) | Obs. Mass | Synthetic Method |
|---|---|---|---|---|
| 201 | racemic | 2.3 | 463.25 | R |

-continued

| # | Compound | Rt (min) | Obs. Mass | Synthetic Method |
|---|---|---|---|---|
| 202 | racemic | 2.4 | 431.24 | R |
| 203 | enantiomer I | 2.8 | 469.26 | R |
| 206 | (R) | 2.6 | 451.25 | R |
| 207 | enantiomer I | 2.7 | 475.26 | R |
| 208 | enantiomer I | 3.1 | 433.24 | R |

-continued

| # | Compound | Rt (min) | Obs. Mass | Synthetic Method |
|---|---|---|---|---|
| 209 | (R) | 2.5 | 447.25 | R |
| 210 | racemic | 3.2 | 625.34 | R |
| 211 | enantiomer II | 2.7 | 475.26 | R |
| 212 | racemic | 2.7 | 475.26 | R |

| # | Compound | Rt (min) | Obs. Mass | Synthetic Method |
|---|---|---|---|---|
| 213 | 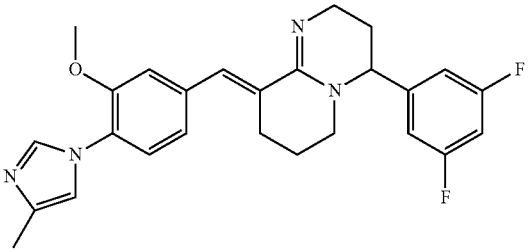 [SMILES: COc1cc(/C=C2\CCCN3C2=NCCC3c2cc(F)cc(F)c2)ccc1-n1cnc(C)c1] racemic | 2.4 | 449.25 | R |
| 214 | 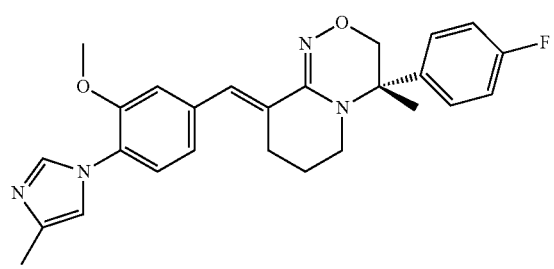 [SMILES: COc1cc(/C=C2\CCCN3C2=NOC[C@]3(C)c2ccc(F)cc2)ccc1-n1cnc(C)c1] (S) | 2.5 | 447.25 | R |
| 215 | 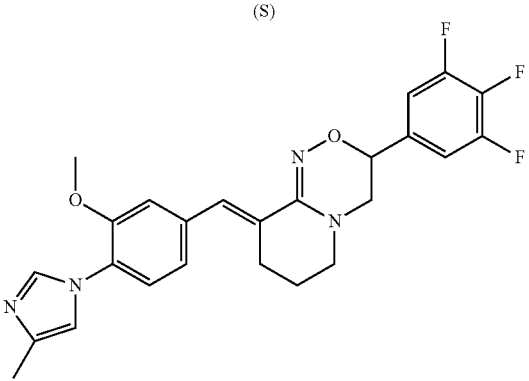 racemic | 2.67 | 469.3 | R |
| 218 | 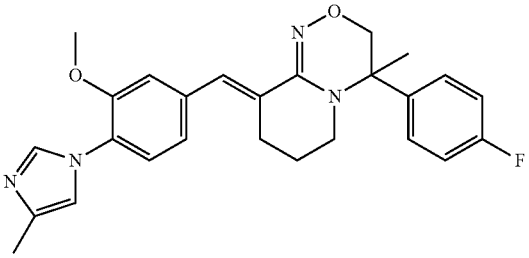 [SMILES: COc1cc(/C=C2\CCCN3C2=NOCC3(C)c2ccc(F)cc2)ccc1-n1cnc(C)c1] racemic | 2.5 | 447.25 | R |
| 220 | 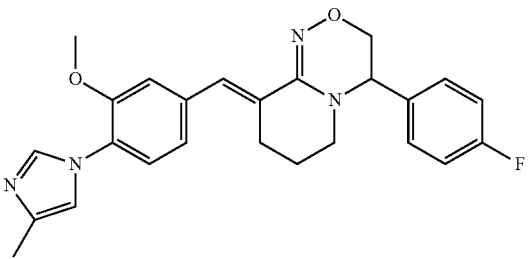 [SMILES: COc1cc(/C=C2\CCCN3C2=NOCC3c2ccc(F)cc2)ccc1-n1cnc(C)c1] racemic | 2.6 | 433.24 | R |

-continued
| # | Compound | Rt (min) | Obs. Mass | Synthetic Method |
|---|---|---|---|---|
| 221 | 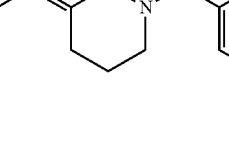 racemic | | | R |
| 222 | 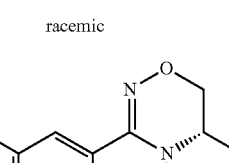 (S) | 2.3 | 415.23 | R |
| 226 | 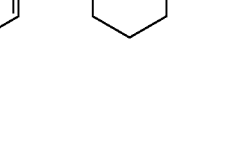 racemic | | | R |
| 227 | 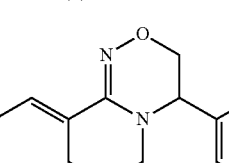 (S) | 2.6 | 451.25 | R |
| 229 | 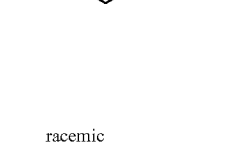 racemic | | 469.26 | R |

-continued

| # | Compound | Rt (min) | Obs. Mass | Synthetic Method |
|---|---|---|---|---|
| 231 | enantiomer II | 3.1 | 433.24 | R |
| 233 | enantiomer II | 2.8 | 469.26 | R |

The following compounds will be synthesized using a method similar to that listed in the last column:

| # | Compound | Synthetic Method |
|---|---|---|
| 245 | | Q |
| 246 | | Q |

-continued

| # | Compound | Synthetic Method |
|---|----------|------------------|
| 247 | | Q |
| 248 | | Q |
| 249 | | Q |
| 250 | | Q |
| 251 | | Q |

-continued

| # | Compound | Synthetic Method |
|---|----------|------------------|
| 252 | 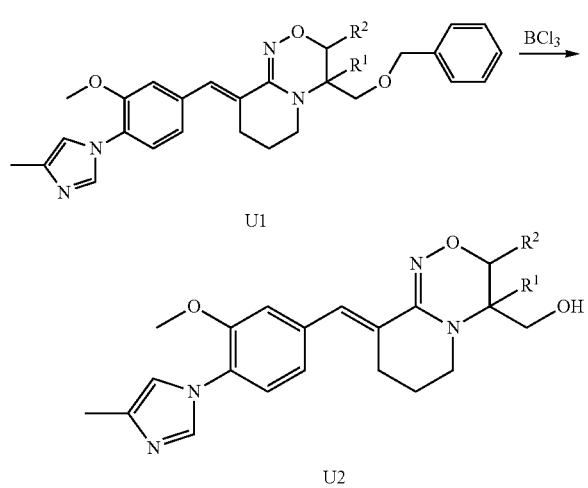 | Q |

Method U

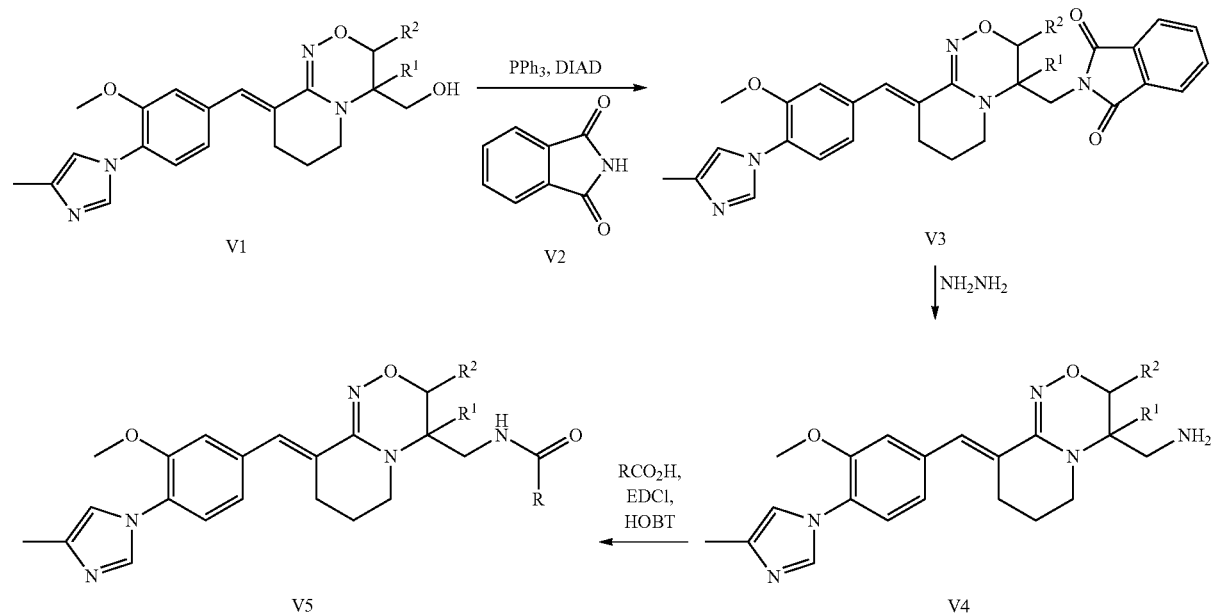

A solution of U1 (20 mg, $R^1=R^2=H$), which was synthesized following similar procedure as described for Method R, in $CH_2Cl_2$ was cooled to $-10°$ C. To this solution was then added $BCl_3$ (0.15 mL, 1M in hexanes). The resulted mixture was then allowed to warm up to room temperature. Stirring continued at room temperature for 2 hours before the reaction was quenched by addition of water. The organic layer was then separated and discarded. The water layer was basified and extracted with $CH_2Cl_2$ (3×20 mL). The combined organic layer was dried over $Na_2SO_4$. After removal of the volatile, the residue was purified by flash chromatography to afford the desired target U2 ($R^1=R^2=H$). LCMS: observed 369.2 ($M^++1$). $^1$H NMR (CDCl$_3$, 400 MHz, δ): 7.82 (1H, s), 7.54 (1H, s), 7.33 (1H, d, J=7.4 Hz), 7.04-7.08 (3H, m), 4.44 (1H, d, J=11.5 Hz), 3.95-4.08 (2H, m), 3.93 (3H, s), 3.84 (1H, d, J=12 Hz), 3.55 (1H, m), 3.44 (1H, m), 3.28 (1H, m), 2.79-2.94 (2H, m), 2.42 (3H, s), 2.02 (2H, m).

Method V

Method V, Step 1:

A mixture of V1 (1 g, 2.72 mmol, $R^1=R^2=H$), which was synthesized following method U, V2 (919 mg, 6.25 mmol) and $PPh_3$ (1.64 g, 6.26 mmol) was dissolved in anhydrous THF (20 mL) and was cooled to −10° C. under $N_2$. DIAD (1.26 g, 6.24 mmol) was then added to the solution. The mixture resulted was allowed to warm up to room temperature and stir continued until analysis suggested full consumption of the starting alcohol. Reaction was then quenched by dilution with EtOAc (100 mL) and aqueous $NaHCO_3$ (30 mL). The EtOAc layer was the further washed with $H_2O$ (30 mL) and brine (25 mL). After which the EtOAc layer was dried over $Na_2SO_4$, and removal of all volatile then afforded the crude product. Purification of the crude by flash chromatography then afforded the desired product V3 ($R^1=R^2=H$). LCMS: observed 498 ($M^++1$). $^1H$ NMR ($CDCl_3$, 400 MHz, δ): 7.85-7.88 (2H, m), 7.69-7.75 (3H, m), 7.39 (1H, s), 7.20 (1H, d, J=7.7 Hz), 6.87-7.00 (3H, m), 7.25 91H, d, J=10.7 Hz), 4.10-4.15 (1H, m), 3.89 (1H, dd, J=10 and 4 Hz), 3.82 (3H, s), 3.66 (1H, dd, J=11.3 and 2.5 Hz), 3.54-3.61 (1H, m), 3.49-3.52 (1H, m), 3.14-3.19 (2H, m), 2.66-2.81 (2H, m), 2.29 (3H, s), 1.85-1.93 (2H, m).

Method V, Step 2:

To a solution of V3 (1 g, $R^1=R^2=H$) in EtOH (30 mL) was added hydrazine monohydrate (0.3 g). The mixture was stirred at room temperature for 48 h. After which, the solution was heated at 100 C with mW heating for 5 minutes. The reaction mixture was then allowed to cool to room temperature and filtered. The filtrate was concentrated in vaccum and crude product of V4 (R1=R2=H) was isolated. LCMS: observed 368 ($M^+1$).

Method V, Step 3:

Amine V4 was dissolved in MeCN/THF (10 mg/1 mL, 3/1). To this solution was then added polymer bound EDC (3 equiv.) HOBT (1.5 equiv) and $RCO_2H$ (1.5 equiv, 1M solution in DMF) was then added. The suspension was then shaken at room temperature for 24 hours. After which polymer bound isocyanate (57 mg) and polymer bound trisamine (42 mg) and additional MeCN (0.5 mL) was added. The mixture was further shaken for 24 hours. The resin was then filtered. The filtrate was concentrated under vaccum to produce a library of amides V5 ($R^1=R^2=H$).

Method W

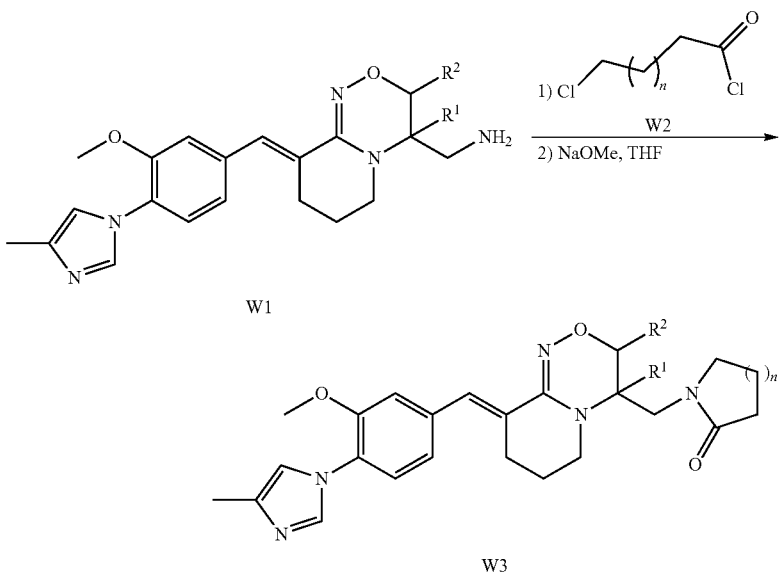

W1

W3

W1 (50 mg, $R^1=R^2=H$), which was synthesized following similar procedure as described for Method V, in dry $CH_2Cl_2$ was treated with $Et_3N$ and W2 (1.5 equiv, n=1). Stir until no starting material left. Aqueous workup then afforded a crude mixture. This crude mixture was then dissolved in dry THF and NaOMe (2 equiv) was added. The resulted mixture was further stirred until analysis suggested no uncyclized intermediate left. The volatile was then removed and the residue was partition in $CH_2Cl_2$ and water. The $CH_2Cl_2$ was then removed and the residue was purified to afford the desired product W3 ($R^1=R^2=H$, n=1) as its formate. LCMS: observed 436.2 ($M^++1$). $^1H$ NMR ($CDCl_3$, 400 MHz, δ): 7.76 (1H, s), 7.42 (1H, bs), 7.21 (1H, d, J=7.4 Hz), 6.91-6.99 (3H, m), 4.08 (1H, d, J=11.7 Hz), 3.83 (3H, s), 3.37-3.69 (7H, m), 3.16-3.22 (1H, m), 2.64-2.80 (2H, m), 2.40 (2H, t, J=8.6 Hz), 2.30 (3H, s), 2.02-2.10 (2H, m), 1.83-1.90 (2H, m).

Method X

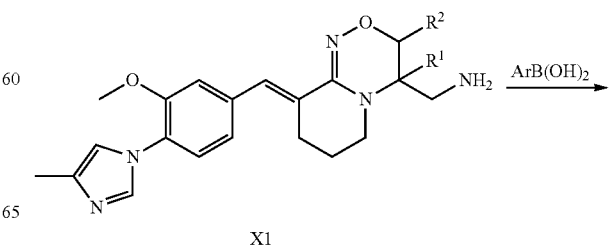

X1

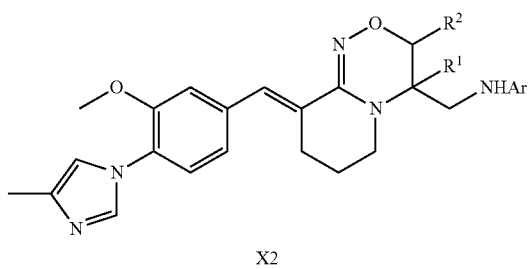

X2

Amine X1 (50 mg, $R^1=R^2=H$), which was synthesized following similar procedure as described for Method V, Aryl boronic acid (30 mg, Ar=Phenyl) and Cu(OAc)$_2$ (15 mg) was mixed with CH$_2$Cl$_2$ (1 mL). Et$_3$N (0.1 mL) was then added and the mixture was stirred overnight. The mixture was then filtered through celite and after removal of all volatile, the resulted residue was purified by HPLC to afford X2 ($R^1=R^2=H$, Ar=Phenyl) as the TFA salt. LCMS: observed 444 (M$^+$+1). $^1$H NMR (CD$_3$OD, 400 MHz, δ): 9.18 (1H, s), 7.62 (1H, d, J=8.1 Hz), 7.60 (1H, s), 7.32 (2H, m), 7.22 (1H, d, J=8.4 Hz), 7.15 (2H, t, J=8.7 Hz), 6.71 (2H, d, J=7.6 Hz), 6.65 (1H, t, J=7.6 Hz), 4.56 (1H, d, J=11.0 Hz), 4.0-4.02 (1H, m), 3.96 (3H, s), 3.76-3.85 (2H, m), 3.47-3.64 (3H, m), 2.76-2.90 (2H, m), 2.43 (3H, s), 1.85-2.05 (2H, m).

Method Y

Method Y, Step 1:

Oxalyl chloride (6.79 mmol) was dissolved in CH$_2$Cl$_2$ (15 mL) and cooled to −78 C. DMSO (530 mg) was then added to the solution. After the mixture was stirred for another 30 minutes, a suspension of Y1 (1 g, $R^1=R^2=R^3=H$), which was synthesized following similar procedure as described for Method U, in CH$_2$Cl$_2$ (10 mL) was then added. The resulted mixture was then allowed to stir at this temperature for half an hour before Et$_3$N (690 mg) was added. The mixture was allowed to warm up to room temperature. This aldehyde intermediate Y2 ($R^1=R^2=R^3=H$) was not further purified.

Method Y, Step 2:

To the above obtained solution (2 mL) was added HNR$^4$R$^5$ (2 equiv. $R^4=R^5=$Et) and excess triacetylborohydride. The mixture was then stirred at room temperature overnight. After which, the mixture was diluted with CH$_2$Cl$_2$ and the organic layer was then washed with aqueous NaHCO$_3$. The organic layer was collected and evaporated to dryness. Residue was then purified through reverse phase HPLC to afford the desired product Y3 ($R^1=R^2=R^3=H$, $R^4=R^5=$Et) as its formate. LCMS: observed 424, $^1$H NMR (CDCl$_3$, 400 MHz, δ): 7.84 (1H, s), 7.41 (1H, s), 7.21 (1H, d, J=7.6 Hz), 6.91-6.97 (3H, m), 4.32 (1H, d, J=10.4 Hz), 3.83 (3H, s), 3.65 (1H, d, J=11 Hz), 3.43-3.52 (2H, m), 3.14-3.20 (1H, m), 2.93-2.98 (1H, m), 2.63-2.86 (7H, m), 2.31 (3H, s), 1.88 (2H, m), 1.15 (6H, t, J=6.8 Hz).

Method Z

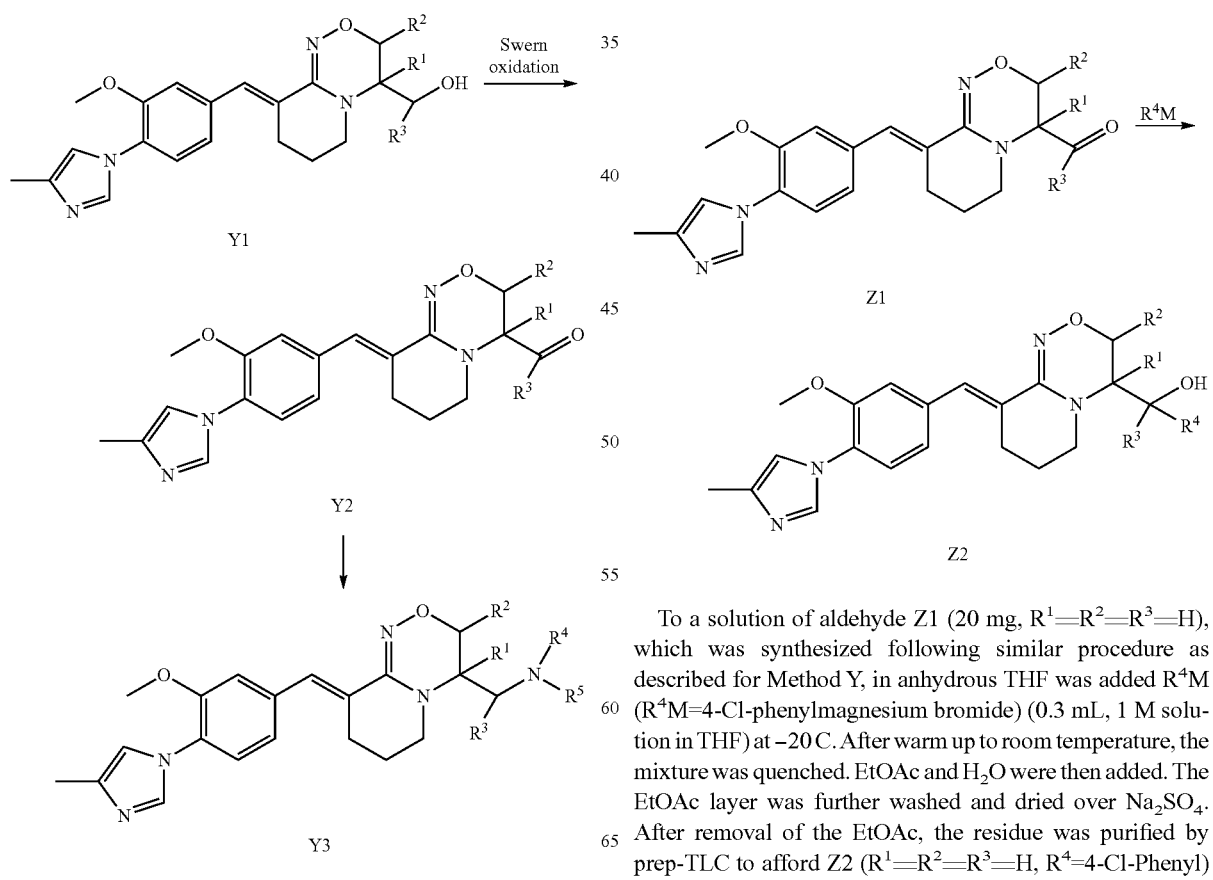

To a solution of aldehyde Z1 (20 mg, $R^1=R^2=R^3=H$), which was synthesized following similar procedure as described for Method Y, in anhydrous THF was added R$^4$M (R$^4$M=4-Cl-phenylmagnesium bromide) (0.3 mL, 1 M solution in THF) at −20 C. After warm up to room temperature, the mixture was quenched. EtOAc and H$_2$O were then added. The EtOAc layer was further washed and dried over Na$_2$SO$_4$. After removal of the EtOAc, the residue was purified by prep-TLC to afford Z2 ($R^1=R^2=R^3=H$, R$^4$=4-Cl-Phenyl) as two diastereomers. LCMS: observed 479.3 (M+1).

Method Aa

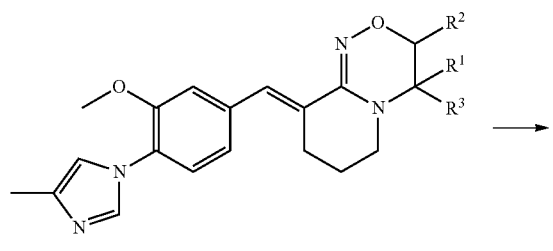

Aa1

To a mixture of Aa1 (20 mg, $R^1=R^2=H$, $R^3$=3,4,5-trifluorophenyl), which was obtained through method R, and N-iodosuccinimide (2 equiv) was added $CF_3SO_3H$ (0.5 mL) at 0 C. The mixture was stirred at this temperature for 10 minutes. The mixture was then poured into iced $Na_2S_2O_3$ solution. EtOAc was added to extract the product out. After purification, Aa2 ($R^1=R^2=H$, $R^3$=3,4,5-trifluorophenyl) was obtained. LCMS: observed, 595. $^1$H NMR (CDCl$_3$, 400 MHz, δ): 8.00 (1H, br), 7.74 (1H, s), 7.31 (1H, s), 6.92-7.01 (4H, m), 4.26 (1H, m), 4.08 (2H, m), 3.83 (3H, s), 3.07-3.16 (2H, m), 2.55 (2H, m), 2.39 (3H, s), 1.88 (2H, m).

Method Ab

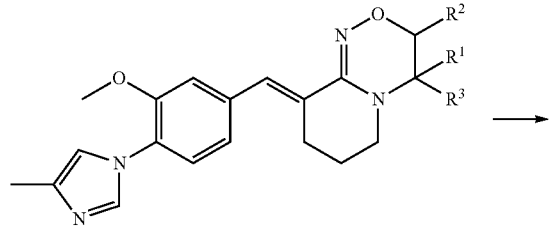

To a solution of Ab1 ($R^1=R^2=H$, $R^3$=3,4,5-trifluorophenyl) (45 mg, 0.096 mmol), which was synthesized following similar procedure as described for Method R, in 1.5 mL MeOH was added $C/Pd(OH)_2$ (10%, 50 mg), 2 drops of water and stirred under $H_2$ (1 atmosphere) for 30 minutes at room temperature. The reaction mixture was filtered through celite and the celite was washed with MeOH (5 mL×3). Combine all filtrate and remove solvent to yield Ab2 (R1=R2=H, R3=3,4,5-trifluorophenyl, 25 mg, 56% yield).

MS (M+H)=471.5; $^1$H NMR (400 MHz, CDCl$_3$) δ 1.53 to 1.60 (m, 1H), 1.65 to 1.79 (m, 2H), 1.87 to 1.95 (m, 1H), 2.27 (s, 3H), 2.78 to 2.84 (m, 1H), 2.87 to 2.94 (m, 2H), 2.98 to 3.03 (m, 1H), 3.28 to 3.33 (m, 1H), 3.81 (s, 3H), 3.84 to 3.88 (m, 1H), 4.02 to 4.06 (m, 1H), 4.15 to 4.17 (m, 1H), 6.85 to 6.93 (m, 4H), 7.14 to 7.17 (d, J=8.23 Hz, 1H), 7.64 (s, 1H).

Method Ac

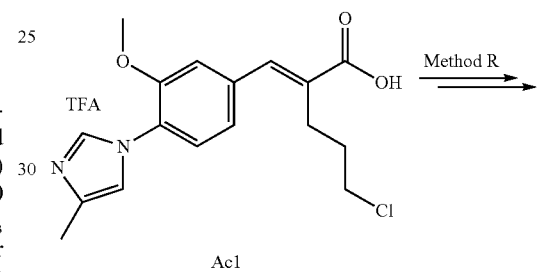

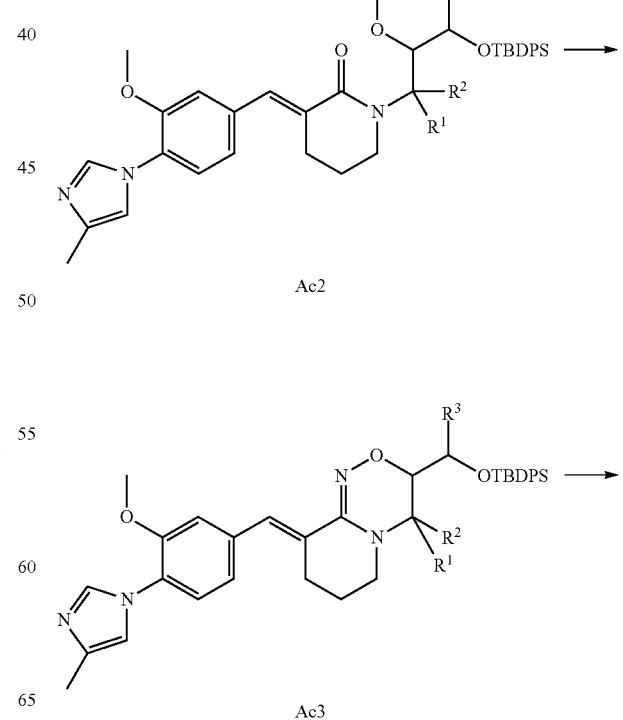

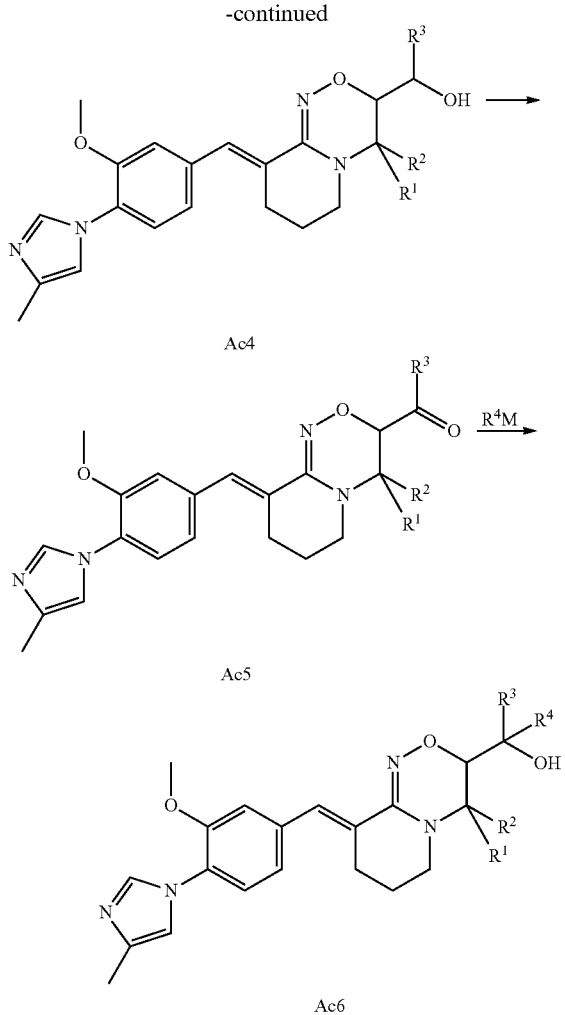

Ac4

Ac5

Ac6

Method Ac, Step 1:

Ac2 ($R^1$=$R^2$=$R^3$=H) was prepared from Ac1 using analogous conditions described in Method R.

Method Ac, Step 2:

Trimethylsilyl trifluoromethane sulfonate (2.37 mL) was added slowly to a stirred solution of Ac2 (3.9 g, $R^1$=$R^2$=$R^3$=H) and TEA (1.83 mL) in 9.5 mL anhydrous DCE at −30° C. under nitrogen atmosphere. The reaction mixture was stirred for 30 min after removal of dry ice bath, and at 60° C. overnight. The reaction mixture was allowed to cool to r.t., quenched with mixture of ice and aqueous sodium bicarbonate, and extracted with DCM. The organic phase was dried over anhydrous sodium sulfate, filtered and evaporated. Residue was purified on a silica gel column with Hexane and EtOAc to give 2.5 g (66% yield) of Ac3 ($R^1$=$R^2$=$R^3$=H). LCMS: observed 607.33 (M+1).

Method Ac, Step 3:

Acetyl Chloride (28 mL) was added dropwise to methanol (400 mL) in an ice-bath at 0° C. Then, a solution of Ac3 (4.3 g, $R^1$=$R^2$=$R^3$=H) in 100 mL of MeOH was added slowly at 0° C. Upon completion of addition, ice-bath was removed and the reaction solution was stirred at r.t. overnight. Reaction mixture was neutralized with aqueous sodium carbonate to pH 7 in an ice-bath, concentrated in vacuo. The resulting residue was then dissolved in DCM and worked up. Organic phase was dried over anhydrous sodium sulfate, filtered and evaporated. Residue was purified on a silica gel column with DCM and MeOH containing 0.5% $NH_4OH$ to give 2.37 g (91% yield) of Ac4 ($R^1$=$R^2$=$R^3$=H). LCMS: observed 369.2 (M+1).

Method Ac, Step 4:

Anhydrous DMSO (0.3 mL) in 3 mL anhydrous DCM were added dropwise to a solution of oxalyl chloride (0.22 mL) in 16 mL anhydrous DCM at −78° C. under nitrogen atmosphere. The reaction mixture was stirred for 10 min at −78° C., and a solution of Ac4 (4.7 g, $R^1$=$R^2$=$R^3$=H) in 3 mL anhydrous DCM was added dropwise. After stirring for 1.5 h, TEA (1.2 mL) was added at −78° C. The reaction mixture was stirred 30 min at −78° C., stirred for additional 30 min after removal of the dry ice bath, quenched by diluting with 15 mL of saturated aqueous sodium chloride, and extracted with DCM. The organic phase was dried over anhydrous sodium sulfate to give 765.3 mg of Ac5 ($R^1$=$R^2$=$R^3$=H) which was used in next step without further purification.

Method Ac, Step 5:

A 0.5M solution of $R^4M$ ($R^4M$=3,5-difluorophenylmagnesium bromide) in THF was added dropwise to a vigorously stirred slurry of Ac5 (765.3 mg, $R^1$=$R^2$=$R^3$=H) in 2 mL anhydrous THF at −40° C. The reaction mixture was stirred at −40° C. for 30 min and rt for 2.5 h, quenched over saturated aqueous ammonium chloride, and extracted with DCM. The organic phase was dried over anhydrous sodium sulfate, filtered and evaporated. The resulting residue was purified on a flash silica gel column with DCM and MeOH containing 0.5% $NH_4OH$ to give 210 mg (21%) of a mixture of 4 diastereomers of Ac6 ($R^1$=$R^2$=$R^3$=H, $R^4$=3,5-difluorophenyl). Pure diasteriomers were obtained by chiral separation using Phenomenex Lux Cellulose-1 chiral column with Hexanes and 2-Propanol to give 1.9 mg of Diasteriomer 1; 9.4 mg of Diasteriomer 2; 6.7 mg of Diasteriomer 3 and 1.3 mg of Diasteriomer 4. LCMS: observed 481 (M+1).

Method Af

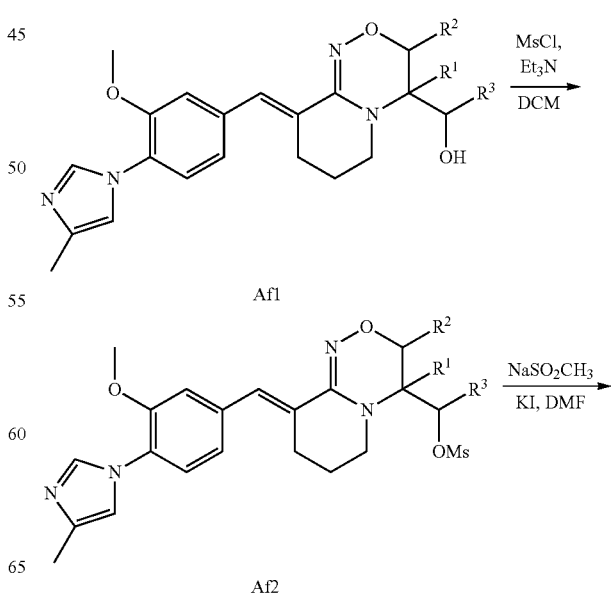

Af1

Af2

-continued

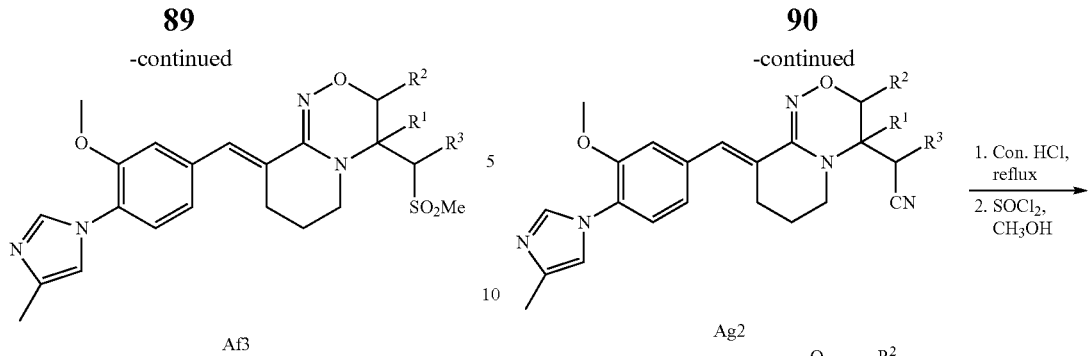

Af3

At 0° C., to alcohol Af1 (1.46 g, 3.96 mmol, $R^1$=$R^2$=$R^3$=H), which was synthesized following similar procedure as described for Method U, in DCM (100 mL) was added $Et_3N$ (0.803 g, 1.1 mL, 7.93 mmol, 2.0 Equiv.) and MSCl (0.817 g, 0.55 mL, 7.13 mmol, 1.8 Equiv.) respectively, the reaction mixture was stirred at this temperature for an hr., and MS showed completion of the reaction. It was quenched with water, the aqueous layer was separated and extracted with DCM, and the combined organic layers were washed with brine, dried over $MgSO_4$, filtered, and evaporated to generate Af2 (1.65 g, 3.70 mmol, 93%, $R^1$=$R^2$=$R^3$=H). $^1$H NMR ($CDCl_3$) δ: 8.00 (s, 1H); 7.42 (s, 1H), 7.24 (d, J=8.0 Hz, 1H), 6.99-6.95 (m, 3H), 4.40-4.32 (m, 2H), 4.28-4.25 (d, J=11.6 Hz, 1H), 3.84 (s, 3H), 3.74-3.68 (m, 1H), 3.69-3.46 (m, 1H), 3.46-3.38 (m, 1H), 3.26-3.18 (m, 1H), 3.07 (s, 3H), 2.84-2.62 (m, 1H), 2.36 (s, 3H), 1.98-1.82 (m, 2H). Electrospray MS: Obs. [M+H]: 447.2.

Af2 (0.226 g. 0.50 mmol, $R^1$=$R^2$=$R^3$=H), KI (0.252 g, 1.52 mmol, 3.0 equiv.), and $NaSO_2CH_3$ (0.155 g, 1.52 mmol, 3.0 Equiv.) in DMF (5 mL) was heated at 120° C. for 1.5 hr. The reaction mixture was cooled to rt, quenched with water, and extracted with DCM. The combined organic layers were washed with brine, dried over $MgSO_4$, filtered, and evaporated. The crude reaction mixture was purified with column chromatography (Eluent: $CH_3OH/EtOAc$=0% to 25%) to afford Af3 (0.060 g, 0.14 mmol, yield 29%, R1=R2=R3=H). $^1$H NMR ($CDCl_3$) δ: 7.70 (s, 1H); 7.40 (s, 1H), 7.21 (d, J=7.6 Hz, 1H), 6.98-6.90 (m, 3H), 4.35 (d, J=11.6 Hz, 1H), 3.90-3.96 (m. 1H), 3.82 (s, 3H), 3.84-3.76 (m, 1H), 3.52-3.40 (m, 2H), 3.32 (dd, J=4.4, 11.6 Hz, 1H), 3.22-3.12 (m, 1H), 3.01 (s, 3H), 2.80-2.62 (m, 2H), 2.28 (s, 3H), 1.98-1.80 (m, 2H). Electrospray MS: Obs. [M+H]: 431.2.

Method Ag

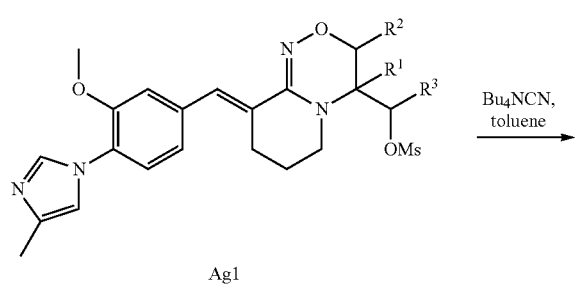

Ag1

-continued

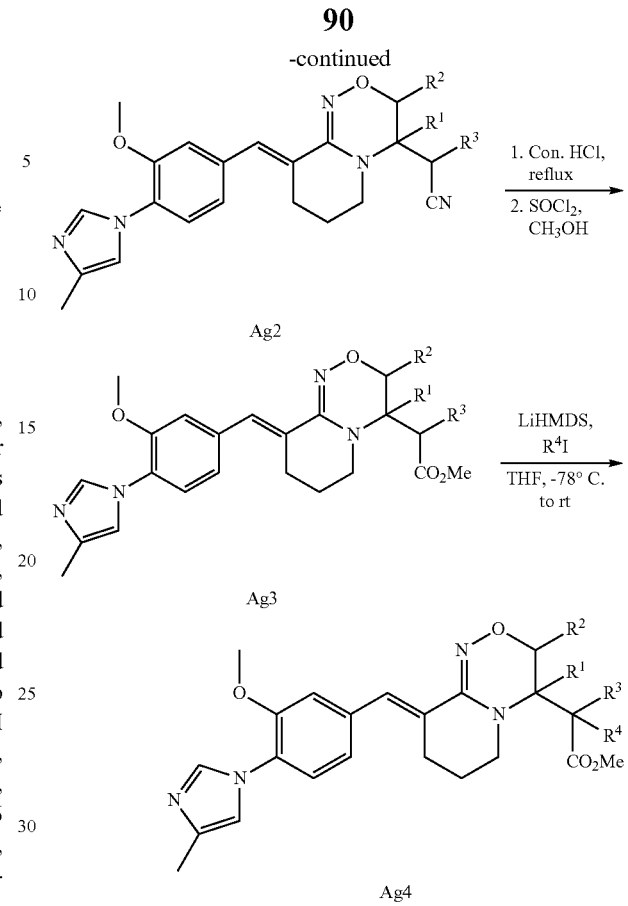

Ag1 (1.42 g, 3.18 mmol, $R^1$=$R^2$=$R^3$=H), which was synthesized following similar procedure as described for Method Af, and $Bu_4NCN$ (1.280 g, 4.77 mmol, 1.5 Equiv.) in toluene (100 mL) was stirred at 80° C. for 1 hr, then cooled to rt, and diluted with EtOAc, washed with water and brine, dried over $MgSO_4$, filtered, and evaporated. The crude reaction mixture was purified by column chromatography (Eluent: $CH_3OH/EtOAc$=0% to 20%), and Ag2 (0.832 g, 2.20 mmol, yield 69%, R1=R2=R3=H) was obtained. $^1$H NMR ($CDCl_3$) δ: 7.66 (s, 1H): 7.38 (s, 1H), 7.18 (d, J=8.0 Hz, 1H), 6.98-6.86 (m, 3H), 4.14 (d, J=11.2 Hz, 1H), 3.79 (s, 3H), 3.72 (dd, J=2.0, 12.0 Hz, 1H), 3.64-3.58 (m, 1H), 3.52-3.40 (m, 1H), 3.22-3.1.4 (m, 1H), 2.80-2.60 (m, 4H), 2.25 (s, 3H), 1.98-1.80 (m, 2H). Electrospray MS: Obs. [M+H]: 378.2.

Ag2 (0.489 g, 1.30 mmol, $R^1$=$R^2$=$R^3$=H) was stirred in concentrated HCl (15 mL) under reflux overnight, and solvent was removed under vacuum. To the crude reaction mixture in $CH_3OH$ (20 mL) was added $SOCl_2$ (0.309 g, 0.19 mL, 2.60 mmol, 2.0 Equiv.) slowly, then stirred at 50° C. for till completion of the reaction. Solvent was removed under vacuum to afford Ag3 ($R^1$=$R^2$=$R^3$=H). $^1$H NMR ($CDCl_3$) δ: 7.74 (s, 1H); 7.42 (s, 1H), 7.14-7.08 (m, 3H). 6.98-6.84 (m, 3H), 4.15 (d, J=11.6 Hz, 1H), 3.82 (s, 3H), 3.80-3.60 (m, 2H), 3.71 (s, 3H), 3.40-3.30 (m, 1H), 3.18-3.04 (m, 1H), 2.84-2.60 (m, 4H), 2.30 (m, 3H), 1.92-1.80 (m, 2H). Electrospray MS: Obs. [M+H]: 411.2.

At −78° C. to Ag3 (0.292 g, 0.71 mmol, 1.0 equiv., $R^1$=$R^2$=$R^3$=H) in THF (10 mL) was added LiHMDS (1.1 mL, 1.1 mmol, 1.5 Equiv.) slowly, it was stirred at this temperature for 30 mins, then R⁴I(0.152 g, 67 uL, 1.07 mmol, 1.5 Equiv., R⁴=Me) in THF (1 mL) was added. The reaction was warmed to rt slowly, and stirred at rt overnight. The reaction was quenched with water, extracted with EtOAc, washed with brine, dried over MgSO₄, filtered, and evaporated. The crude reaction mixture was purified by column chromatography (Eluent: CH₃OH/EtOAc=0% to 20%), and Ag4 (0.173 g, 0.41 mmol, yield 57%, R¹=R²=R³=H, R⁴=H, R⁴=Me) was obtained as a mixture of two diastereomers. The NMR data is represented by the major isomer. ¹H NMR (CDCl₃) δ: 7.67 (s, 1H), 7.36 (s, 1H), 7.19 (d, J=8.0 Hz, 1H), 6.98-6.82 (m, 6H), 4.25 (dd, J=1.2, 11.2 Hz, 1H), 4.18-4.02 (m, 1H), 3.81 (s, 3H), 3.70 (s, 3H), 3.64-3.52 (m, 1H), 3.48-3.38 (m, 1H), 3.32-3.20 (m, 1H), 3.16-3.00 (m, 1H), 2.98-2.82 (m, 1H), 2.80-2.60 (m, 2H), 2.27 (s, 3H), 1.90-1.76 (m, 2H), 1.22 (d, J=8.0 Hz, 3H), Electrospray MS: Obs. [M+H]: 425.2.

Method Ah

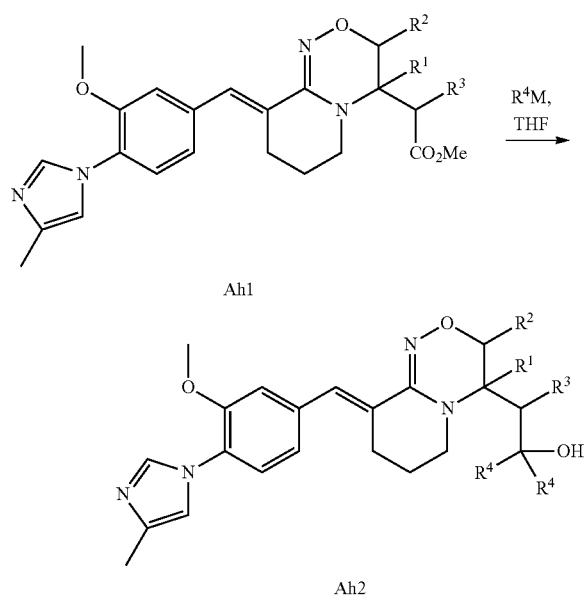

To Ah1 (0.268 g, 0.65 mmol, R1=R2=R3=H), which was synthesized following similar procedure as described for Method Ag, in THF (20 mL) was added R⁴M (R⁴M=MeMgBr, 3.0 M in Et₂O, 0.65 mL, 1.96 mmol, 3.0 Equiv.) dropwise at rt, once TLC showed the completion of the reaction, it's quenched with Sat. NH₄Cl, and extracted with EtOAc. The combined organic layers was washed with Sat. NaHCO₃, dried over MgSO₄, filtered, and evaporated. The crude reaction mixture was purified by column chromatography (Eluent: CH₃OH/EtOAc=0% to 20%), and Ah2 (0.050 g, yield 19%, R¹=R²=R³=H, R⁴=Me) was obtained. ¹H NMR (CDCl₃) δ: 7.68 (s, 1H), 7.40 (s, 1H), 7.19 (d, J=8.0 Hz, 1H), 6.98-6.88 (m, 3H), 4.27 (dd, J=1.6, 11.2 Hz, 1H), 3.80 (s, 3H), 3.80-3.72 (m, 1H), 3.44-3.36 (m, 2H), 3.14-3.02 (m, 1H), 2.78-2.62 (m, 2H), 2.27 (s, 3H), 2.10-2.04 (m, 1H), 1.94-1.78 (m, 2H), 1.78-1.62 (m, 1H), 1.30 (s, 6H). Electrospray MS: Obs. [M+H]: 411.2.

Method Ai

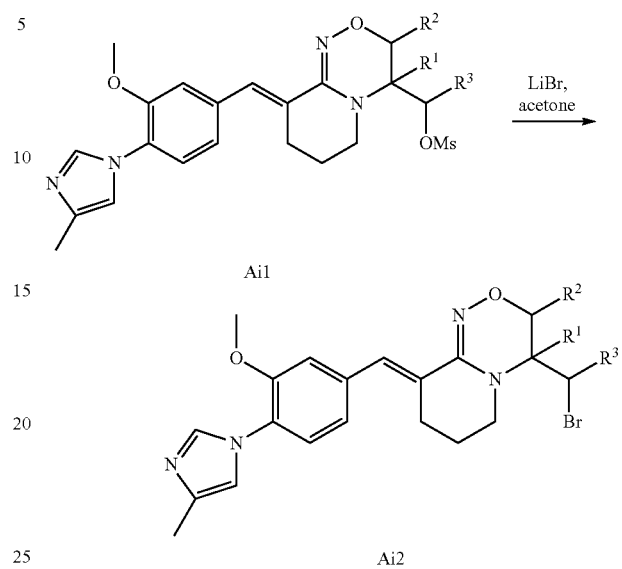

The reaction mixture was stirred under reflux for 4.5 his, Ai1 was synthesized following similar procedure as described for Method Af, solvent was removed, the residue was diluted with EtOAc, washed with water and brine, dried over MgSO₄, filter, and evaporated. The crude reaction mixture was purified by column chromatography (Eluent: CH₃OH/EtOAc=0% to 20%), and the bromide Ai2 (1.03 g, 2.39 mmol, yield 57%, R¹=R²=R³=H) was obtained. ¹H NMR (CDCl₃), δ: 7.74 (s, 1H), 7.43 (s, 1H), 7.22 (d, J=7.6 Hz, 1H), 6.98-6.90 (m, 3H), 4.45 (d, J=11.2 Hz, 1H), 3.83 (s, 3H), 3.70-3.64 (m. 1H), 3.60 (t, J=10.8 Hz, 1H), 3.50-3.42 (m, 3H), 3.22-3.16 (m, 1H), 2.84-2.64 (m, 2 h), 2.31 (s, 3H), 1.92-1.84 (m, 2H). Electrospray MS: Obs. [M+H]: 433.2.

Method Aj

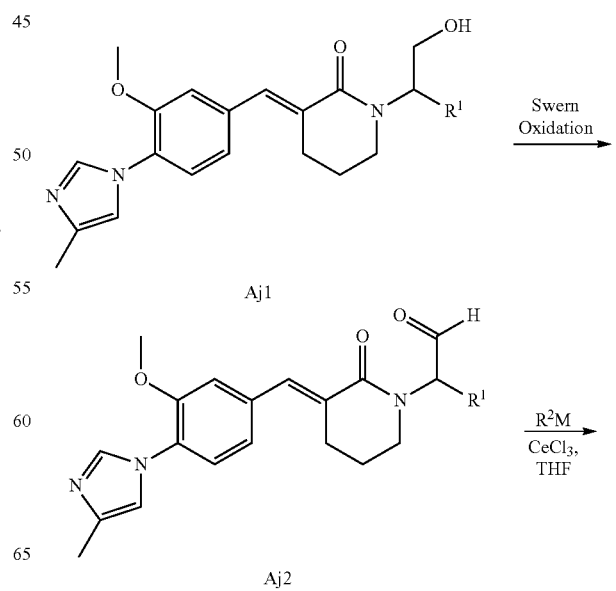

Method Ak

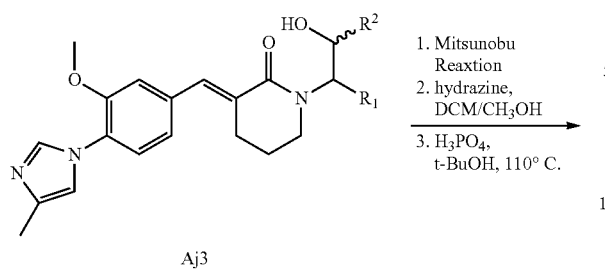

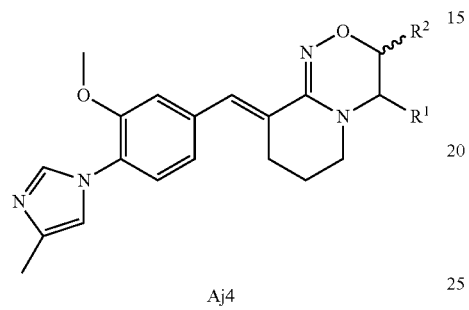

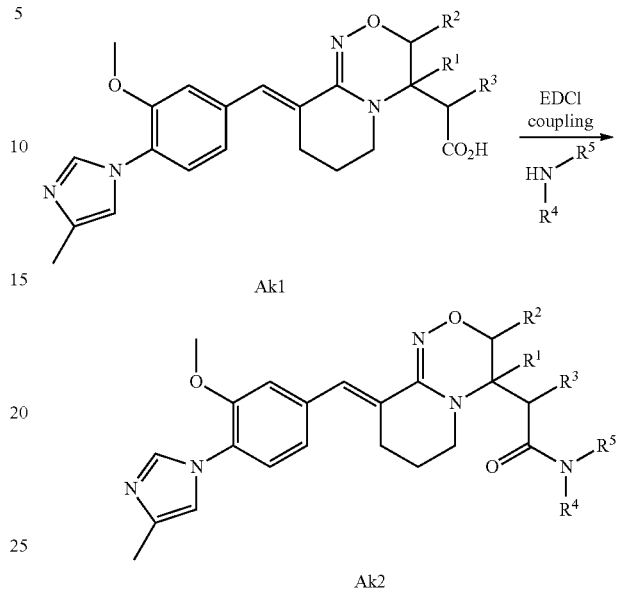

At −78° C., to (COCl)₂ (0.243 g, 0.17 mL, 1.91 mmol, 2.2 Equiv.) in DCM (5 mL) was added DMSO (0.150 g, 0.14 mL, 1.91 mmol, 22 Equiv.)) slowly, and stirred at this temperature for 30 mins. Followed by addition of alcohol Aj1 (0.332 g, 0.87 mmol, R¹=cyclopropyl), which was synthesized following similar procedure as described for Method R, in DCM (10 mL), the reaction mixture was stirred at −78° C. for 2 hrs, and quenched with Et₃N. It was warmed to rt, diluted with DCM, washed with water and brine, dried over MgSO₄, filtered, and evaporated. The aldehyde Aj2 obtained was used for the next step without any purification.

At −78° C., to the suspension of CeCl₃ (0.643 g, 2.61 mmol, 3.0 Equiv.) in THF (10 mL) was added the Grignard reagent (R²M=4-F-phenyl magnesium bromide, 2.0 M in Et₂O, 1.30 mL, 2.61 mmol, 3.0 Equiv.) slowly, it's stirred at this temperature for 45 mins, followed by addition of the aldehyde (0.87 mmol, 1.0 Equiv.) in THF (10 mL). The reaction mixture was warmed to it slowly, and stirred at it overnight. It's cooled to 0° C., and quenched with Sat. NR₄Cl, extracted with EtOAc, the combined organic phases was washed with brine, dried over MgSO₄, filtered, and evaporated. The crude reaction mixture was purified by column chromatography (Eluent: CH₃OH/EtOAc=0% to 25%), and the alcohol was obtained a mixture of diastereomers Aj3 (0.115 g, 0.24 mmol, yield 25% for two steps, R¹=cyclopropyl, R²=4-F-phenyl).

Aj4 was then obtained from Aj3 via method R. For Aj4: ¹H NMR (CDCl₃) δ: 8.18 (s, 1H), 7.69 (s, 1H), 7.65-7.60 (m, 2H), 7.54 (s, 1H), 7.50 (d, J=7.6 Hz, 1H), 7.38-7.20 (m, 4H), 5.18 (d, J=4.4 Hz, 1H), 4.12 (s, 3H), 4.04-3.96 (m, 1H), 3.42-3.38 (m, 2H), 3.10-2.90 (m, 3H), 2.62 (s, 3H), 2.28-1.98 (m, 2H), 1.34-1.20 (m, 1H), 1.08-0.98 (m, 1H), 0.88-0.60 (m, 2H), 0.10-0.02 (m, 1H). Electrospray MS: Obs. [M+H]: 473.3.

A solution of Ak1 (519.0 mg, 1.20 mmol, R1=R2=R3=H), which was synthesized following similar procedure as described for Method Ag, in DMF (20.0 mL) was treated with 2.0 M of HNR⁴R⁵ in methanol (0.720 mL, 1.44 mmol, R4=H, R5=Et), N-(3-Dimethylaminopropyl)-N-ethylcarbodiimide hydrochloride (460.1 mg, 2.40 mmol), and 1-Hydroxybenzotriazole (324.0 mg, 2.40 mmol) followed by the addition of N,N-Diisopropylethylamine (0.836 mL, 4.80 mmol) dropwise. After 18 h, the reaction mixture was diluted with saturated aqeous NaHCO₃ and extracted with EtOAc (3×). The combined organic layers were washed with water (1×), brine (1×), dried over MgSO₄, and concentrated in vacuo. The residue was purified by flash chromatography (0-25% MeOH/EtOAc) and then by reverse phase chromatography to afford Ak2 as a TFA salt (43.7 mg, 0.130 mmol, 8.6%, R¹=R²=R³=R⁴=H, R⁵=Et). ¹H NMR (CD₃OD 400 MHz) δ 7.60 (m, 2H), 7.38 (d, J=15.37 Hz, 2H), 7.23 (d, J=7.32 Hz, 2H), 4.42 (d, J=11.71 Hz, 1H), 4.13 (m, 2H), 3.97 (s, 3H), 3.72 (m, 1H), 3.56 (m, 1H), 3.21 (m, 2H), 2.92 (m, 2H), 2.75 (m, 2H), 2.40 (s, 3H), 2.02 (m, 2H), 1.14 (m, 3H). LCMS: found 424.2 (M+1).

Method Al

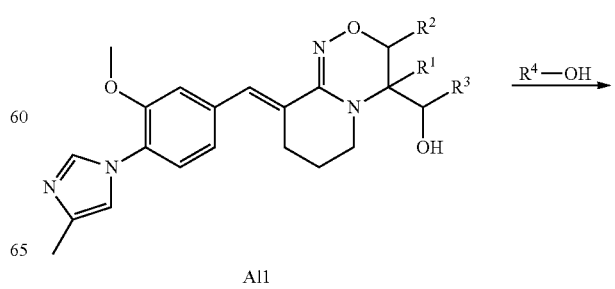

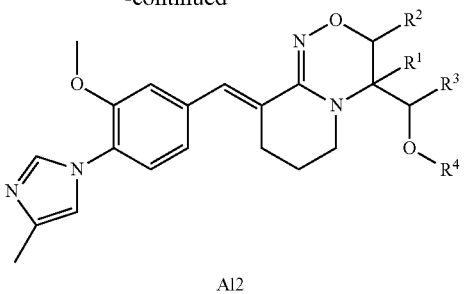

Al2

A solution of Al1 (300.0 mg, 0.814 mmol, $R^1=R^2=R^3=H$), which was synthesized following similar procedure as described for Method U, in Toluene (30.0 mL) was treated with $R^4$OH (136.9 mg, 1.22 mmol, $R^4$=4-F-phenyl), triphenylphosphine (427.1 mg, 1.62 mmol) was cooled at 0.0° C. then the addition of diisopropyl azodicarboxylate (0.320 mL, 1.62 mmol) dropwise and was heated to 60.0° C. for 3 h. The reaction mixture was diluted with EtOAc (150 mL) and washed with 1N NaOH, water, and brine. The crude mixture was dried over MgSO$_4$ and concentrated in vacuo. The residue was purified by flash chromatography (0-50% EtOAc/Hex) and then by reverse phase chromatography to give Al2 as a TFA salt (300.0 mg, 0.648 mmol, 79.6%, R1=R2=R3=H, R4=4-F-phenyl). $^1$H NMR (CD$_3$OD 400 MHz) δ 7.59 (m, 2H), 7.35 (m, 2H), 7.22 (m, 2H), 7.09 (m, 4H), 4.62 (d, J=10.98 Hz, 1H), 4.31 (m, 2H), 4.15 (m, 2H), 3.98 (s, 3H), 3.86 (m, 1H), 3.61 (m, 1H), 2.90 (m, 2H), 2.42 (s, 3H), 2.02 (m, 2H). (m+H), m/z=462.5, found 463.3

Method Am

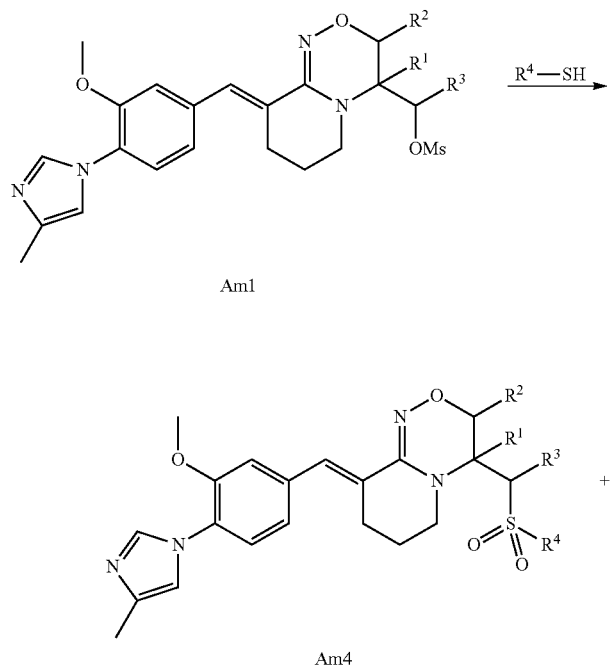

Method AM, Step 1:

A solution of Am1 (300.0 mg, 0.671 mmol, R1=R2=R3=H), which was synthesized following similar procedure as described for Method Af, in EtOH (50 mL) was treated with $R^4$SH (172.2 mg, 1.34 mmol, R4=4-F-phenyl) and KOH (56.54 mg, 1.00 mmol) portionwise and was heated at 70.0° C. for 5 h. The reaction mixture was concentrated in vacuo and diluted with EtOAc (150 mL) then washed with water and brine. The crude mixture was dried over MgSO$_4$ and concentrated in vacuo. The residue was purified by flash chromatography (10-75% EtOAc/Hex) to afford Am2 (256.3 mg, 0.53 mmol, 79.7%, $R^1=R^2=R^3=H$, $R^4$=4-F-phenyl). $^1$H NMR (CDCl$_3$ 400 MHz) δ 7.70 (s, 1H), 7.41 (m, 2H), 7.20 (m, 2H), 7.03 (m, 2H), 6.93 (m, 3H), 4.38 (d, J=11.71 Hz, 1H), 3.85 (s, 3H), 3.63 (d, J=10.98 Hz, 1H), 3.34 (m, 1H), 3.19 (m, 3H), 3.01 (m, 1H), 2.69 (m, 2H), 2.30 (s, 3H), 1.84 (m, 2H). (m+H), m/z=478.5, found 479.3

Method AM, Step 2:

A solution of Am2 (251.6 mg, 0.525 mmol, $R^1=R^2=R^3=H$, $R^4$=4-F-phenyl) in CH$_2$Cl$_2$ (60.0 mL) was treated with m-Chloroperbenzoic acid (353.4 mg, 1.57 mmol). After 1 h. the reaction mixture was quenched with a 1:1 ratio of saturated aqeous NaHCO$_3$ (75 mL), saturated Na$_2$S$_2$O$_3$ (75 mL) and stirred for 1 h. The reaction mixture was extracted with CH$_2$Cl$_2$ (3×) then the combined organic extracts were washed with 1N NaOH and brine, dried over MgSO$_4$ and concentrated in vacuo. The residue was purified by flash chromatography (0-30% MeOH/EtOAc), afforded Am4 (4.3 mg, 0.0087 mmol, 1.6%, $R^1=R^2=R^3=H$, $R^4$=4-F-phenyl): $^1$H NMR (CDCl$_3$ 400 MHz) δ 7.70 (m, 3H), 7.26 (m, 4H), 6.94 (m, 3H), 4.59 (d, J=10.98 Hz, 1H), 3.95 (m, 4H), 3.76 (m, 2H), 3.31 (m, 1H), 3.19 (m, 1H), 2.97 (m, 1H), 2.78 (m, 2H), 2.31 (s, 3H), 1.91 (m, 2H). (m+H), m/z=494.5, found 495.5. The residue was furthered purified by reverse phase chromatography to afford Am3 as a TFA salt (15.8 mg, 0.03 mmol, 5.9%, R1=R2=R3=H, R4=4-F-phenyl). $^1$H NMR (CD$_3$OD 400 MHz) δ 8.09 (m, 3H), 7.57 (m, 2H), 7.42 (m, 2H), 7.27 (m, 2H), 7.16 (d, J=8.05 Hz, 1H), 4.49 (d, J=10.98 Hz, 1H), 4.09 (m, 1H), 3.99 (m, 5H), 3.72 (m, 2H), 3.58 (m, 1H), 2.79 (m, 2H), 2.41 (s, 3H), 1.91 (m, 2H). (m+H), m/z=510.5, found 511.3.

Method An

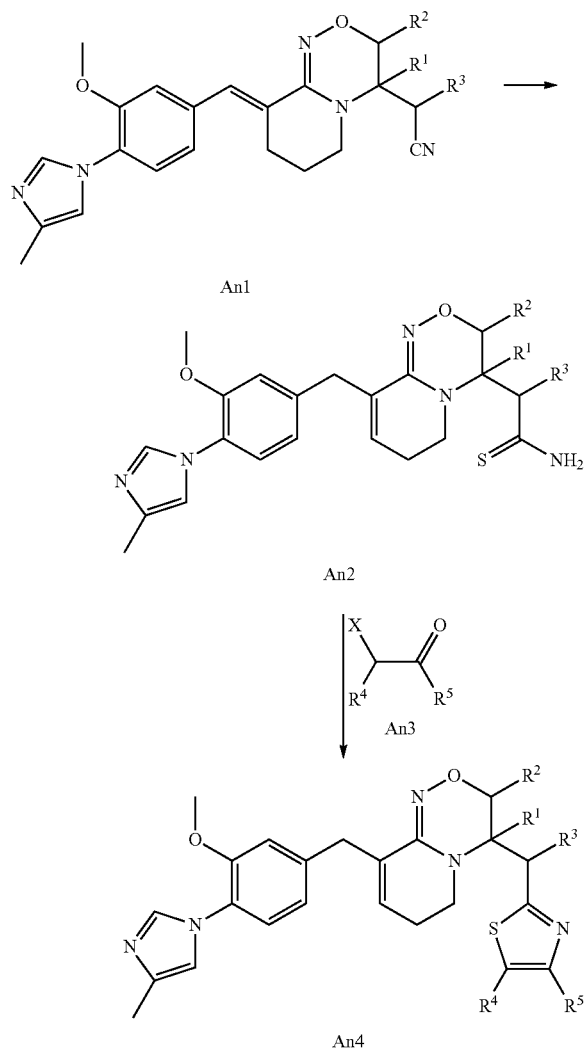

Method An, Step 1:

A solution of An1 (1.12 g, 2.97 mmol, R¹=R²=R³=H), which was synthesized following similar procedure as described for Method Ag, in N,N-Dimethyl acetoamide (30 mL) was treated with (Me₃Si)₂S (0.93 mL, 4.45 mmol) dropwise. After 7 h, the reaction mixture was diluted with saturated aqueous NaHCO₃ and extracted with EtOAc (3×). The combined organic layers were washed with water (1×), brine (1×), dried over MgSO₄, and concentrated in vacuo. The residue was purified by flash chromatography (0-25% MeOH/EtOAc) to give An2 (410 mg, 0.99 mmol, 33.6%, R¹=R²=R³=H). ¹H NMR (CDCl₃ 400 MHz) δ 7.65 (s, 1H), 7.12 (d, J=9.52 Hz, 1H), 6.85 (m, 1H), 5.85 (m, 1H), 4.13 (d, J=10.98 Hz, 1H), 3.99 (m, 1H), 3.80 (s, 3H), 3.68 (m, 1H), 3.59 (s, 1H), 3.47 (s, 2H), 3.33 (m, 2H), 2.35 (m, 1H), 2.27 (s, 3H), 1.81 (m, 2H). (m+H), m/z=411.5, found 412.4.

Method An, Step 2:

A solution of An2 (170.0 mg, 0.413 mmol, R¹=R²=R³=H) in DMF (10.0 mL) was treated with An3 (229.0 mg, 1.24 mmol, R⁴=H, R⁵=t-Butyl, X=Br). After 1.5 h, the reaction mixture was diluted with EtOAc (100 mL) washed with water and brine. The residue was dried over MgSO₄ and concentrated in vacuo. The residue was purified by reverse phase chromatography to afford An4 as a TFA salt (40.2 mg, 0.08 mmol, 19.7%, R¹=R²=R³=R⁴=H, R⁵=tBu). ¹H NMR (CD3OD 400 MHz) δ 7.52 (m, 1H), 7.42 (d, J=8.05 Hz, 1H), 7.19 (s, 1H), 7.05 (s, 1H), 6.98 (m, 1H), 6.18 (m, 1H), 4.23 (d, J=10.98 Hz, 1H), 3.90 (s, 4H), 3.71 (m, 3H), 3.35 (m, 6H), 3.16 (m, 1H), 2.41 (s, 3H), 2.32 (m, 2H), 1.38 (s, 9H). (m+H), m/z=491.6, found 492.3.

Method Ao

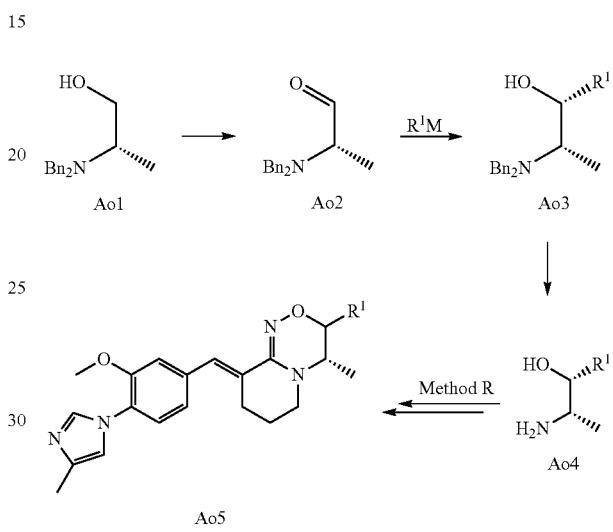

Method A0, Steps 1-3:

To a solution of R¹M (3 equiv., 60 mmol, R1=3,5-difluorophenyl) in THF was added a solution of aldehyde Ao2 (20 mmol) in THF at 0° C. and the resulting solution was stirred for 30 min at 0° C. and then warmed to room temperature and stirred for an additional 30 minutes. Upon completion of the reaction, the reaction mixture was quenched with saturated NH₄Cl, extracted with ethyl acetate, the organic layer was dried with MgSO₄, filtered, concentrated and purified using ethyl acetate in hexanes to afford the amino alcohol Ao3 (R1=3,5-difluorophenyl) in 80% yield. ¹H NMR (CDCl₃) δ 7.31-7.19 (m, 10H), 6.71 (m, 3H), 4.69 (d, 1H, J=6.3 Hz), 3.69 (d, 2H, J=13 Hz), 3.47 (d, 2H, J=13 Hz), 3.04 (m 1H), 2.67 (br-1H), 1.3 (d, 3H, J=7 Hz). To a solution of amino alcohol Ao3 (R¹=3,5-difluorophenyl) in 100 mL methanol was added Pd/C (2 gm of 10% Pd/C) and the resulting solution was stirred under hydrogen for 18 hr or until the reaction completed. The reaction mixture was filtered through a pad of celite and concentrated to afford Ao4 (R¹=3,5-difluorophenyl), which was taken directly to the next step without purification.

Method Ao, Steps 4-6

Following a similar procedure as described in Method R, Ao4 was transformed into Ao5 (R¹=3,5-difluorophenyl). ¹H NMR (CDCl₃) δ 7.69 (s, 1H), 7.51 (s, 1H), 7.21 (m, 2H), 6.92 (m, 4H), 6.8 (m, 1H), 5.9 (br-s, 1H), 3.83 (s. 3H), 3.48 (m, 1H), 3.42 (m, 1H), 3.13 (m, 1H), 2.80 (m, 1H), 2.70 (m, 1H), 2.29 (s, 3H), 1.91 (m, 2H), 1.01 (d, 2H, 6.3 Hz).

Method Ap
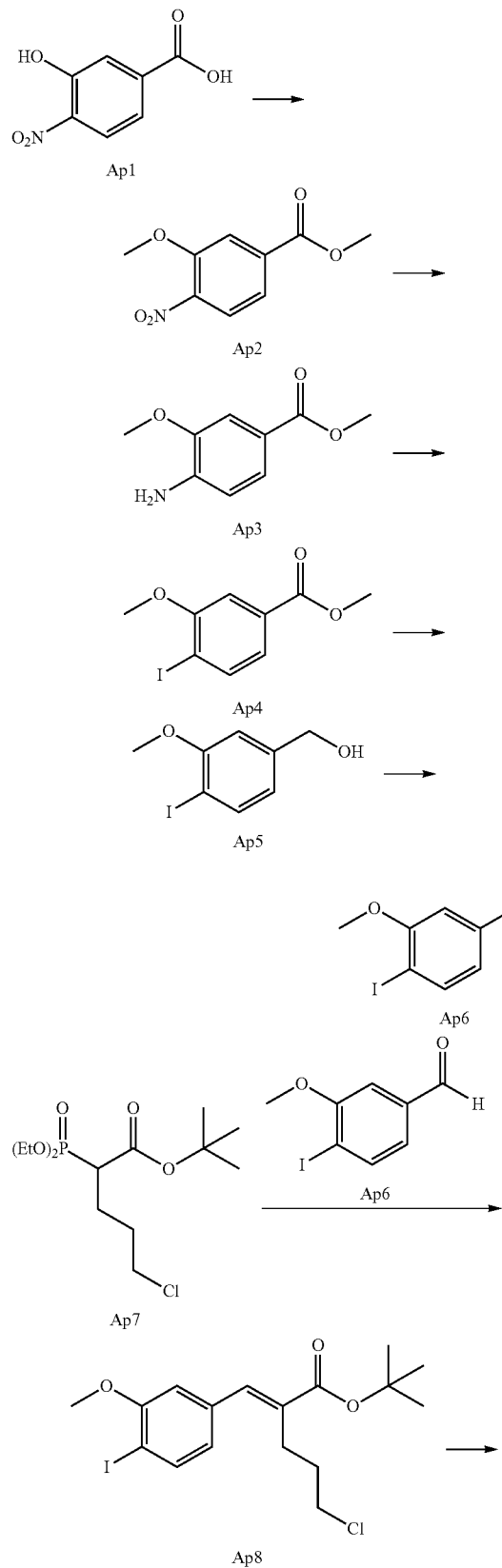
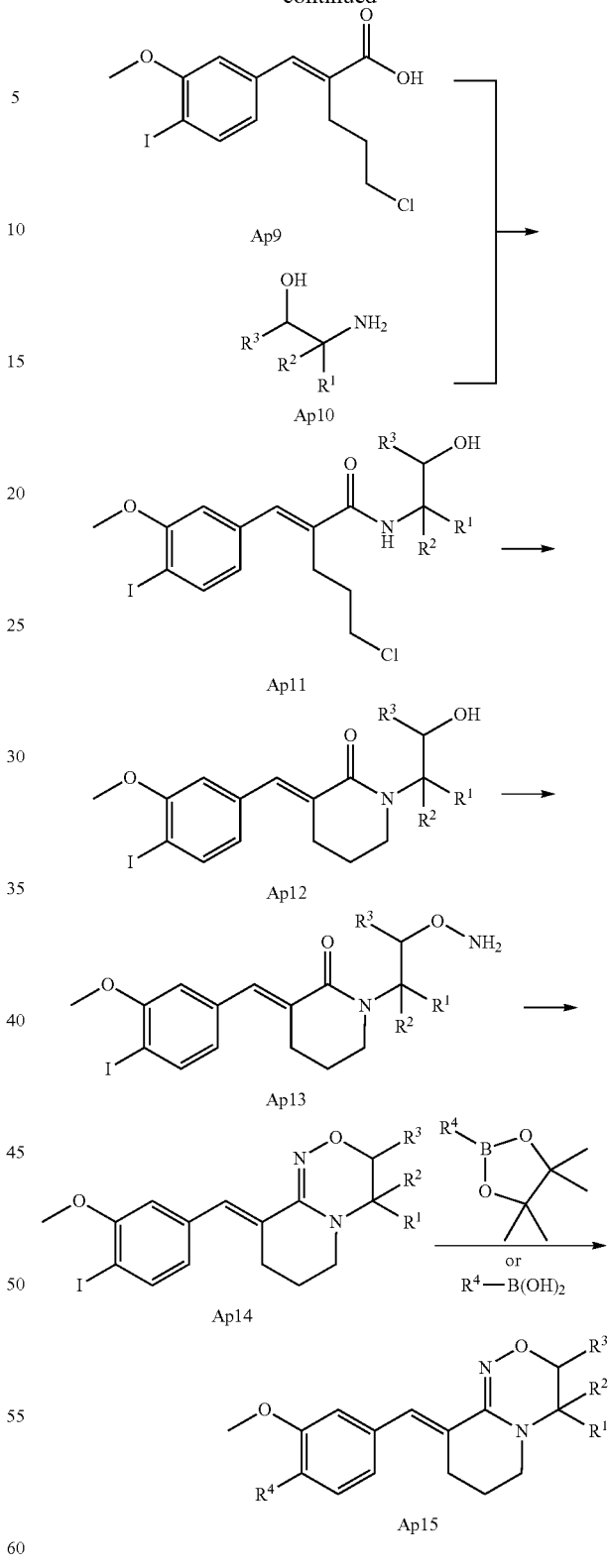
Method Ap, Compound Ap2:
To a 12 L 3-necked round bottomed flask equipped with an addition funnel, under nitrogen and containing a solution of Ap1 (302.7 g, 1.65 mol) in DMF (2.5 L) was added $K_2CO_3$ (905.3 g, 6.55 mol) portionwise over 5 min. Methyl iodide was then added dropwise via addition funnel over 70 min. and then the mixture was stirred overnight. The reaction mixture was slowly poured into an XL extractor containing a stirring mixture of water (7 L) and ice (3 L). The resulting mixture was extracted with ethyl acetate (1×6 L, 1×4 L), washed with water (1×4 L), and brine (1×2 L). The combined organic layers were dried over $MgSO_4$, filtered, and concentrated in vacuo to afford Ap2 (344 g, 97%) as yellow needles. $^1$HNMR ($CDCl_3$, 400 MHz) δ 7.80 (d, 1H), 7.73 (d, 1H), 7.66 (dd, 1H), 3.99 (s, 3H), 3.94 (s, 3H).

Method Ap, Compound Ap3:

To a 2 L Parr bottle containing a mixture of Ap2 (95 g, 0.45 mol) in MeOH (anhydrous, 1.3 L) under nitrogen was added (Raney nickel slurry in water (15 ml) exchanged with methanol 3 times). The reaction mixture was hydrogenated in a Parr shaker at 45 psi overnight. The reaction sat for 30 min. The top layer of the reaction mixture was decanted and filtered. The residue was diluted with DCM (1 L), swirled for 5 min., and filtered resulting in Ap3 (>quantitative) as an off-white solid. $^1$HNMR ($CDCl_3$, 400 MHz) δ 7.52 (dd, 1H), 7.43 (d, 1H), 6.63 (d, 1H), 4.21 (s, 2H), 3.88 (s, 3H), 3.84 (s, 3H).

Method Ap, Compound Ap4:

To a 12 L 3-necked round bottomed flask equipped with a mechanical stirrer, thermometer, addition funnel, nitrogen inlet, and containing a suspension of Ap3 (252 g, 1.39 mol) in water (3.5 L) at 0° C. was added $H_2SO_4$ (20% vol., 700 mL). A solution of $NaNO_2$ (105.6 g, 1.53 mol) in water (550 mL) was added slowly over 1 h at 0° C. to 3° C. and the reaction mixture was stirred further for 1 h. Next, urea (25 g, 0.417 mol) was added to the reaction mixture portionwise and stirred for 15 min. Then a solution of KI (242.3 g, 1.46 mol) in water (600 mL) was added to the 0° C. reaction mixture over 30 min. The reaction mixture was then heated at 55° C. for 1.5 h. Next, ethyl acetate (4 L) was used to dissolve the reaction mixture and the resulting solution was poured slowly into a solution of $Na_2S_2O_5$ (650 g) in ice water (4 L) and the flask was rinsed with ethyl acetate (2 L) and stirred for 15 min. The resulting layers were separated and the aqueous phase (pH~3) was extracted with ethyl acetate (2 L). The combined organic layers were washed with water (2 L×2), brine (1 L), dried over $Mg_2SO_4$, filtered, and concentrated in vacuo. The crude material was purified via silica gel plug (ethyl acetate/hexanes) to afford Ap4 (370 g, 91%) as a white solid. $^1$HNMR ($CDCl_3$, 400 MHz) δ 7.83 (d, 1H), 7.43 (d, 1H), 7.35 (dd, 1H), 3.93 (s, 3H), 3.90 (s, 3H).

Method Ap, Compound Ap5:

To a 12 L 3-necked round bottomed flask equipped with a mechanical stirrer, thermometer, nitrogen inlet, and containing a solution of Ap4 (270 g, 0.925 mol) in THF (4 L) was added $LiBH_4$ (60.4 g, 2.77 mol) portionwise at room temperature. The reaction mixture was placed in an ice bath and methanol (135 mL) was added dropwise. After the addition was complete the ice bath was removed and the reaction was heated to 65° C. for 1 h. The reaction was then cooled in an ice bath and poured into an ice cold solution of saturated aq. $NH_4Cl$ (2 L) and ethyl acetate (4 L) followed by rinsing of the flask with ethyl acetate (2 L). The solution was stirred for 15 min., the layers were separated and the aqueous layer was extracted with ethyl acetate (4 L). The combined organic layers were washed with water (2 L×2), brine (1 L), dried over $MgSO_4$, filtered and concentrated in vacuo to afford Ap5 (>quantitative) as a light-yellow oil. $^1$HNMR ($CDCl_3$, 400 MHz) δ 7.70 (d, 1H), 6.86 (d, 1H), 6.67 (dd, 1H), 4.64 (d, 2H), 3.88 (s, 3H).

Method Ap, Compound Ap6:

To a 12 L 3-necked round bottomed flask equipped with a mechanical stirrer, thermometer, addition funnel, nitrogen inlet, and containing a solution of $(COCl)_2$ (123.7 g, 0.975 mol) in DCM (3.5 L) at −70° C. was added a solution of DMSO (173 g, 2.215 mop in DCM (250 mL) over 30 min, and was stirred an additional 30 min. at −72° C. Next, a solution of Ap5 (234 g, 0.886 mol) in DCM (1 L) was added over 1.5 h to the reaction solution keeping the reaction temperature between −65° C. and −70° C. and then the reaction solution was stirred for an additional 30 min. at −70° C. Next, triethylamine (363 g, 3.587 mol) was added over 15 min. and then the reaction mixture was stirred for an additional 1 h at −65° C. The cooling bath was removed and the reaction mixture was poured into an extractor filled with ice water (3 L) and stirred for 15 min. The layers were separated and the aqueous layer was extracted with DCM (2 L). The combined organic layers were washed with HCl (1N, 1.5 L), water (2 L×3), brine (1 L), dried over $MgSO_4$, filtered, and dried in vacuo. The crude material was triturated with hexanes (300 mL), filtered, washed with hexanes (100 mL×2), and dried under vacuum to afford Ap6 (212.7 g, 92%) as an off-white solid. $^1$HNMR ($CDCl_3$, 400 MHz) δ 9.93 (s, 1H), 7.96 (d, 1H), 7.27 (d, 1H), 7.17 (dd, 1H), 3.94 (s, 3H).

Method Ap, Compound Ap8:

To a room temperature solution of Ap7 (50.0 g, 0.152 mol) and Ap6 (37.7 g, 0.144 mol) in THF/EtOH (350 mL/105 mL) and under nitrogen was added $LiOH*H_2O$ (14.6 g, 0.349 mol). After 24 h, the reaction was diluted with ethyl acetate and water and the aqueous layer was extracted with ethyl acetate. The combined organic layers were dried over $MgSO_4$, and concentrated in vacuo. The crude material was purified by silica gel chromatography with ethyl acetate/hexanes to afford a yellow oil. The yellow oil was then dissolved in hot hexanes and gradually cooled to room temperature and then placed in an ice-bath. The resulting solid was filtered and washed with cold hexanes to afford Ap8 (23.97 g, 38%) as a white solid. $^1$HNMR ($CDCl_3$, 400 MHz) δ 7.76 (d, 1H), 7.52 (s, 1H), 6.75 (d, 1H), 6.68 (dd, 1H), 3.88 (s, 3H), 3.55 (t, 2H), 2.61 (m, 2H), 2.00 (m, 2H), 1.53 (s, 9H).

Method Ap, Compound Ap9:

To a round bottomed flask equipped with an addition funnel and nitrogen inlet and containing a 10° C. solution of Ap8 (23.97 g, 0.054 mol) in DCM (96 mL) was added trifluoroacetic acid (48 mL) dropwise over 45 minutes. After addition was complete, the cold bath was removed. After 3 h, the reaction was concentrated in vacuo and dried under vacuum to afford Ap9 (20.94 g, >100%) as an off-white solid. $^1$HNMR ($CDCl_3$, 400 MHz) δ 7.79 (t, 2H), 6.81 (d, 1H), 6.76 (dd, 1H), 3.90 (s, 3H), 3.59 (t, 2H), 2.70 (m, 2H), 2.05 (m, 2H); MS (LCMS, M+1) 381.0.

Method Ap, Compound Ap11:

To a room temperature solution of Ap9 (20.94 g, 0.055 mol), Ap10 (10.52 g, 0.055 mol, R1=R3=H, R2=3,4-5-trifluorophenyl), and HOBT (11.16 g, 0.082 mol) in DMF (149 mL) and under nitrogen was added diisopropylethylamine (58 mL, 0.33 mol) followed by EDCl*HCl (19.51 g, 0.10 mol). After 16 h, the reaction was diluted with ethyl acetate (1 L), washed with aq. sat. $NaHCO_3$ (2×300 mL), water (2×200 mL), and brine, (1×100 mL). The organic layer was then dried over $Na_2SO_4$, concentrated in vacuo, and dried under vacuum to afford crude Ap11 ($R^1=R^3=H$, $R^2=3,4$-5-trifluorophenyl) as an orange oil. MS (LCMS, M+1) 554.0.

Method Ap, Compound Ap12:

To a room temperature solution of crude Ap11 (35.58 g, R1=R3=H, R2=3,4-5-trifluorophenyl) in DMF (225 mL) and under nitrogen was added t-BuOK (8.8 g) in two portions. After 2.5 h, the reaction mixture was poured over iced-brine and then extracted with ethyl acetate. The combined organic layers were dried over $Na_2SO_4$, and concentrated in vacuo. The crude material was purified by silica gel chromatography with ethyl acetate/methanol/hexanes to afford compound Ap12 (R¹=R³=H, R²=3,4-5-trifluorophenyl). ¹HNMR (CDCl₃, 400 MHz) δ 7.78 (m, 2H). 6.97 (t, 2H), 6.79 (d, 1H), 6.72 (dd, 1H), 5.68 (t, 1H), 4.14 (m, 2H), 3.88 (s, 3H), 3.35 (m, 1H), 3.15 (m, 1H), 2.78 (m, 2H), 1.81 (m, 2H); MS (LCMS, M+1) 518.2.

Method Ap, Compound Ap13:

Compound Ap13 (R¹=R³=H, R²=3,4-5-trifluorophenyl) was synthesized using a method similar to Method R, Step 2. ¹HNMR (CDCl₃, 400 MHz) δ 7.82 (s, 1H), 7.75 (d, 1H), 6.93 (t, 2H), 6.80 (d, 1H), 6.75 (dd, 1H), 6.29 (t, 1H), 4.13 (d, 2H), 3.83 (s, 3H), 3.27 (m, 1H), 3.03 (m, 1H), 2.81 (m, 2H), 1.86 (m, 2H); MS (LCMS, M+1) 533.2.

Method Ap, Compound Ap2:Ap14

Compound Ap14 was synthesized using a method similar to Method R, Step 3. Purified compound Ap14 (R1=R3=H, R2=3,4-5-trifluorophenyl) was then resolved via SFC using an OD-H column. ¹HNMR (CDCl₃, 400 MHz) δ 7.73 (d, 1H), 7.47 (s, 1H), 6.98 (t, 2H), 6.76 (s, 1H), 6.68 (d, 1H), 4.26 (s, 1H), 4.03 (s, 2H), 3.87 (s, 3H), 3.11 (m, 2H), 2.70 (m, 2H), 1.80 (m, 2H); MS (LCMS, M+1) 515.0.

Method Ap, Compound Ap15:

To a microwave vial under nitrogen was added compound Ap14 (R¹=R³=H, R²=3,4-5-trifluorophenyl, 0.250 g, 0.486 mmol), Pd(PPh₃)₄ (0.056 g, 0.0486 mmol), R⁴Bpin (R⁴Bpin=1-methyl-1H-pyrazole-4-boronic acid pinacol ester, 0.303 g, 1.46 mmol), Na₂CO₃ (0.155 g, 1.46 mmol) in water (1.5 mL), and acetonitrile (3.5 mL). This mixture was then heated in a microwave to 130° C. for 30 min. on high absorption. The resulting mixture was then poured over iced-brine, and then extracted with ethyl acetate. The combined organic layers were dried over Na₂SO₄, and concentrated in vacuo. The crude material was purified by silica gel chromatography with methanol/ammonium hydroxide/DCM and MeOH/CHCl₃ to afford compound Ap15 (R¹=R³=H, R²=3,4-5-trifluorophenyl, R⁴=4-(1-methyl-1H-pyrazole), 0.109 g, 48%) as a yellow solid. ¹HNMR (CDCl3, 400 MHz) δ 7.86 (d, 2H), 7.51 (m, 2H), 6.99 (t, 3H), 6.91 (s. 1H), 4.26 (t, 1H), 4.03 (d 2H), 3.95 (s, 3H), 3.90 (s, 3H), 3.11 (m, 2H), 2.86 (m, 1H), 2.76 (m, 1H), 1.86 (m, 2H); MS (LCMS, M+1) 469.3.

Method Aq

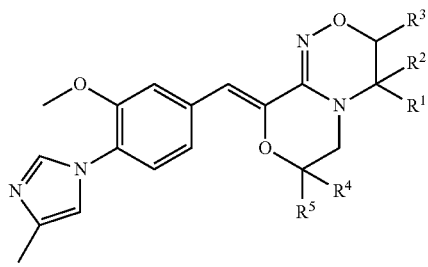

R¹=R³=R⁴=H, R²=3,4,5-trifluorophenyl, R⁵=Me

Method Aq, Step 1:

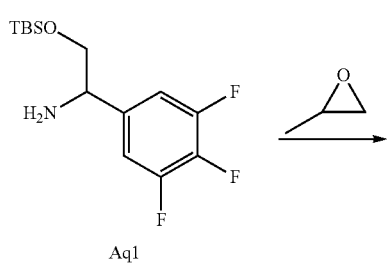

A mixture of compound Aq1 (7 g), propanepoxide (16 mL) and ZrCl₄ (0.27 g) was stirred at room temperature over night before it was filtered through celite. Solvent was removed and the crude residue was purified by column chromatography eluting with EtOAc/hexanes to yield compound Aq2 (6 g).

Method Aq, Step 2:

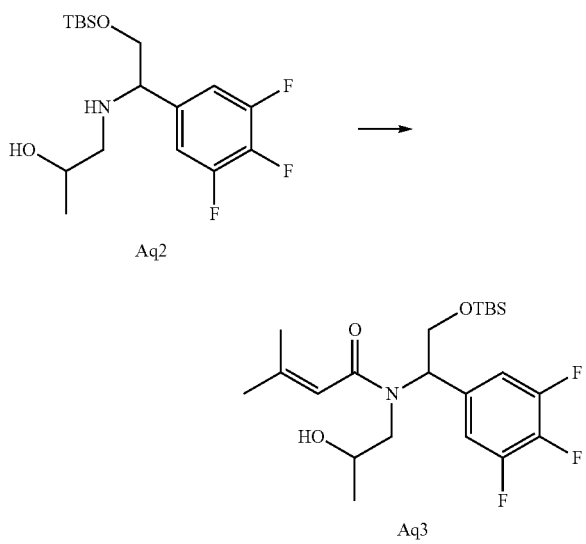

NEt₃ (5.2 mL) was added to Aq2 (6.77 g) in DCM (150 mL) followed with addition of 3,3-dimethyl propanoyl chloride (2.5 mL) at 0° C. The reaction was quenched in 2 hours with addition of NaHCO₃ solution. The aqueous layer was extracted with DCM. The organic layer was washed with water, brine, dried over MgSO₄, and concentrated to give the crude product which was purified by column chromatography eluting with EtOAc/hexanes to yield compound Aq3 (4.3 g).

Method Aq, Step 2:

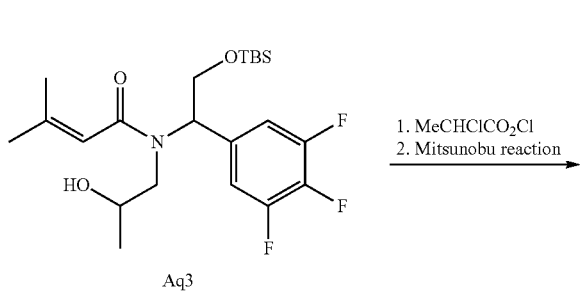

Aq3

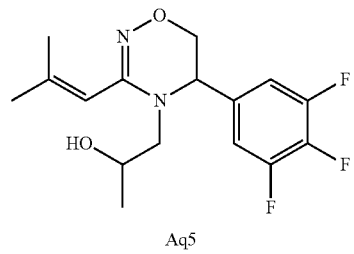

Aq5

Compound Aq4 (3.0 g) in MeOH/DCM (60 mL, 1/1) was treated with NH₂NH₂.xH₂O (1.07 mL) at room temperature. The mixture was stirred for 2 hours before it was diluted with DCM and NaHCO₃ solution. The aqueous layer was extracted with DCM. The organic layer was washed with water, brine, dried over MgSO₄, and concentrated to give the crude product which was purified by column chromatography eluting with EtOAc/hexanes to yield oxyamine (1.6 g). The oxyamine was dissolved in EtOH (100 mL) and added to P₂O₅ (13.1 g). The resulting mixture was stirred at 80° C. overnight before it was cooled and concentrated to 20 mL. The residue was diluted with EtOAc and NaOH solution (10%). The aqueous layer was extracted with EtOAc. The organic layer was washed with water, brine, dried over MgSO₄, and concentrated to give the crude product which was purified by column chromatography eluting with EtOAc/hexanes to yield compound Aq5 (1.5 g).

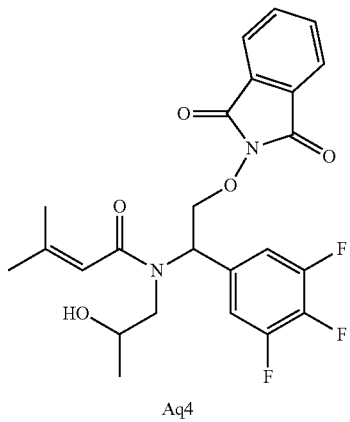

Aq4

MeCHClCO₂Cl (0.26 mL) was added to a solution of compound Aq3 (2.1 g) in MeOH (15 mL) at room temperature. The reaction was worked up in 3 hours by removing solvent. The crude residue was purified by column chromatography eluting with EtOAc/hexanes to yield dial (1.0 g). The diol (3.5 g) in THF (100 mL) was treated with N-hydroxyphthalimide (2.6 g), 1,1'-(azodicarbonyl)dipiperidine (5.33 g) and PBu₃ (5.1 mL) at room temperature. The mixture was heated at 80° C. overnight. The mixture was cooled to room temperature and solid was filtered through celite. The residue was taken up in EtOAc and treated with NaHCO₃ solution. The aqueous layer was extracted with EtOAc. The organic layer was washed with water, brine, dried over MgSO₄, and concentrated to give the crude product which was purified by column chromatography eluting with EtOAc/hexanes to yield compound Aq4 (3.0 g).

Method Aq, Step 4:

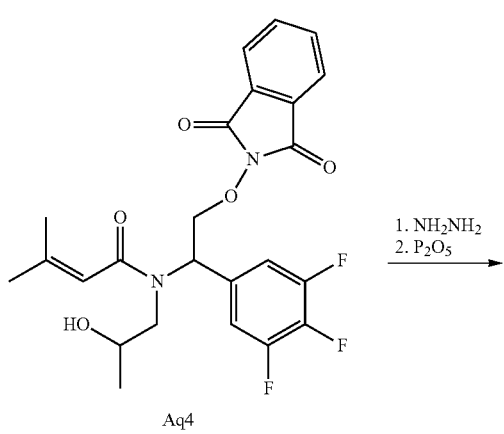

Aq4

Method Aq, Step 5:

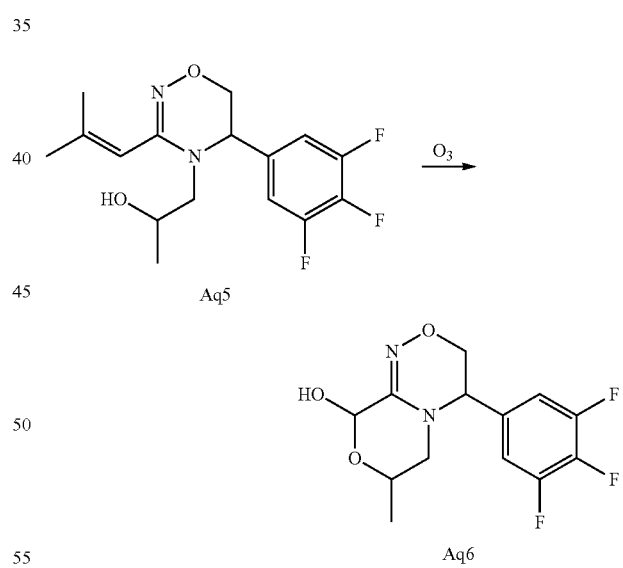

Aq5

Aq6

Compound Aq5 (1.9 g) in MeOH/DCM (150 mL, 2/3) was ozonized at −78° C. for 1 hour. After purging away excess of O₃ with O₂, Me₂S (3.3 mL) was added to quench the reaction. Solvent was removed. The residue was diluted with EtOAc and NaCl solution (10%). The aqueous layer was extracted with DCM. The organic layer was washed with water, brine, dried over MgSO₄, and concentrated to give the crude product which was purified by column chromatography eluting with EtOAc/hexanes to yield compound Aq6 (0.9 g).

Method Aq, Step 6:

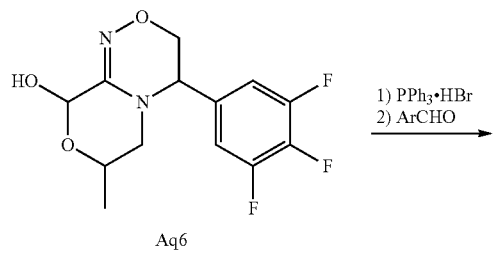

Aq6

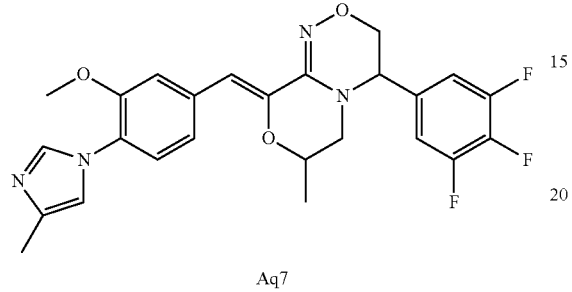

Aq7

Method Ar

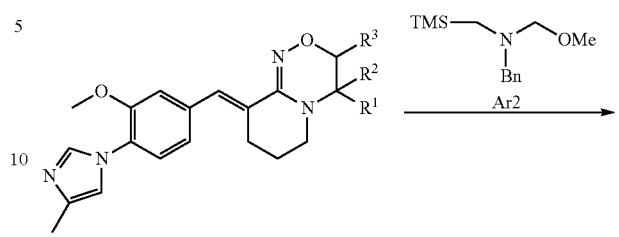

Ar1

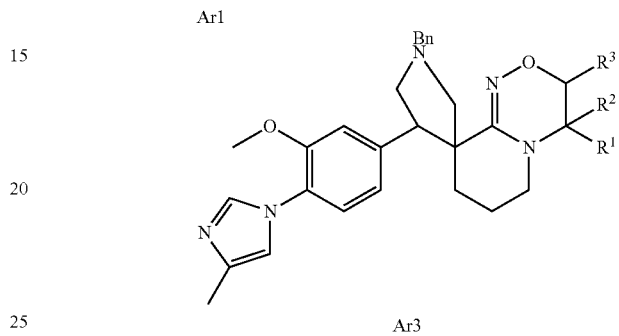

Ar3

Compound Aq6 (0.46 g) in ClCH$_2$CH$_2$Cl/MeCN (20 mL, 1/1) was treated with PPh$_3$.HBr (0.73 g) and heated for 5 hours before solvent was removed. The residue was taken up in THF/DMF (27.5 mL, 10/1) and 3-methoxy-4-(1-(4-methylinidazolyl))benzaldehyde (0.29 g) was added. The mixture was cooled to 0° C. and LHMDS (4.5 mL, M in THF) was added dropwise. The mixture was stirred at 0° C. for 1 hour and then room temperature for 1 hour before NH$_4$Cl was added to quench the reaction. The residue was diluted with EtOAc. The aqueous layer was extracted with EtOAc. The organic layer was washed with water, brine, dried over MgSO$_4$, and concentrated to give the crude product which was purified by column chromatography eluting with EtOAc/hexanes to yield compound Aq7 (0.13 g).

TFA (7.9 uL) was added at room temperature to a solution of compound Ar1 (40 mg, R1=R3=H, R2=3,4,5-trifluorophenyl), which was synthesized following similar procedure as described for Method R, and compound Art (43.7 uL) in THF (1.2 mL). The mixture was stirred over night before solvent was removed. The residue was purified with Gilson reverse phase HPLC to give product Ar3 (38 mg, R1=R3=H, R2=3, 4,5-trifluorophenyl), LCMS (M+H)=602.3.

The compounds (253-394) in the table below were synthesized by the following procedures similar to those indicated in the "Method of Synthesis" column.

| Structure | Observed Mass | Rt | Method of Synthesis |
|---|---|---|---|
| Enantiomer I<br>253 | 607.33 | 5 | R |

| Structure | Observed Mass | Rt | Method of Synthesis |
|---|---|---|---|
| 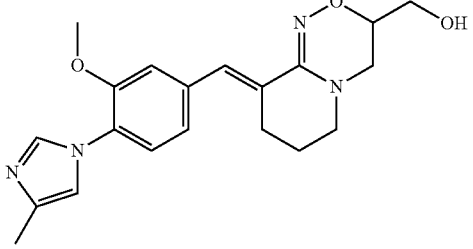<br>Enantiomer I<br>254 | 369.2 | 1.7 | Ac |
| 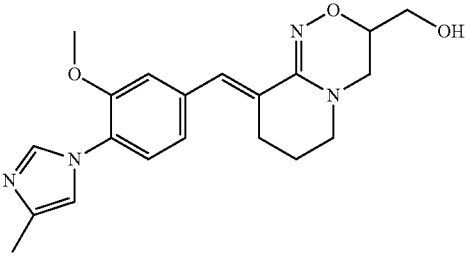 [SMILES: COc1cc(/C=C2\CCCN3CC(CO)ON=C23)ccc1-n1cnc(C)c1]<br>Enantiomer II<br>255 | 369.2 | 2.2 | Ac |
| 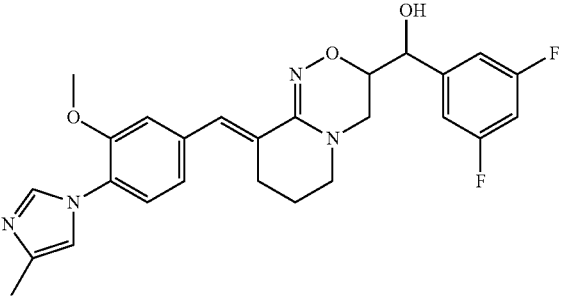 [SMILES: COc1cc(/C=C2\CCCN3CC(C(O)c4cc(F)cc(F)c4)ON=C23)ccc1-n1cnc(C)c1]<br>Diastereomer I<br>256 | 481.2 | 1.6 | Ac |
| 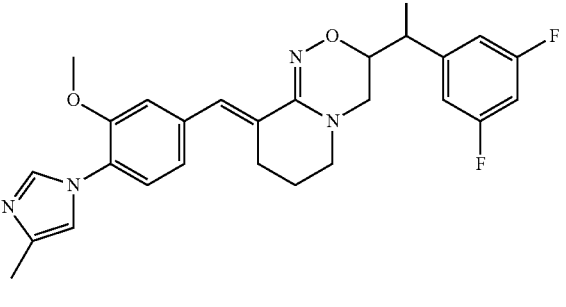<br>Diastereomer II<br>257 | 481.2 | 1.6 | Ac |

| Structure | Observed Mass | Rt | Method of Synthesis |
|---|---|---|---|
| 258 | 481.26 | 2.7 | R |
| 259 | 423.23 | 1 | R |
| 260 | 423.23 | 1 | R |
| 261 | 602.33 | 2.5 | Ar |

-continued

| Structure | Observed Mass | Rt | Method of Synthesis |
|---|---|---|---|
| 262 Racemic | 423 | | R |
| 263 | 431.24 | 2.1 | Af |
| 264 | 378.21 | 2 | Ag |
| 265 | 411.23 | 2.1 | Ag |
| 266 | 425.23 | 2.3 | Ag |

| Structure | Observed Mass | Rt | Method of Synthesis |
|---|---|---|---|
| 267 | 411.23 | 2.2 | Ah |
| 268 | 432.24 | 2.6 | Ai |
| 269 | 473.26 | 3.1 | Aj |
| 270 | 473.26 | 3.3 | Aj |

-continued

| Structure | Observed Mass | Rt | Method of Synthesis |
|---|---|---|---|
| 271 | 447.2 | | Af |
| 272 | 463.2 | | Aj |
| 273 Racemic | 469.26 | 2.7 | R |
| 274 | 381.21 | 2.2 | R |

-continued

| Structure | Observed Mass | Rt | Method of Synthesis |
|---|---|---|---|
| 275 | 491.27 | 3 | R |
| 276 | 339.19 | 1.7 | R |
| 277 | 429.24 | 2.5 | R |
| 278 | 459.25 | 3.1 | R |

-continued

| Structure | Observed Mass | Rt | Method of Synthesis |
|---|---|---|---|
| 279 | 369.2 | 2.2 | U |
| Diastereomer I 280 | 479.26 | 3 | Z |
| Diastereomer II 281 | 479.26 | 3 | Z |
| 282 | 395.22 | — | R |

-continued

| Structure | Observed Mass | Rt | Method of Synthesis |
|---|---|---|---|
| 283 | 459.25 | 1.9 | R |
| 284 | 369.2 | 2.3 | U |
| Enantiomer I 285 | 469.26 | 3.4 | R |
| Enantiomer II 286 | 469.26 | 3.4 | R |

-continued

| Structure | Observed Mass | Rt | Method of Synthesis |
|---|---|---|---|
| 287 | 492.3 | — | V |
| 288 | 506.3 | — | V |
| 289 | 512.3 | — | V |
| 290 | 512.3 | — | V |

-continued

| Structure | Observed Mass | Rt | Method of Synthesis |
|---|---|---|---|
| 291 | 526.3 | — | V |
| 292 | 528.3 | — | V |
| 293 | 540.3 | — | V |
| 294 | 540.3 | — | V |

-continued

| Structure | Observed Mass | Rt | Method of Synthesis |
|---|---|---|---|
| 295 | 540.3 | — | V |
| 296 | 554.3 | — | V |
| 297 | 554.3 | — | V |
| 298 | 478.3 | — | V |

| Structure | Observed Mass | Rt | Method of Synthesis |
|---|---|---|---|
| 299 | 478.3 | — | V |
| 300 | 486.3 | — | V |
| 301 | 486.3 | — | V |
| 302 | 490.3 | — | V |
| 303 | 490.3 | — | V |

US 8,673,900 B2

133                                                                            134

-continued

| Structure | Observed Mass | Rt | Method of Synthesis |
|---|---|---|---|
| 304 | 497.3 | — | V |
| 305 | 487.3 | — | V |
| 306 | 487.3 | — | V |
| 307 | 424.23 | 2.2 | Y |
| 308 | 438.24 | 2 | Y |

-continued
| Structure | Observed Mass | Rt | Method of Synthesis |
|---|---|---|---|
| 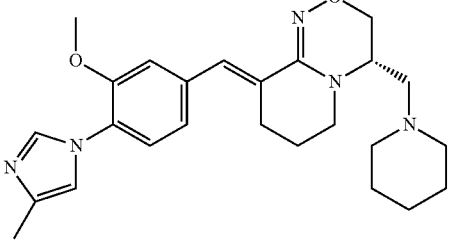 309 | 436.24 | 2.2 | Y |
| 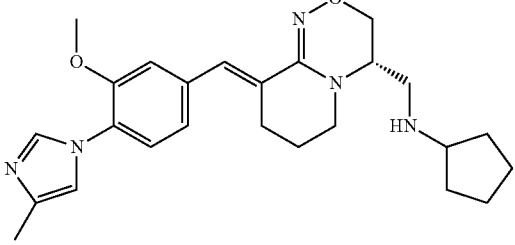 310 | 436.24 | 2.6 | Y |
| 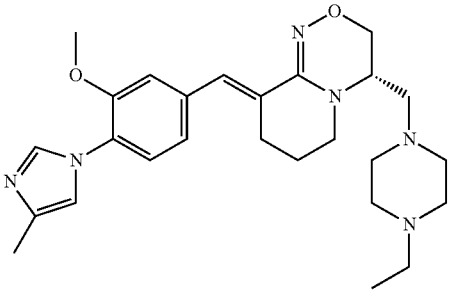 [SMILES: CCN1CCN(C[C@H]2CON=C3/C(=C/c4ccc(-n5cnc(C)c5)c(OC)c4)CCCN32)CC1] 311 | 465.26 | 2.4 | Y |
| 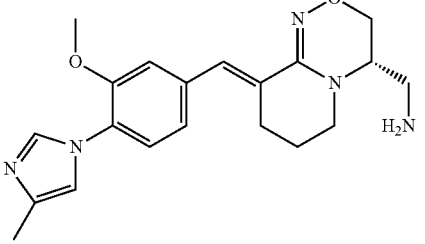 312 | 368.2 | 1.9 | V |
| 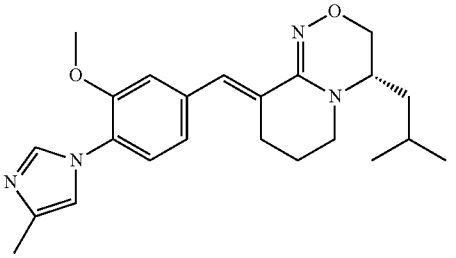 [SMILES: COc1cc(/C=C2\CCCN3C2=NOC[C@@H]3CC(C)C)ccc1-n1cnc(C)c1] 313 | 395.22 | 3 | R |

-continued
| Structure | Observed Mass | Rt | Method of Synthesis |
|---|---|---|---|
| 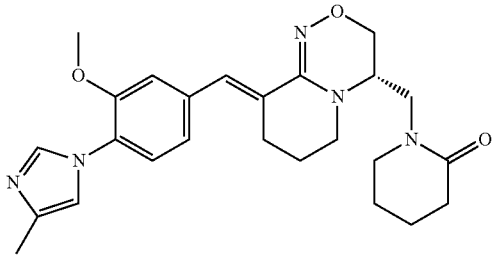 [SMILES: COc1cc(/C=C2\CCCN3C2=NOC[C@@H]3CN2CCCCC2=O)ccc1-n1cnc(C)c1]<br>314 | 450.25 | 2.4 | W |
| 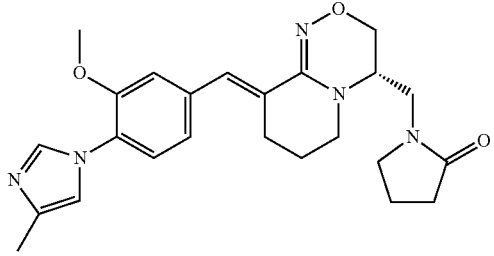 [SMILES: COc1cc(/C=C2\CCCN3C2=NOC[C@@H]3CN2CCCC2=O)ccc1-n1cnc(C)c1]<br>315 | 436.24 | 2.2 | W |
| 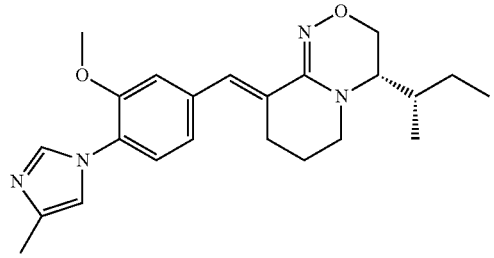 [SMILES: CC[C@H](C)[C@H]1CON=C2/C(=C/c3ccc(-n4cnc(C)c4)c(OC)c3)CCCN21]<br>316 | 395.22 | 2.8 | R |
| 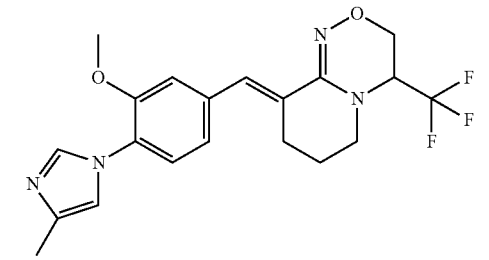 [SMILES: COc1cc(/C=C2\CCCN3C2=NOCC3C(F)(F)F)ccc1-n1cnc(C)c1]<br>Enantiomer I<br>317 | 407.22 | 3.2 | R |
| 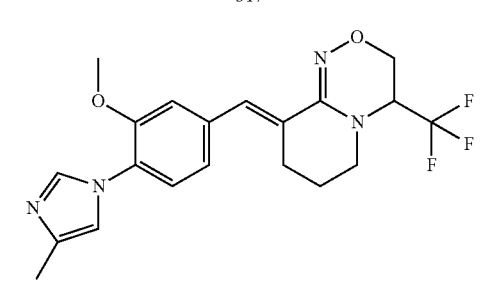<br>Enantiomer II<br>318 | 407.22 | 3.2 | R |

-continued

| Structure | Observed Mass | Rt | Method of Synthesis |
|---|---|---|---|
| Enantiomer I<br>319 | 421.23 | 1.6 | R |
| Enantiomer II<br>320 | 421.23 | 1.6 | R |
| 321 | 498 | | V |
| 322 | 595 | | Aa |

| Structure | Observed Mass | Rt | Method of Synthesis |
|---|---|---|---|
| 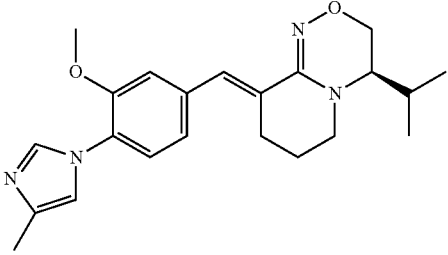 [SMILES: COc1cc(/C=C2\CCCN3C2=NOC[C@H]3C(C)C)ccc1-n1cnc(C)c1]<br>323 | 381 | | R |
| 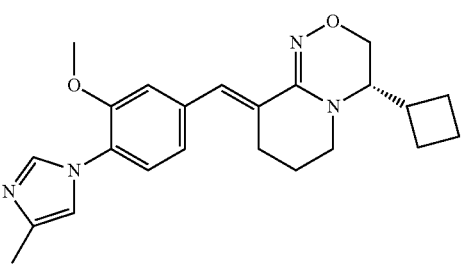 [SMILES: COc1cc(/C=C2\CCCN3C2=NOC[C@@H]3C2CCC2)ccc1-n1cnc(C)c1]<br>324 | 393 | | R |
| 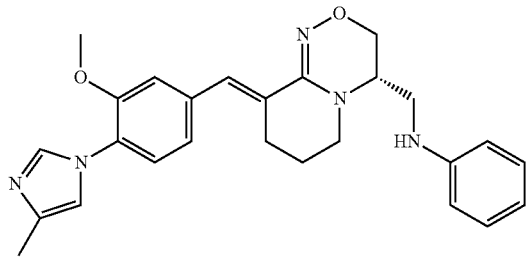 [SMILES: COc1cc(/C=C2\CCCN3C2=NOC[C@@H]3CNc2ccccc2)ccc1-n1cnc(C)c1]<br>325 | 444 | | X |
| 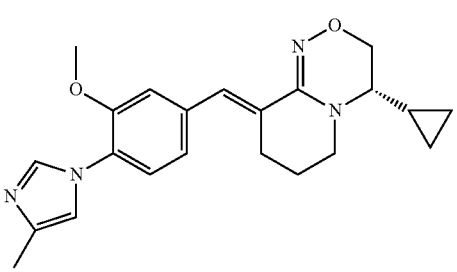 [SMILES: COc1cc(/C=C2\CCCN3C2=NOC[C@@H]3C2CC2)ccc1-n1cnc(C)c1]<br>326 | 379 | | R |

| Structure | Observed Mass | Rt | Method of Synthesis |
|---|---|---|---|
| 327 | 571.31 | 3.4 | R |
| 328 | 481.26 | 3 | U |
| 329 | 481.2 | | U |
| 330 | 571.2 | | R |

-continued
| Structure | Observed Mass | Rt | Method of Synthesis |
|---|---|---|---|
| 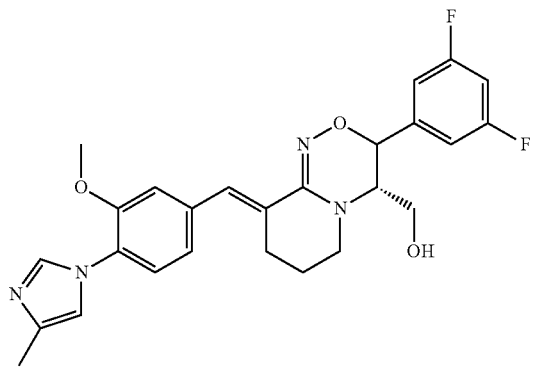 [SMILES: COc1cc(/C=C2\CCCN3C2=NOC(c2cc(F)cc(F)c2)[C@@H]3CO)ccc1-n1cnc(C)c1] 331 | 481.2 | | U |
| 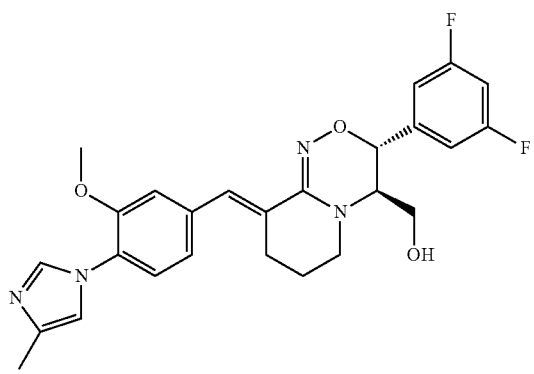 [SMILES: COc1cc(/C=C2\CCCN3C2=NO[C@H](c2cc(F)cc(F)c2)[C@H]3CO)ccc1-n1cnc(C)c1] 332 | 481.2 | | U |
| 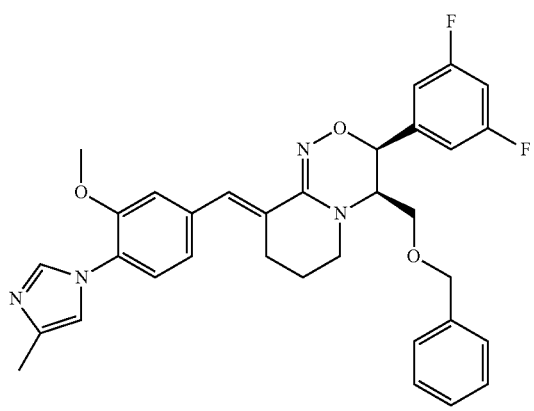 [SMILES: COc1cc(/C=C2\CCCN3C2=NO[C@@H](c2cc(F)cc(F)c2)[C@H]3COCc2ccccc2)ccc1-n1cnc(C)c1] 333 | 571.2 | | R |

| Structure | Observed Mass | Rt | Method of Synthesis |
|---|---|---|---|
| 334 | 465.2 | | Ao |
| 335 | 465.2 | | Ao |
| 336 | 493.2 | | Ao |
| 337 | 475.2 | | Ao |

-continued
| Structure | Observed Mass | Rt | Method of Synthesis |
|---|---|---|---|
| 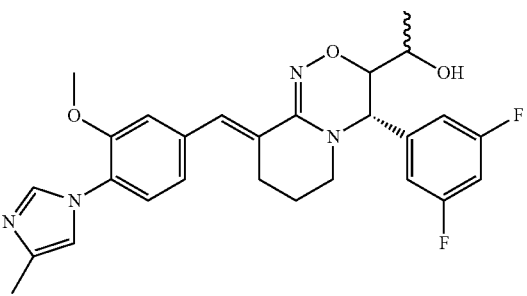 [SMILES: COc1cc(/C=C2\CCCN3C2=NOC(C(C)O)[C@@H]3c2cc(F)cc(F)c2)ccc1-n1cnc(C)c1]<br>338 | 495.2 | | Ao |
| 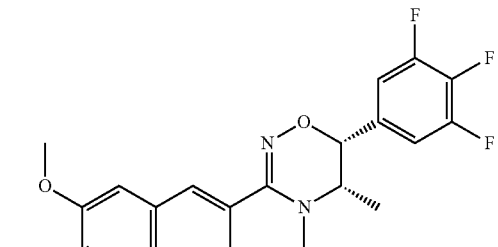<br>339 | 465.2 | | Ao |
| 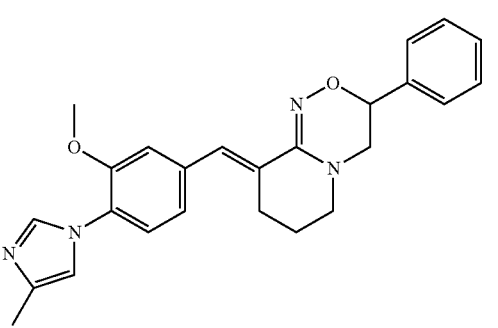 [SMILES: COc1cc(/C=C2\CCCN3CC(c4ccccc4)ON=C23)ccc1-n1cnc(C)c1]<br>Racemic<br>340 | 415.2 | — | R |
| 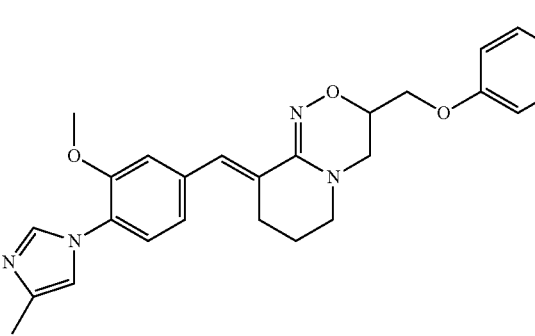<br>Racemic<br>341 | 445.24 | 2.8 | R |

-continued
| Structure | Observed Mass | Rt | Method of Synthesis |
|---|---|---|---|
| 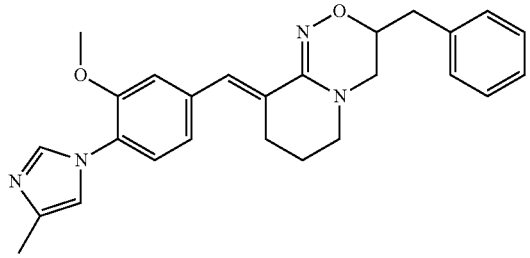 [SMILES: COc1cc(/C=C2\CCCN3CC(Cc4ccccc4)ON=C23)ccc1-n1cnc(C)c1]<br>Racemic<br>342 | 429.24 | 3.2 | R |
| 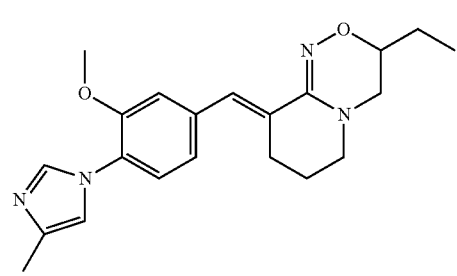 [SMILES: CCC1CN2CCC/C(=C\c3ccc(-n4cnc(C)c4)c(OC)c3)C2=NO1]<br>Racemic<br>343 | 367.2 | 2.4 | R |
| 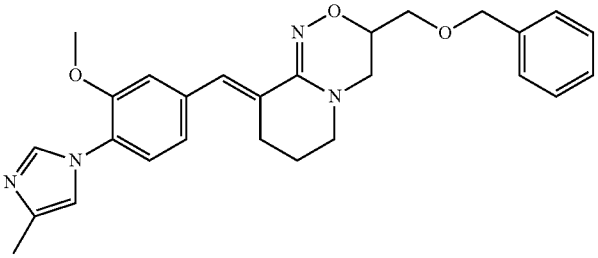 [SMILES: COc1cc(/C=C2\CCCN3CC(COCc4ccccc4)ON=C23)ccc1-n1cnc(C)c1]<br>Racemic<br>344 | 459.25 | 2.8 | R |
| 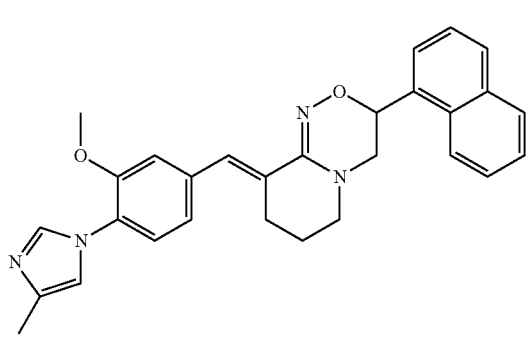 [SMILES: COc1cc(/C=C2\CCCN3CC(c4cccc5ccccc45)ON=C23)ccc1-n1cnc(C)c1]<br>Racemic<br>345 | 465.26 | 3 | R |

-continued

| Structure | Observed Mass | Rt | Method of Synthesis |
|---|---|---|---|
| Racemic 346 | 419.23 | 2.2 | R |
| Enantiomer I 347 | 445.24 | 3.1 | R |
| Enantiomer II 348 | 445.24 | 3.1 | R |
| Enantiomer I 349 | 429.24 | 3 | R |

-continued

| Structure | Observed Mass | Rt | Method of Synthesis |
|---|---|---|---|
| Enantiomer II 350 | 429.24 | 3 | R |
| Enantiomer II 351 | 607.33 | 5 | Ac |
| 352 | 471.26 | 3.1 | Ab |
| 353 | 417.23 | 2.1 | R |

| Structure | Observed Mass | Rt | Method of Synthesis |
|---|---|---|---|
| 354 | 463.25 | 3.4 | Al |
| 355 | 438.24 | 2 | Ak |
| 356 | 466.26 | 2.5 | Ak |
| 357 | 479.26 | 3.3 | Am |
| 358 | 478.26 | 1.4 | Ak |

-continued

| Structure | Observed Mass | Rt | Method of Synthesis |
|---|---|---|---|
| 359 | 452.25 | 1.5 | Ak |
| 360 | 490.27 | 2.7 | Ak |
| 361 | 424.23 | 1.9 | Ak |
| 362 | 511.28 | 3 | Am |
| 363 | 495.27 | 2.3 | Am |

-continued

| Structure | Observed Mass | Rt | Method of Synthesis |
|---|---|---|---|
| 364 | 464.26 | 2.4 | Ak |
| 365 | 450.25 | 2.2 | Ak |
| 366 | 487.27 | 1.7 | Ak |
| 367 | 464.26 | 2.6 | An |

| Structure | Observed Mass | Rt | Method of Synthesis |
|---|---|---|---|
| 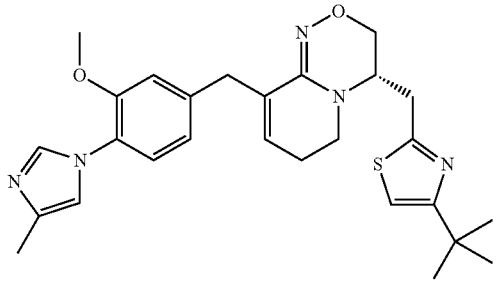 [SMILES: COc1cc(CC2=CCCN3C2=NOC[C@@H]3Cc2nc(C(C)(C)C)cs2)ccc1-n1cnc(C)c1]<br>368 | 492.27 | 3 | An |
| 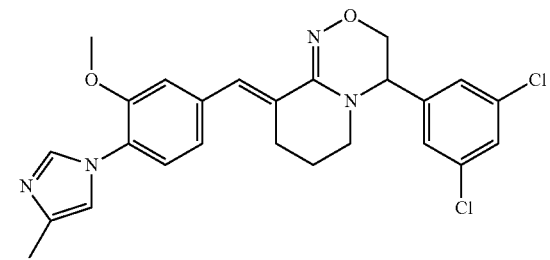 [SMILES: COc1cc(/C=C2\CCCN3C2=NOCC3c2cc(Cl)cc(Cl)c2)ccc1-n1cnc(C)c1]<br>Racemic<br>369 | 484.27 | 3 | R |
| 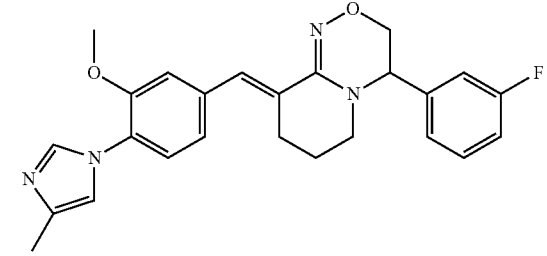 [SMILES: COc1cc(/C=C2\CCCN3C2=NOCC3c2cccc(F)c2)ccc1-n1cnc(C)c1]<br>Racemic<br>370 | 433.24 | 2.6 | R |
| 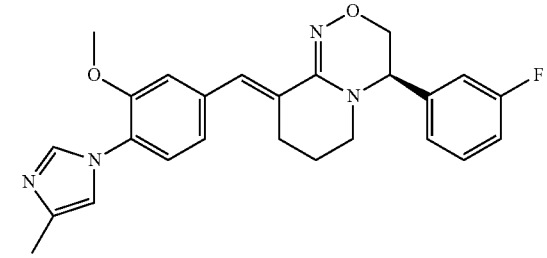 [SMILES: COc1cc(/C=C2\CCCN3C2=NOC[C@H]3c2cccc(F)c2)ccc1-n1cnc(C)c1]<br>371 | 433.24 | 2.6 | R |
| 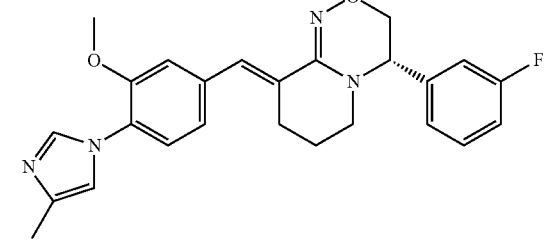<br>372 | 433.24 | 2.6 | R |

-continued
| Structure | Observed Mass | Rt | Method of Synthesis |
|---|---|---|---|
| 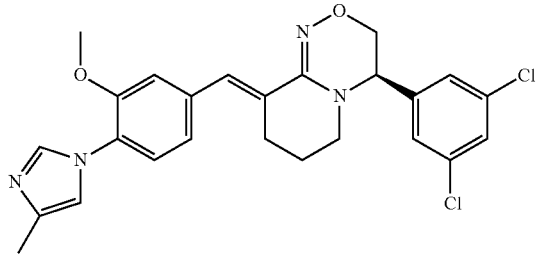 [SMILES: COc1cc(/C=C2\CCCN3C2=NOC[C@H]3c2cc(Cl)cc(Cl)c2)ccc1-n1cnc(C)c1] 373 | 484.27 | 3 | R |
| 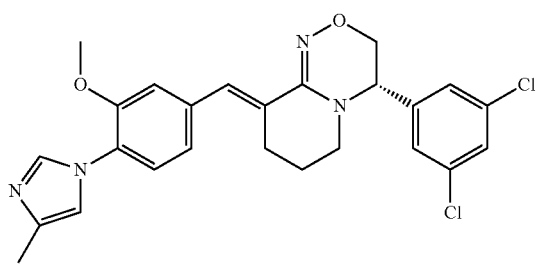 [SMILES: COc1cc(/C=C2\CCCN3C2=NOC[C@@H]3c2cc(Cl)cc(Cl)c2)ccc1-n1cnc(C)c1] 374 | 484.27 | 3 | R |
| 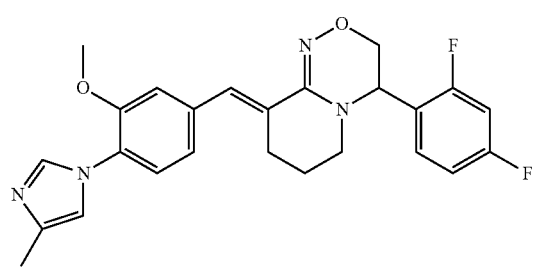 [SMILES: COc1cc(/C=C2\CCCN3C2=NOCC3c2ccc(F)cc2F)ccc1-n1cnc(C)c1] Racemic 375 | 451.25 | 2.7 | R |
| 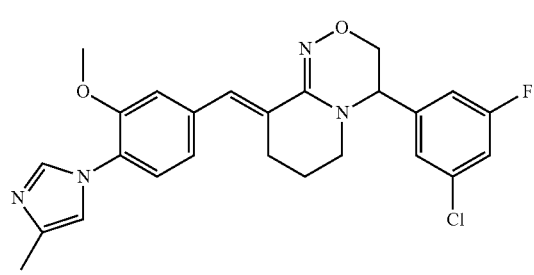 Racemic 376 | 467.26 | 2.7 | R |

-continued

| Structure | Observed Mass | Rt | Method of Synthesis |
|---|---|---|---|
| 377 | 447.25 | 2.7 | R |
| 378 | 451.25 | 2.7 | R |
| 379 | 467.26 | 2.9 | R |
| 380 | 467.26 | 2.9 | R |
| 381 | 451.25 | 2.6 | R |

| Structure | Observed Mass | Rt | Method of Synthesis |
|---|---|---|---|
| 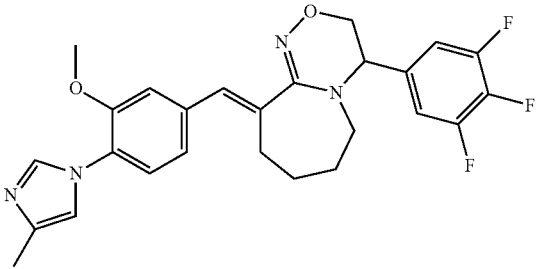 [SMILES: COc1cc(/C=C2\CCCCN3C2=NOCC3c2cc(F)c(F)c(F)c2)ccc1-n1cnc(C)c1]<br>Racemic<br>382 | 483.27 | 3.6 | R |
| 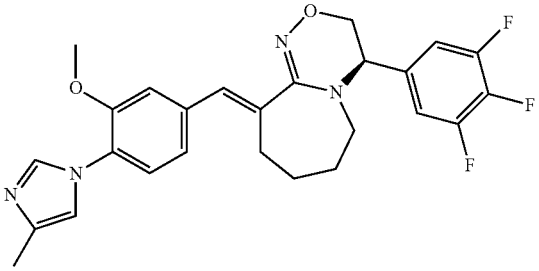 [SMILES: COc1cc(/C=C2\CCCCN3C2=NOC[C@H]3c2cc(F)c(F)c(F)c2)ccc1-n1cnc(C)c1]<br>383 | 483.27 | 3.6 | R |
| 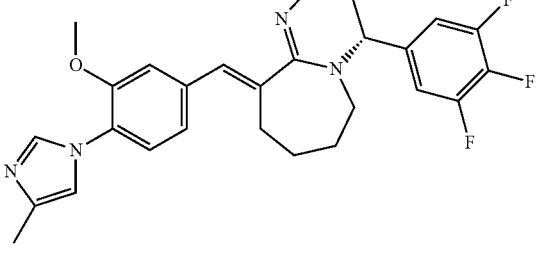<br>384 | 483.27 | 3.6 | R |
| 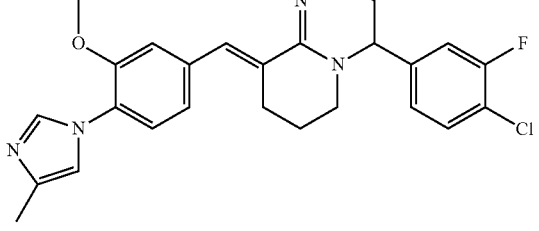<br>385 | 467.26 | 3.4 | R |

-continued
| Structure | Observed Mass | Rt | Method of Synthesis |
|---|---|---|---|
| 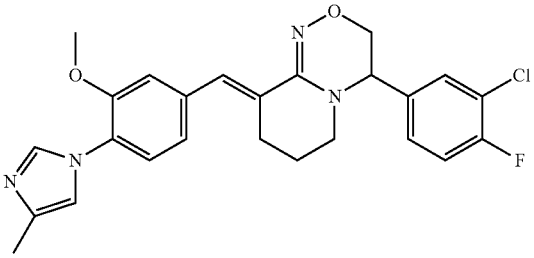 [SMILES: COc1cc(/C=C2\CCCN3C2=NOCC3c2ccc(F)c(Cl)c2)ccc1-n1cnc(C)c1]<br>386 | 467.26 | 2 | R |
| 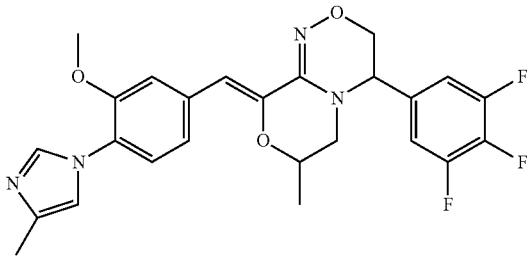 [SMILES: COc1cc(/C=C2\OC(C)CN3C2=NOCC3c2cc(F)c(F)c(F)c2)ccc1-n1cnc(C)c1]<br>Diastereomer I<br>387 | 485.27 | 3.2 | Aq |
| 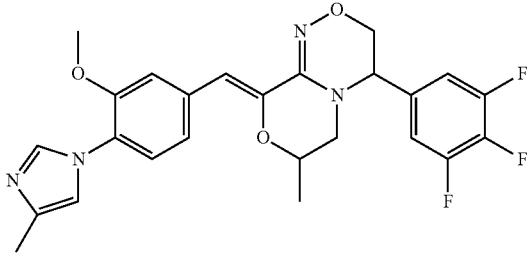 [SMILES: COc1cc(/C=C2\OC(C)CN3C2=NOCC3c2cc(F)c(F)c(F)c2)ccc1-n1cnc(C)c1]<br>Diastereomer II<br>388 | 485.27 | 4.2 | Aq |
| 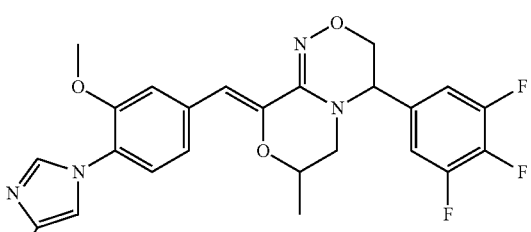<br>Diastereomer III<br>389 | 485.27 | 4.2 | Aq |
| 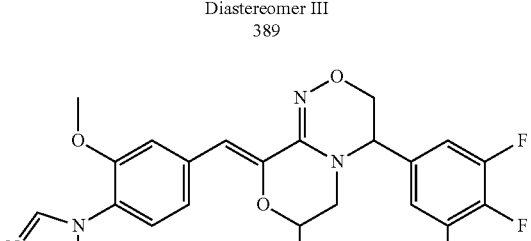<br>Diastereomer IV<br>390 | 485.27 | 4.2 | Aq |

| Structure | Observed Mass | Rt | Method of Synthesis |
|---|---|---|---|
| 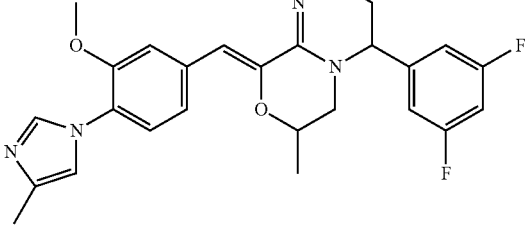<br>Diastereomer I<br>391 | 467.3 | | Aq |
| 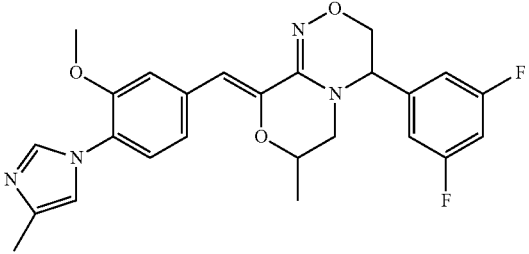 [SMILES: COc1cc(/C=C2\OC(C)CN3C2=NOCC3c2cc(F)cc(F)c2)ccc1-n1cnc(C)c1]<br>Diastereomer II<br>392 | 467.3 | | Aq |
| 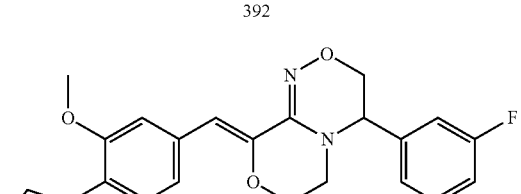<br>Diastereomer III<br>393 | 467.3 | | Aq |
| 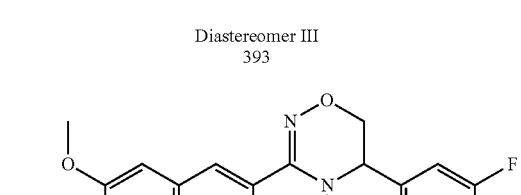<br>Diastereomer IV<br>394 | 467.3 | | Aq |

Assay:

Secretase Reaction and Aβ Analysis in Whole Cells: HEK293 cells overexpressing APP with Swedish and London mutations were treated with the specified compounds for 5 hour at 37° C. in 100 ml of DMEM medium containing 10% fetal bovine serum. At the end of the incubation, total Aβ, Aβ40 and Aβ42 were measured using electrochemiluminescence (ECL) based sandwich immunoassays. Total Aβ was determined using a pair of antibodies TAG-W02 and biotin-4G8, Aβ40 was identified with antibody pairs TAG-G2-10 and biotin-4G8, while Aβ42 was identified with TAG-G2-11 and biotin-4G8. The ECL signal was measured using Sector Imager 2400 (Meso Scale Discovery).

MS Analysis of Aβ Profile: Aβ profile in conditioned media was determined using surface enhanced laser desorption/ionization (SELDI) mass spectrometry. Conditioned media was incubated with antibody W02 coated PS20 ProteinChip array. Mass spectra of Aβ captured on the array were read on SELDI ProteinChip Reader (Bio-Rad) according to manufacture's instructions.

CSF Aβ Analysis: Aβ in rat CSF was determined using MSD technology as described above. Aβ40 was measured using antibody pair Tag-G2-10 and biotin-4G8, while Aβ42 was measured using Tag-anti Aβ42 (Meso Scale Discovery) and biotin-4G8. The ECL signal was measured using Sector imager 2400 (Meso Scale Discovery).

Matrix-assisted laser desorption/ionization mass spectrometric (MALDI MS) analysis of Aβ is performed on a Voyager-DE STR mass spectrometer (ABI, Framingham, Mass.). The instrument is equipped with a pulsed nitrogen laser (337 nm). Mass spectra are acquired in the linear mode with an acceleration voltage of 20 kV. Each spectrum presented in this work represents an average of 256 laser shots. To prepare the sample-matrix solution, 1 μL of immunoprecipitated Aβ sample is mixed with 3 μL of saturated α-cyano-4-hydroxycinnamic acid solution in 0.1% TFA/acetonitrile. The sample-matrix solution is then applied to the sample plate and dried at ambient temperature prior to mass spectrometric analysis. All the spectra are externally calibrated with a mixture of bovine insulin and ACTH (18-39 clip).

Certain compounds of the invention had an Ab42 $IC_{50}$ within the range of about 11.4 nM to about 20,000 nM.

Certain compounds of the invention had an Ab42 $IC_{50}$ within the range of about 11.4 nM to about 97 nM.

Certain compounds of the invention had Abtotal/Ab42 ratio within the range of about 1 to 1222.

Certain compounds of the invention had Abtotal/Ab42 ratio within the range of about 205 to 602.

While the present invention has been described in conjunction with the specific embodiments set forth above, many alternatives, modifications and other variations thereof will be apparent to those of ordinary skill in the art. All such alternatives, modifications and variations are intended to fail within the spirit and scope of the present invention.

What is claimed is:

1. A compound selected from the group consisting of compounds of,

Q11

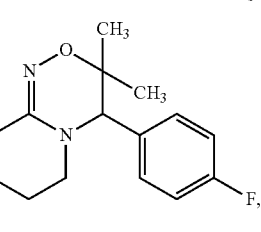

R4

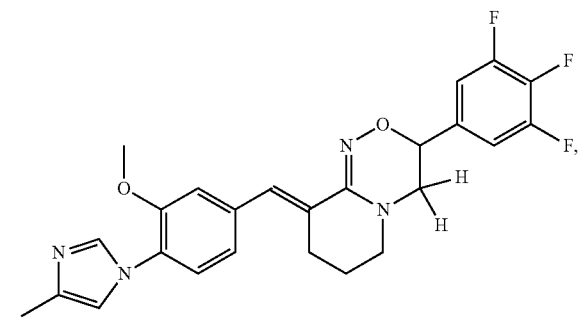

U2

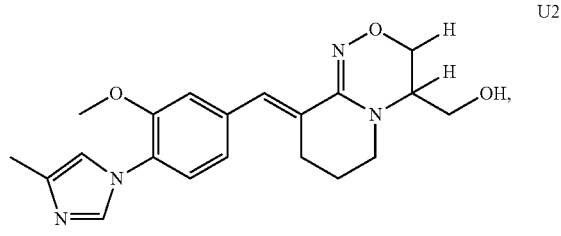

W3

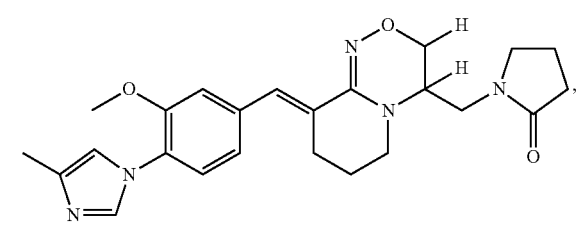

X2

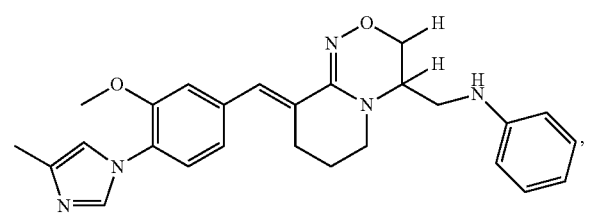

Y3

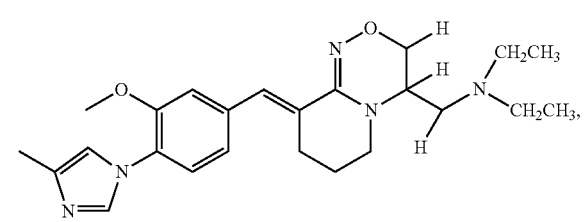

Z2

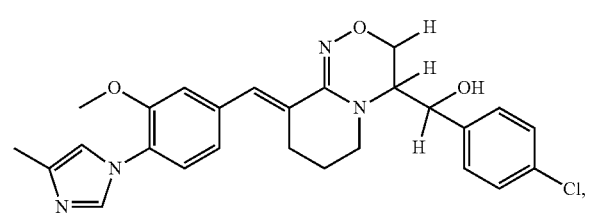

Aa2
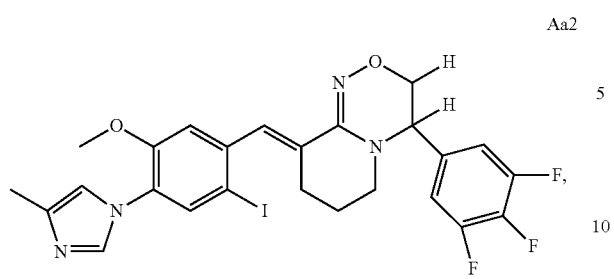
Ab2
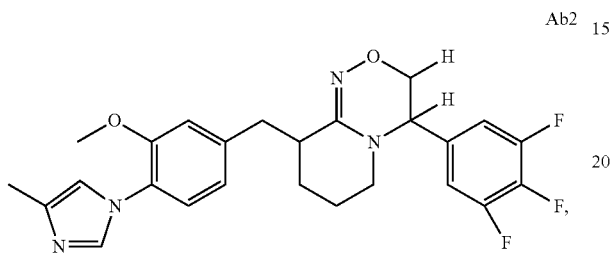
aC6
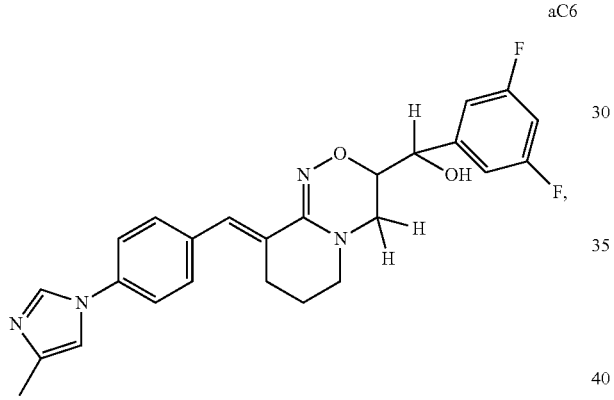
Af3
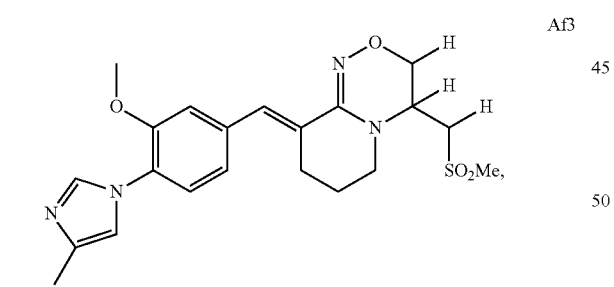
Ag4
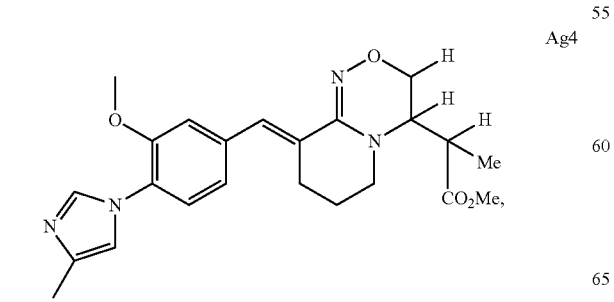
Ah2
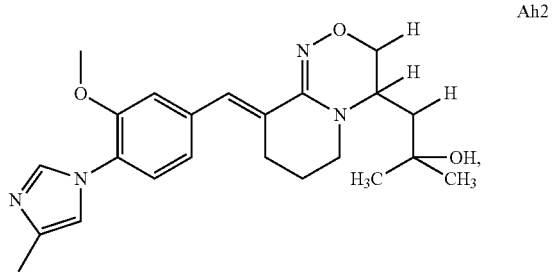
Ai2
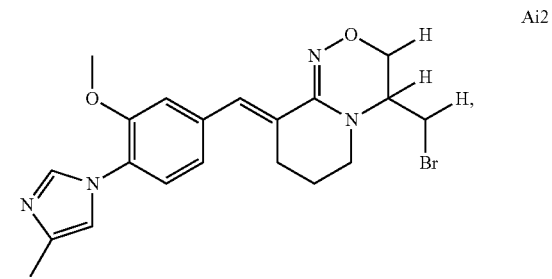
Aj4
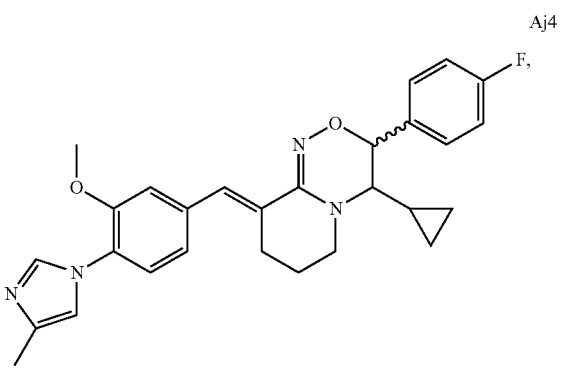
Ak2
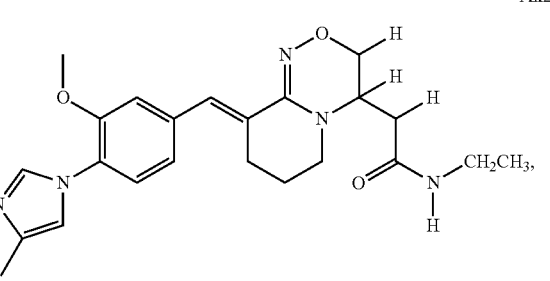
Al2
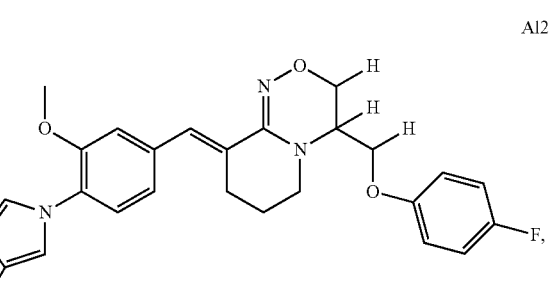

Am3
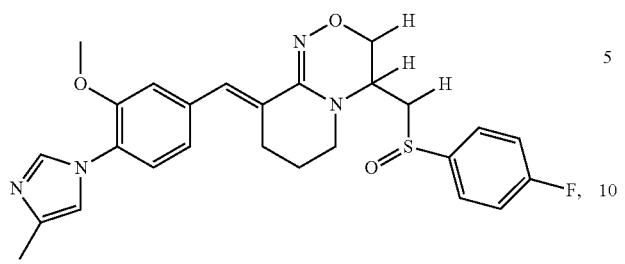
Am4
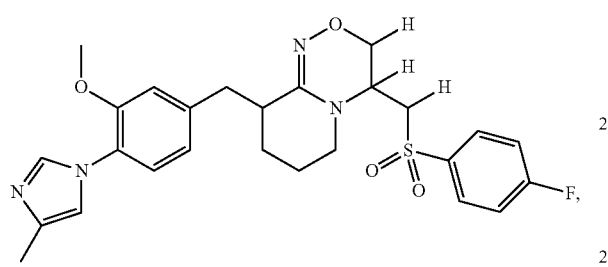
An4
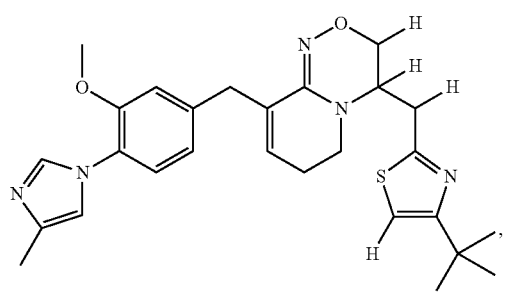
Ao5
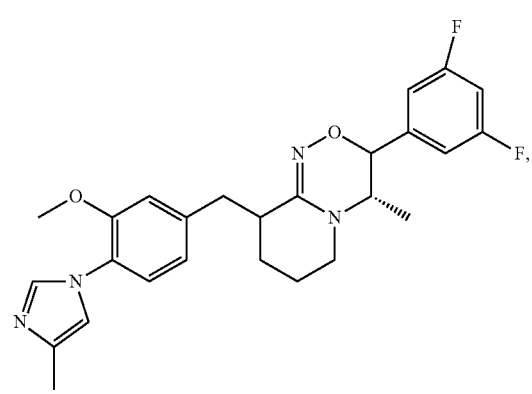
Ap15
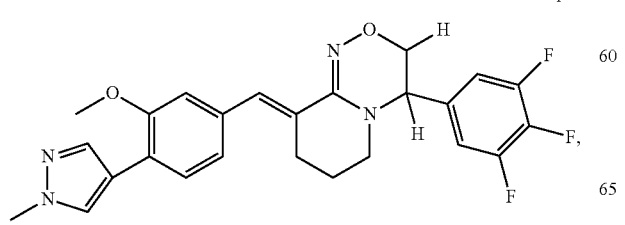
Aq7
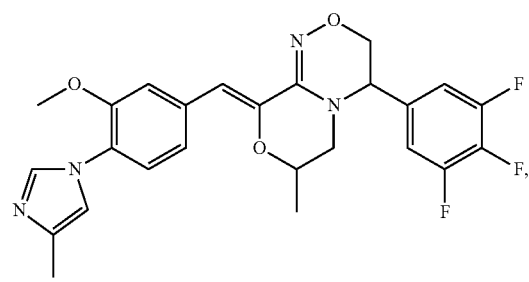
Ar3
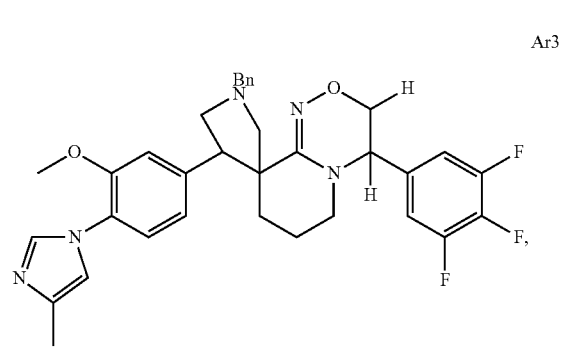
201
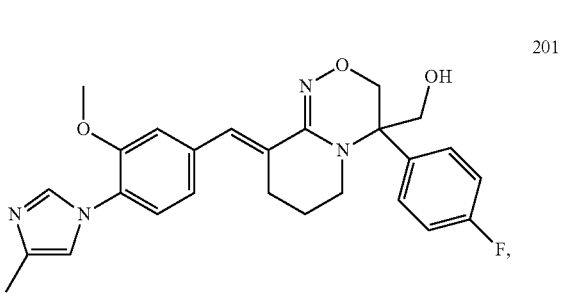
racemic
203
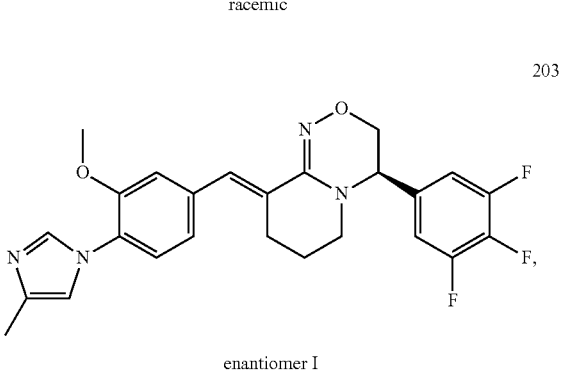
enantiomer I
206
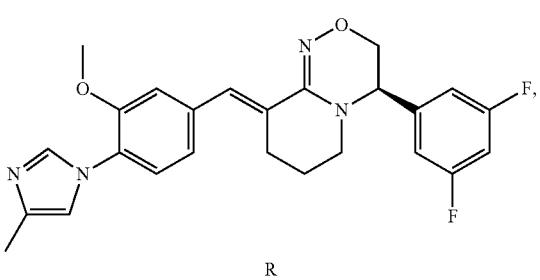
R 181
-continued
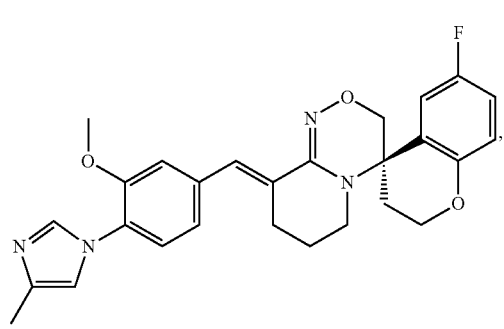
207
enantiomer I
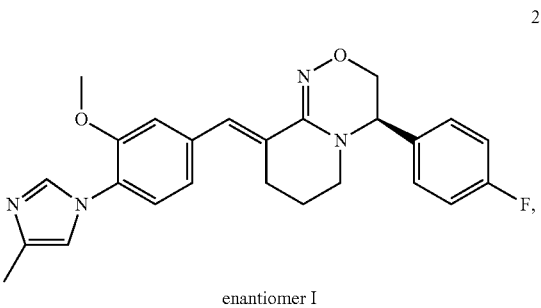
208
enantiomer I
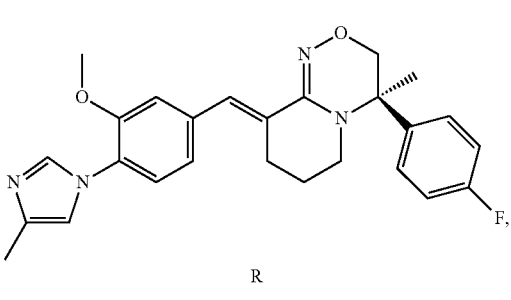
209
R
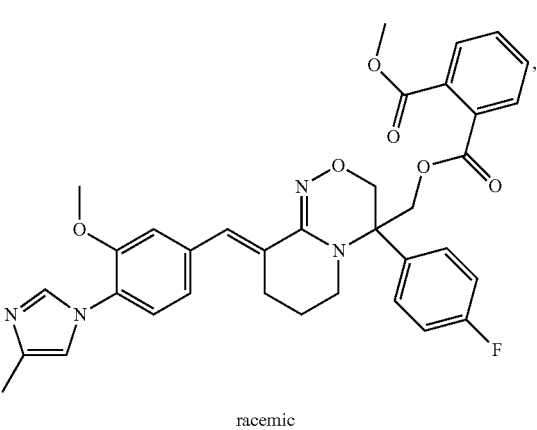
210
racemic
182
-continued
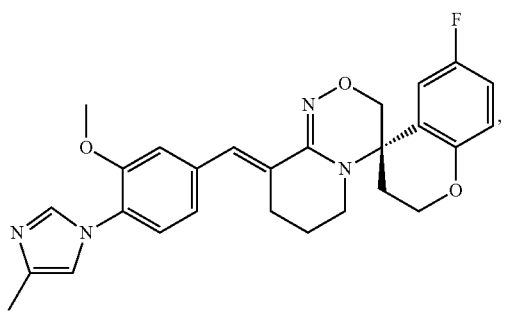
211
enantiomer II
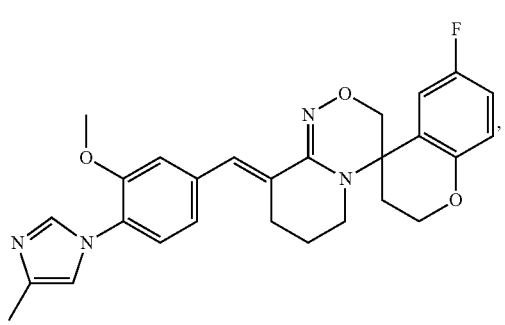
212
racemic
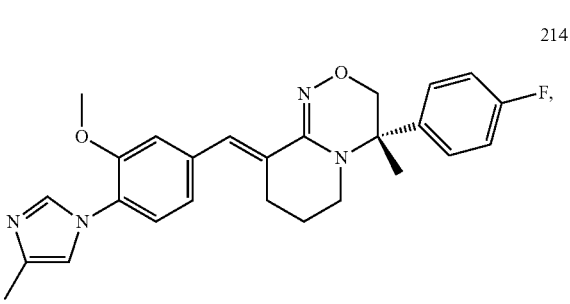
214
S
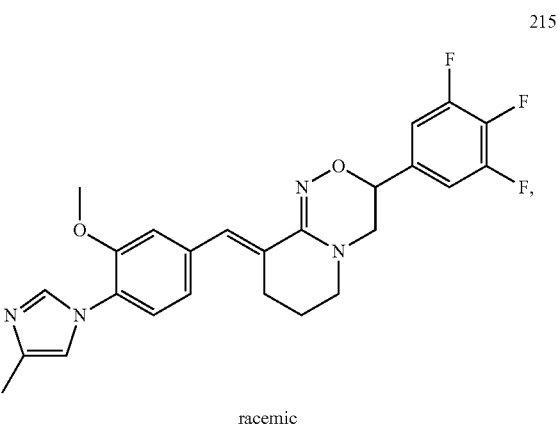
215
racemic 220
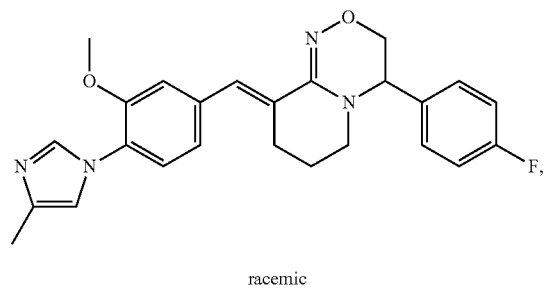
racemic
221
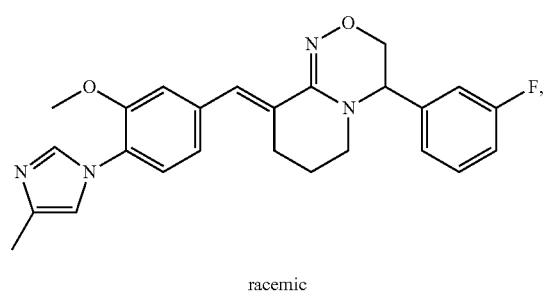
racemic
222
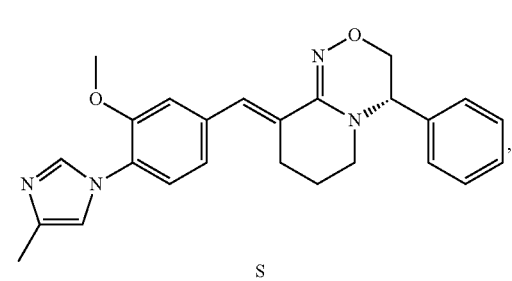
S
226
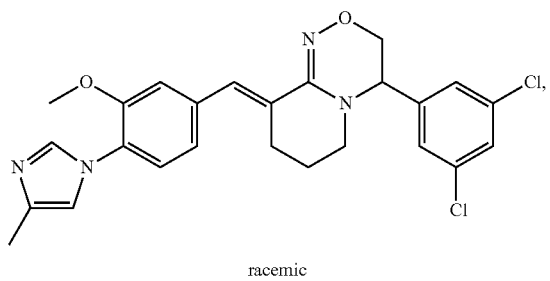
racemic
227
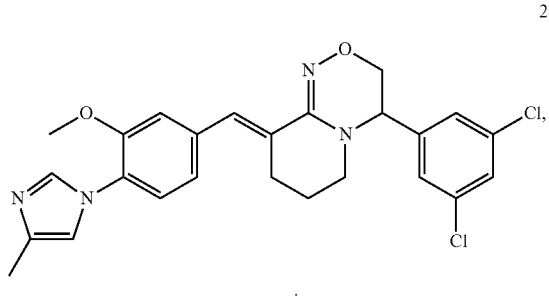
S
229
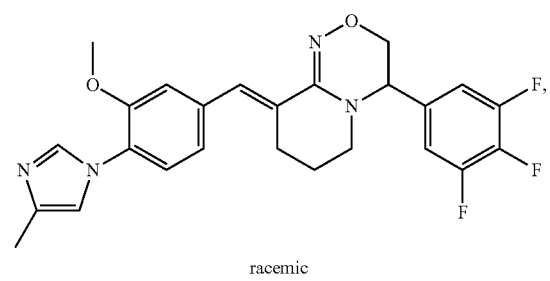
racemic
231
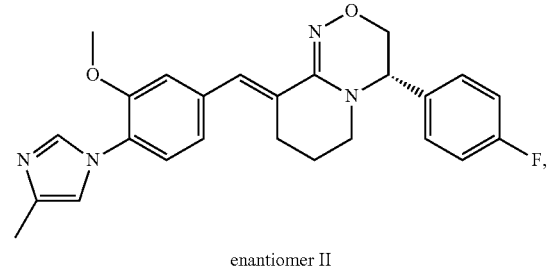
enantiomer II
233
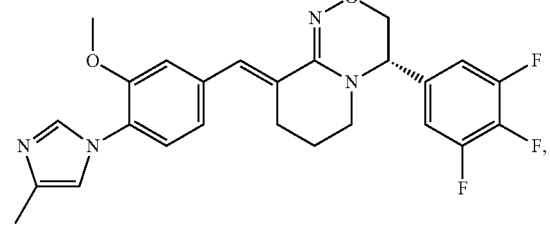
enantiomer II
245
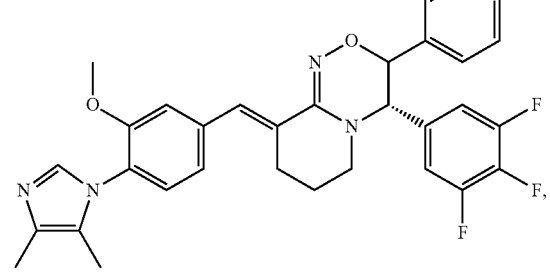
246
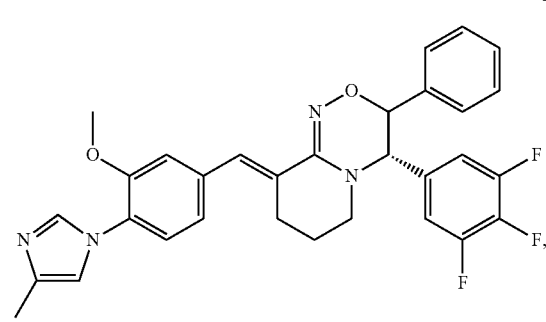

247
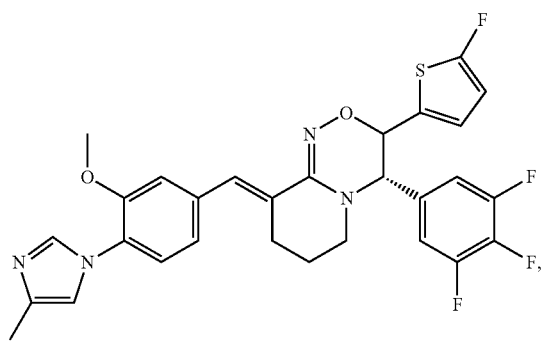
248
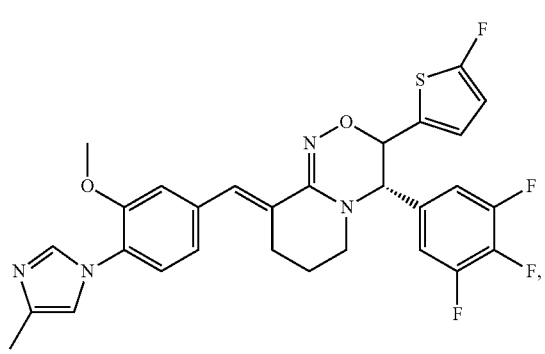
249
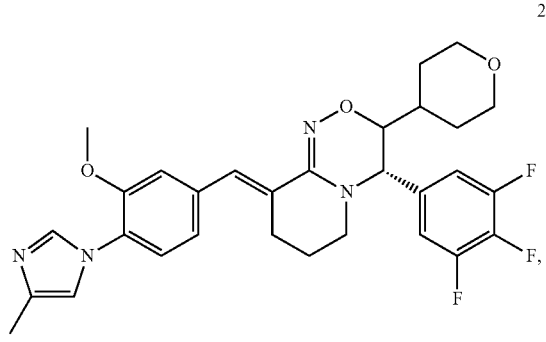
250
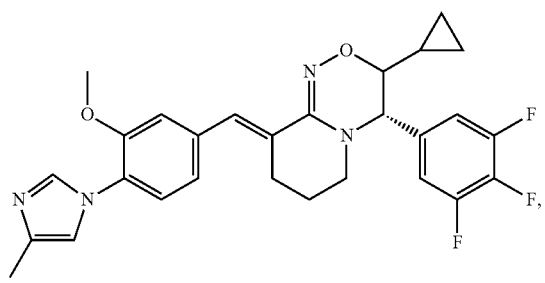
251
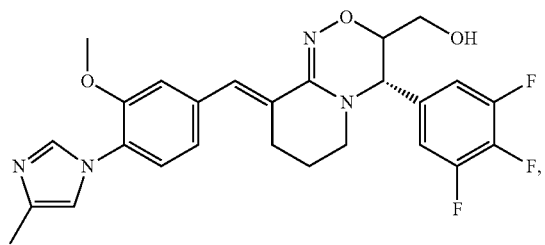
252
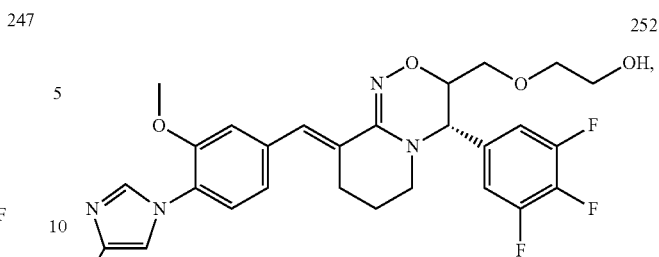
253
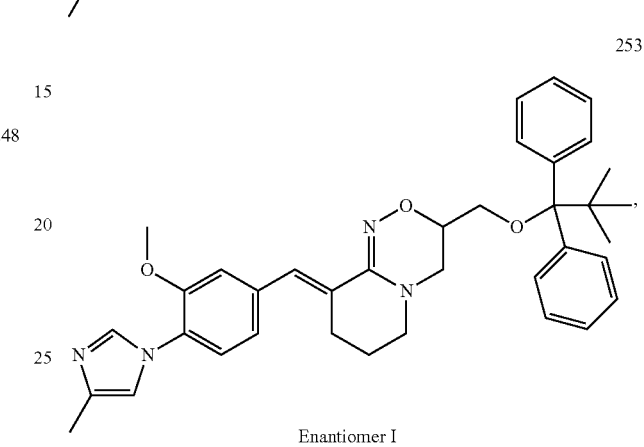
Enantiomer I
254
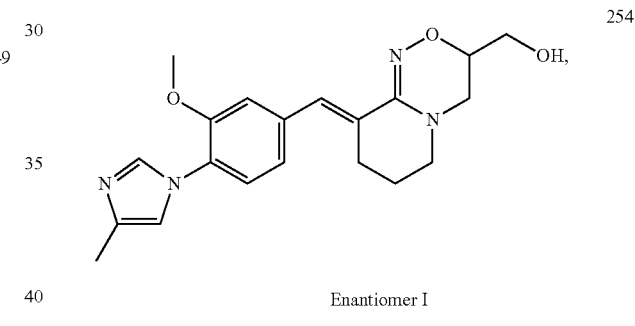
Enantiomer I
255
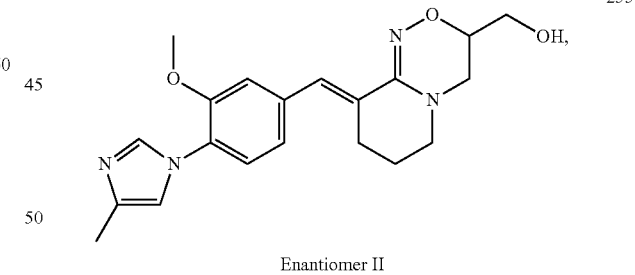
Enantiomer II
256
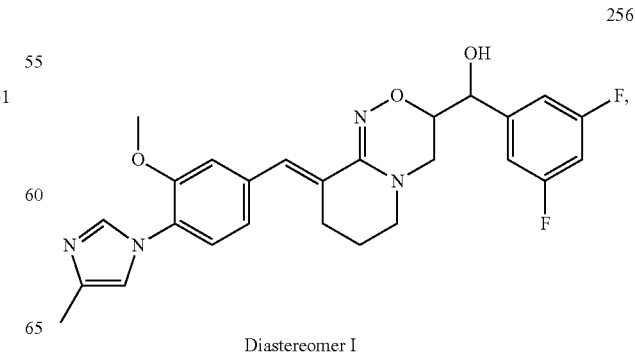
Diastereomer I 257
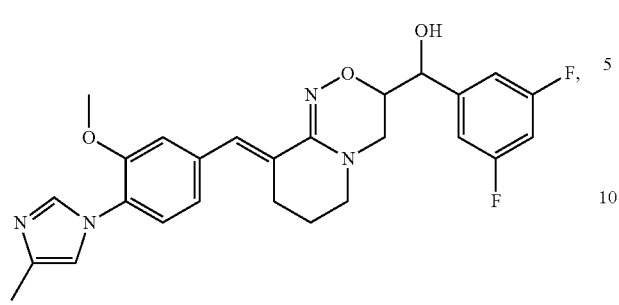
Diastereomer II
258
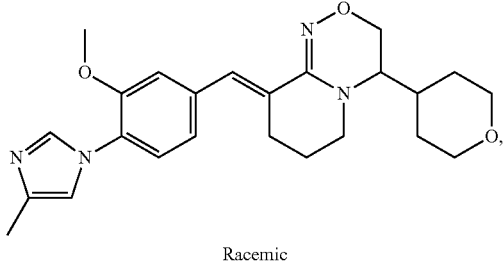
259
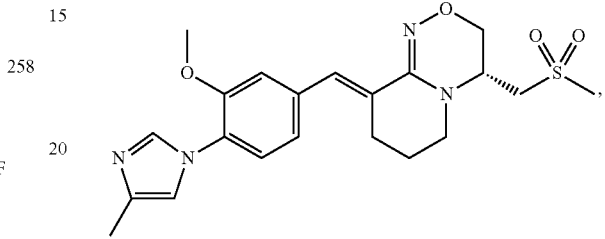
260
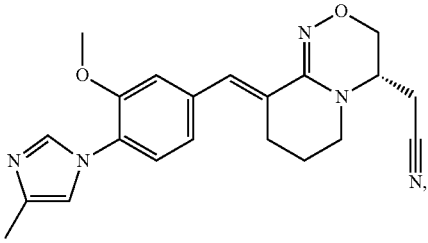
261
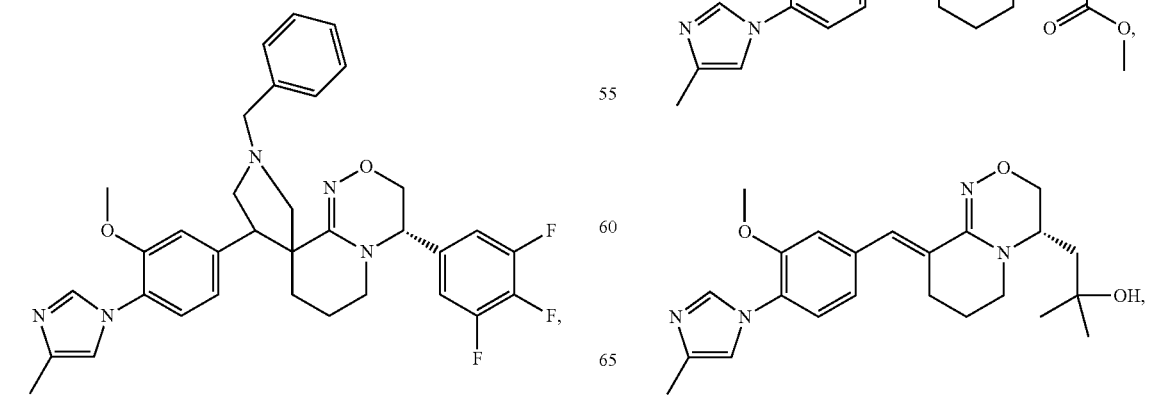
262
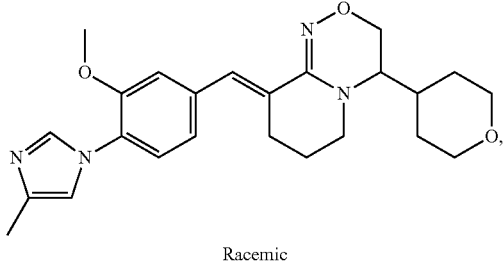
Racemic
263
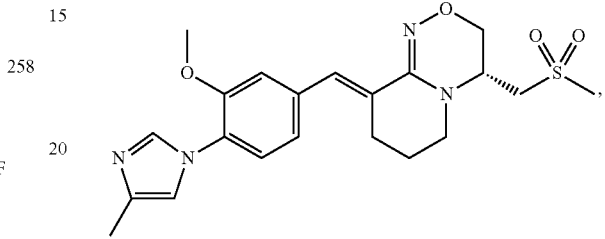
264
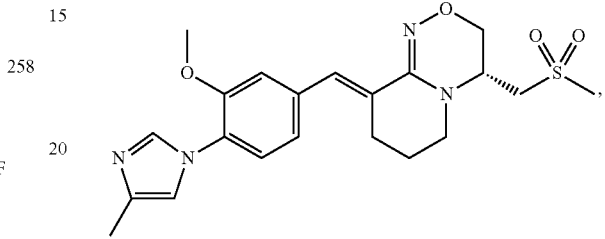
265
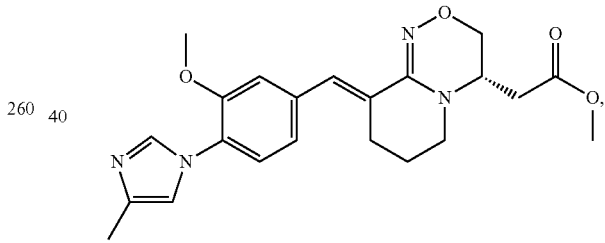
266
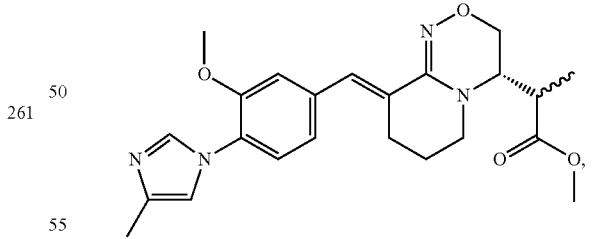
267
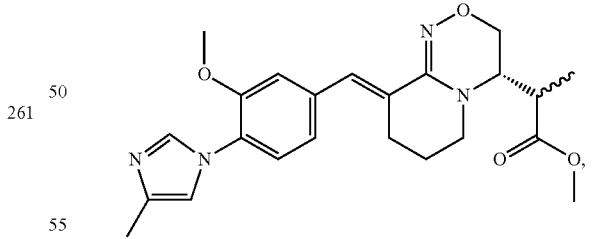

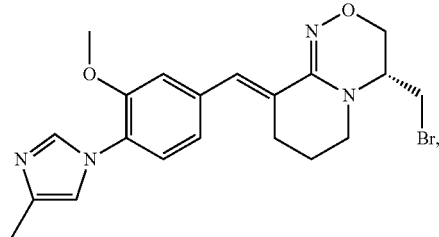
268
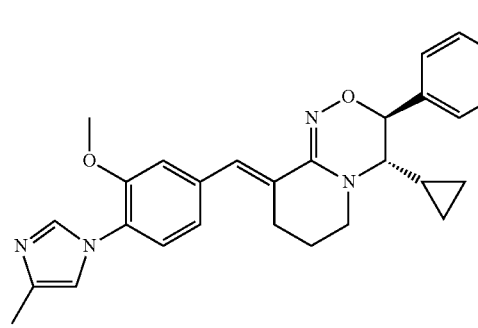
269
270
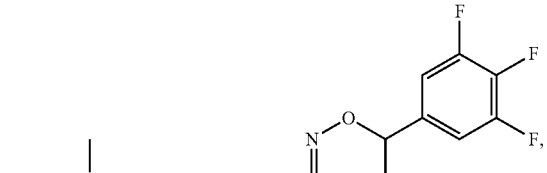
273
Racemic
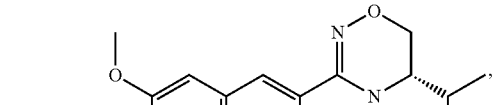
274
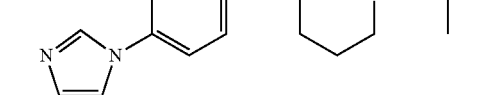
275
271
276
272
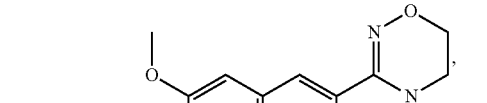
277
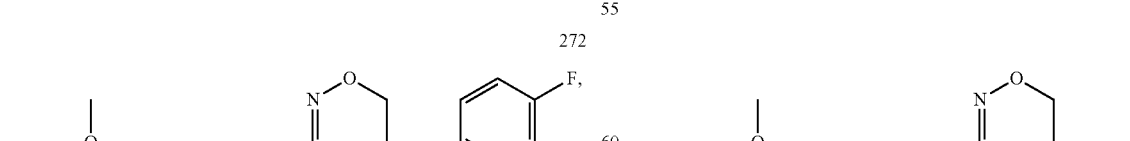

278
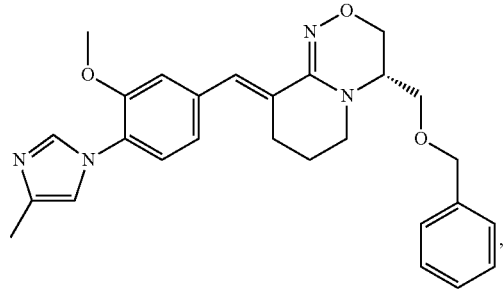
279
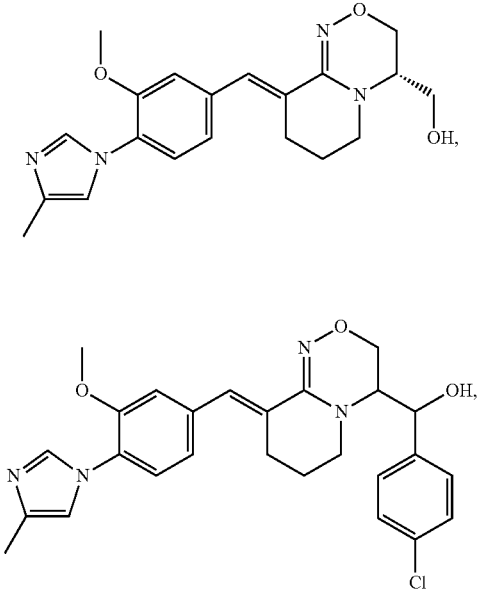
Diastereomer I
281
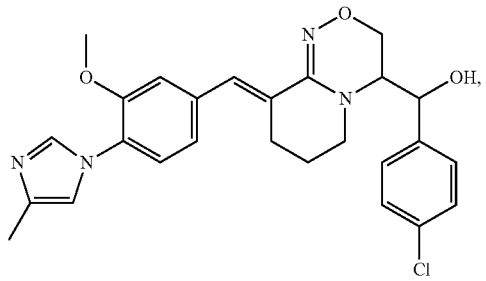
Diastereomer II
282
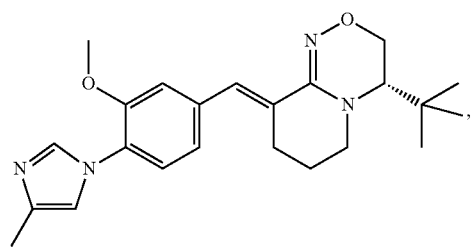
283
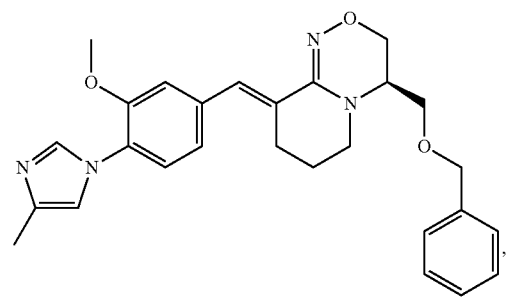
284
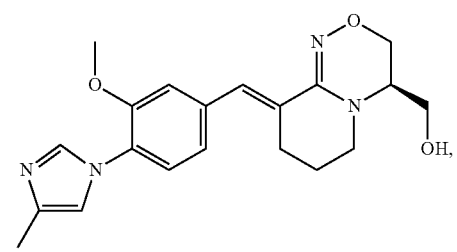
285
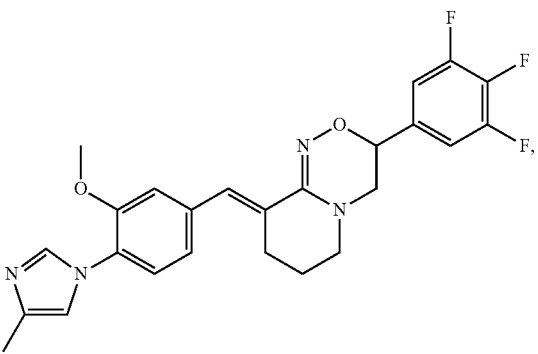
Enantiomer I
286
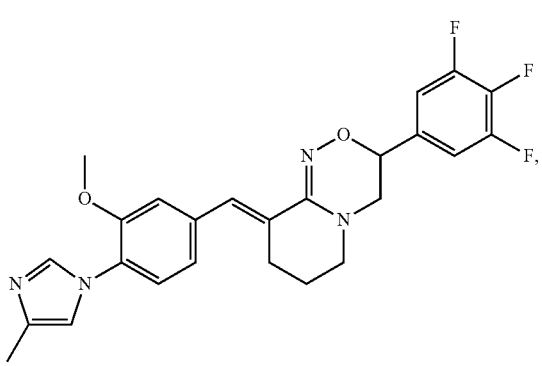
Enantiomer II
287
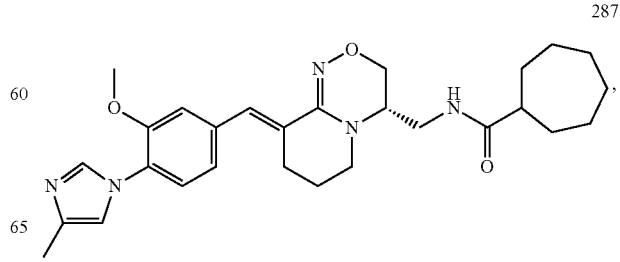

288
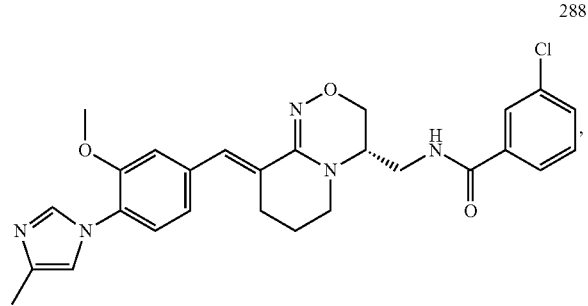
289
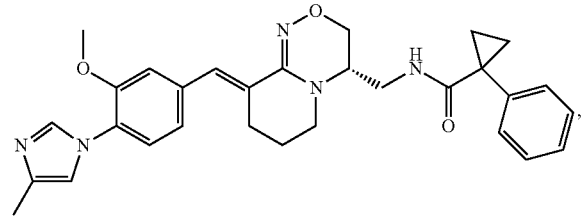
290
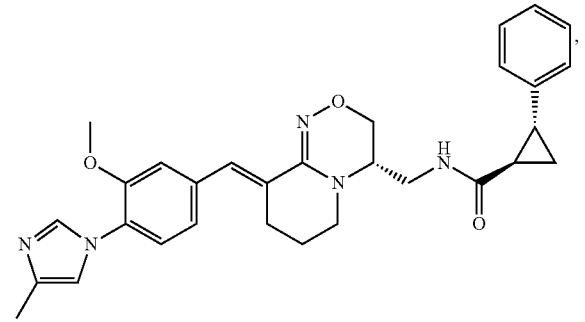
291
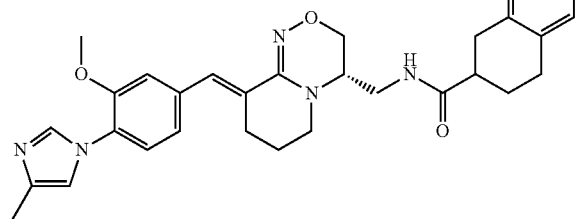
292
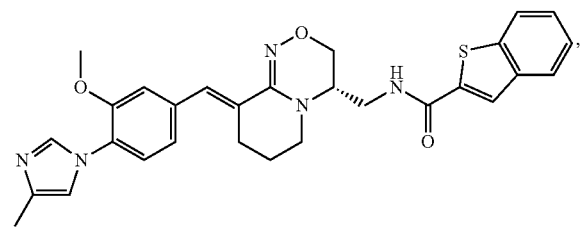
293
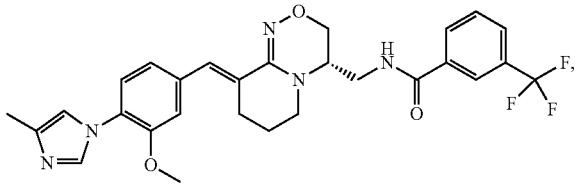
294
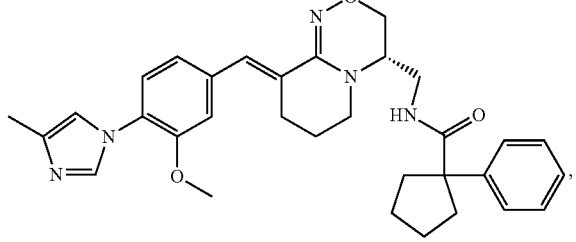
295
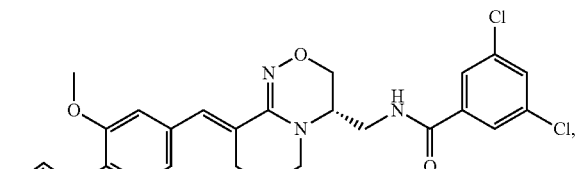
296
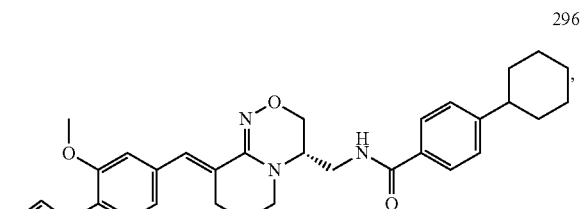
297
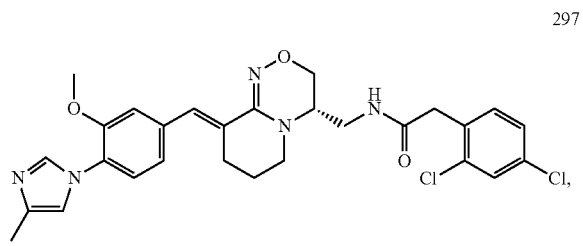
298
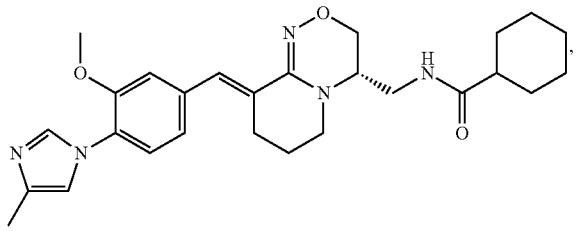

299
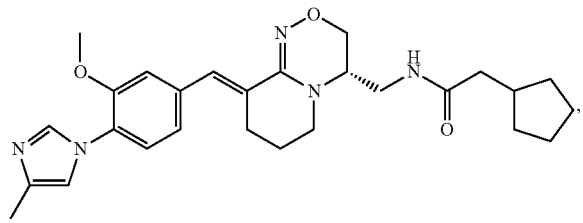
300
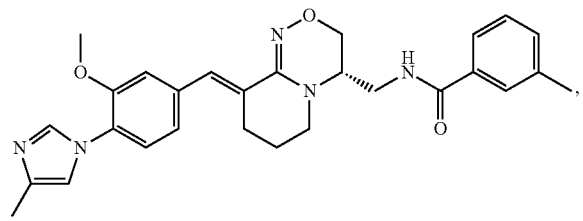
301
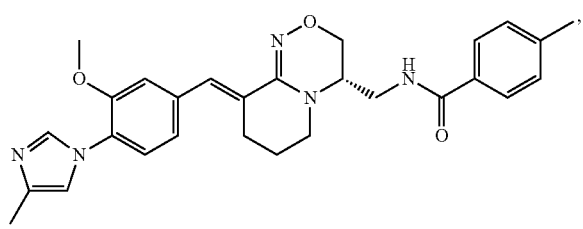
302
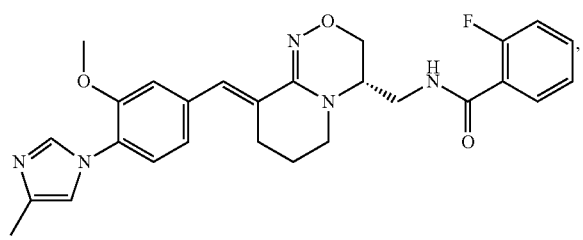
303
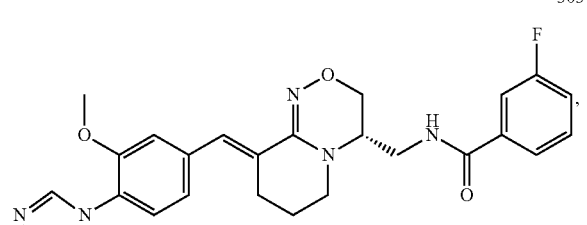
304
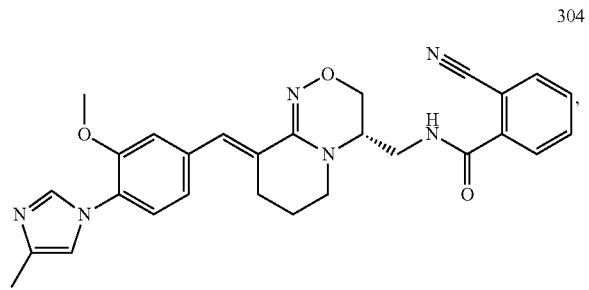
305
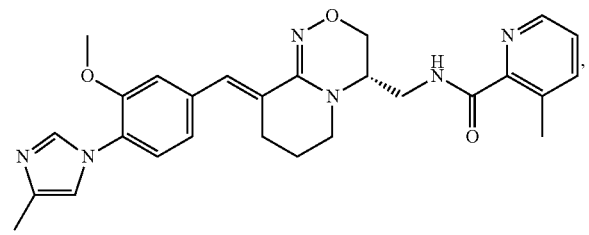
306
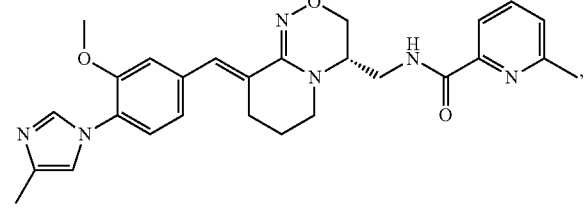
307
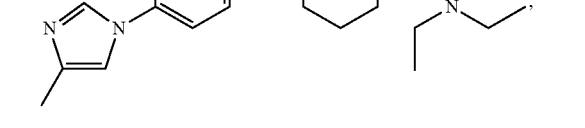
308
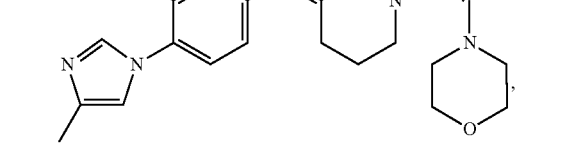
309
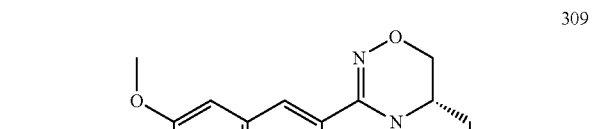
310
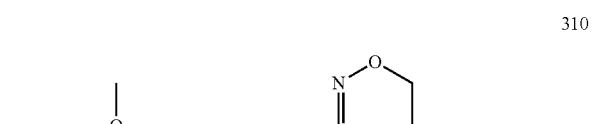

311
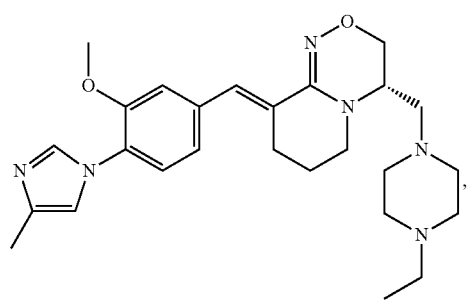
312
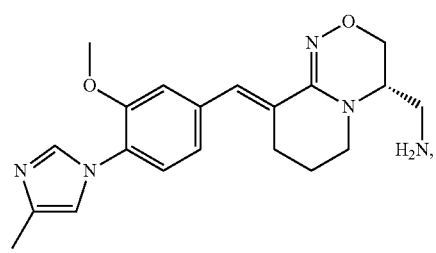
313
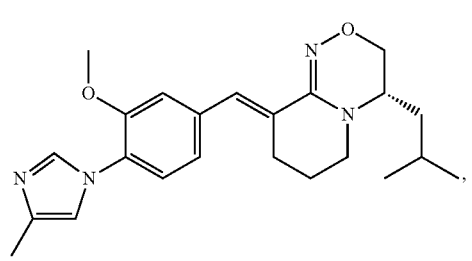
314
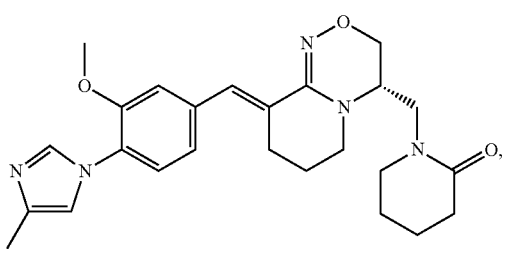
315
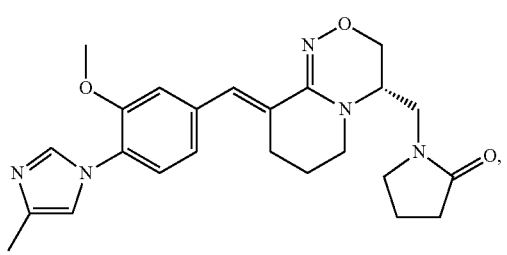
316
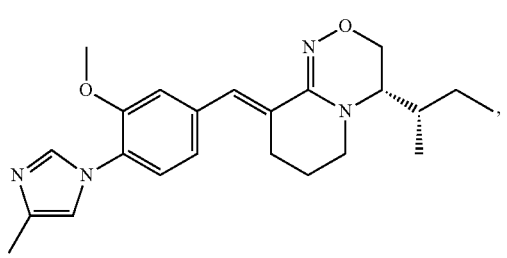
317
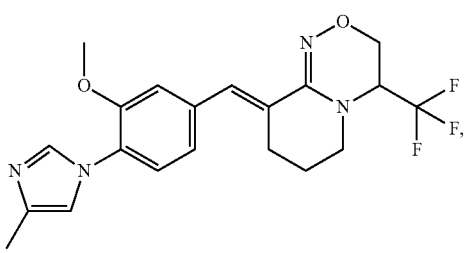
Enantiomer I
318
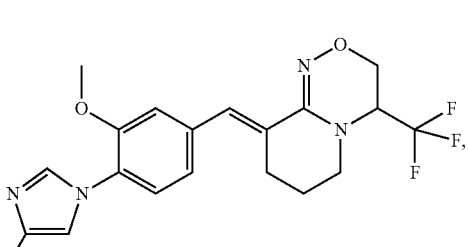
Enantiomer II
319
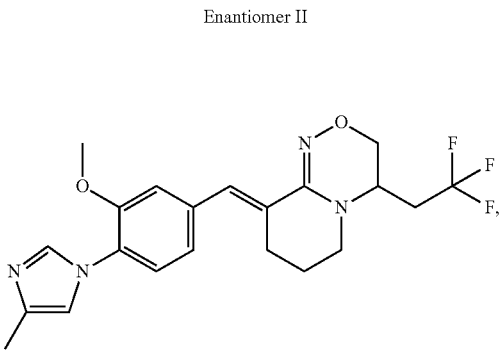
Enantiomer I
320
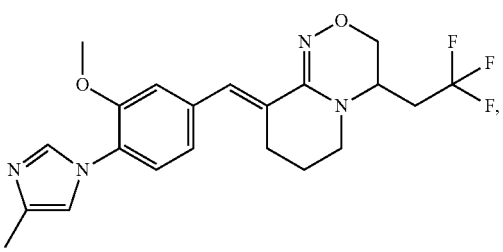
Enantiomer II
321
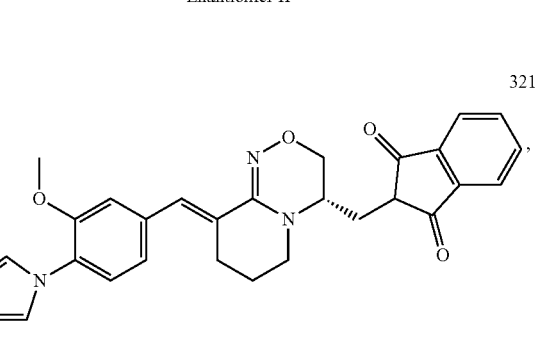

322 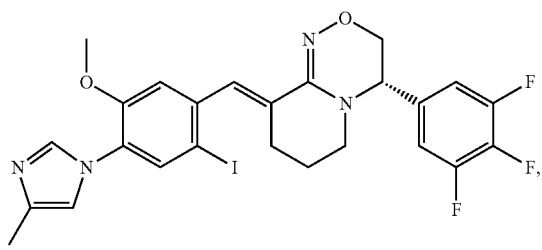
323 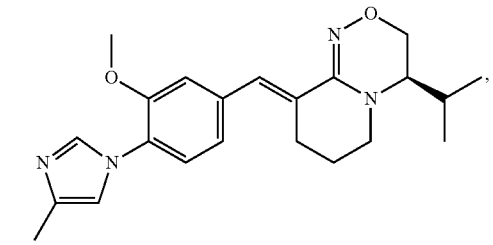
324 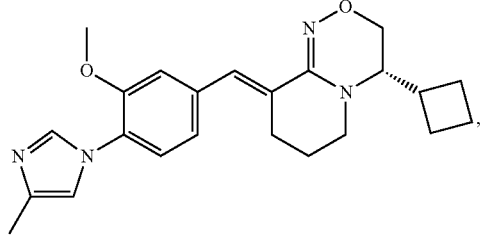
325 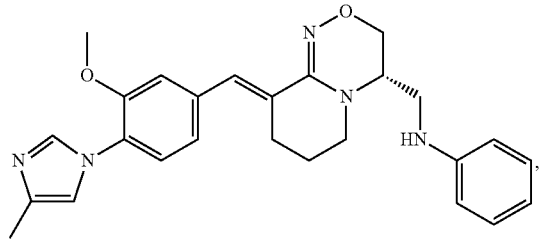
326 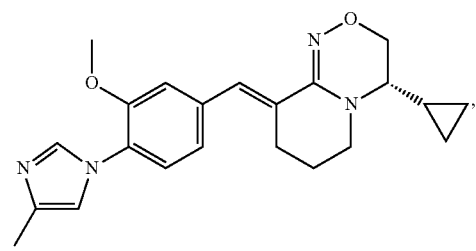
327 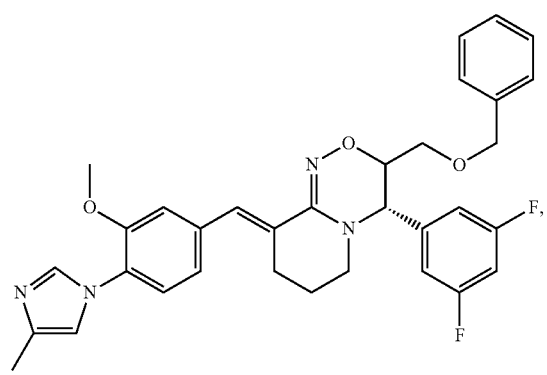
328 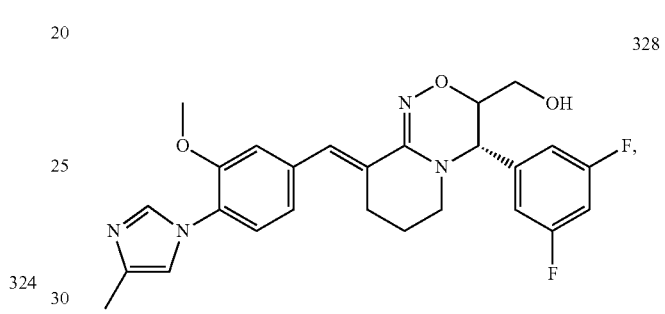
329 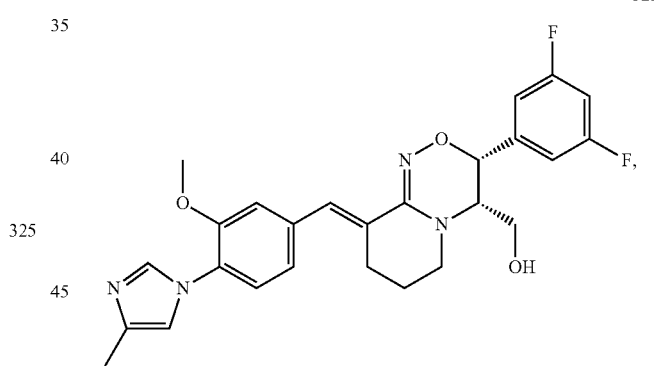
330 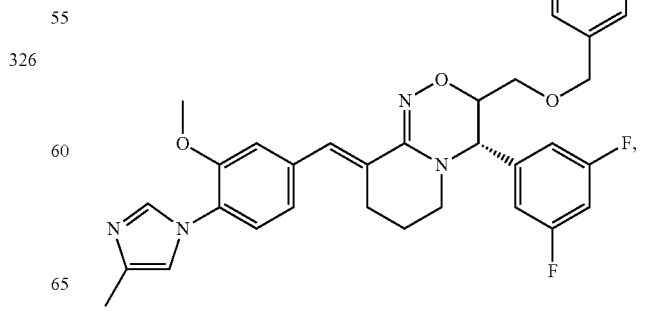

331
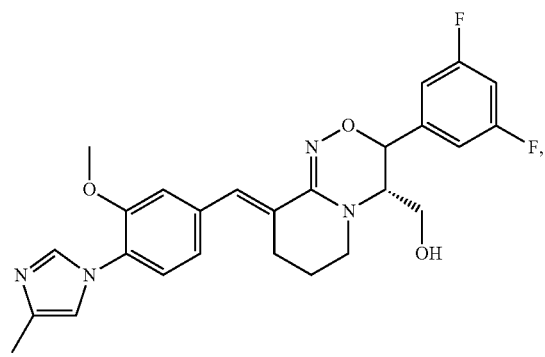
332
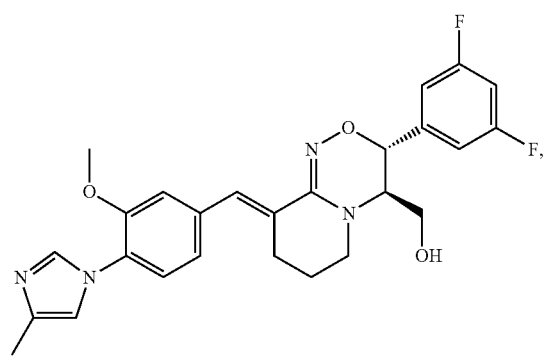
333
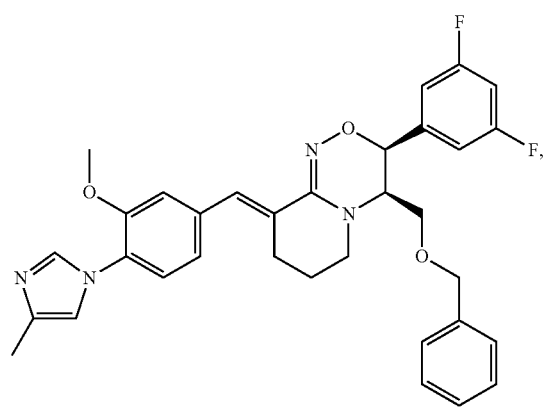
334
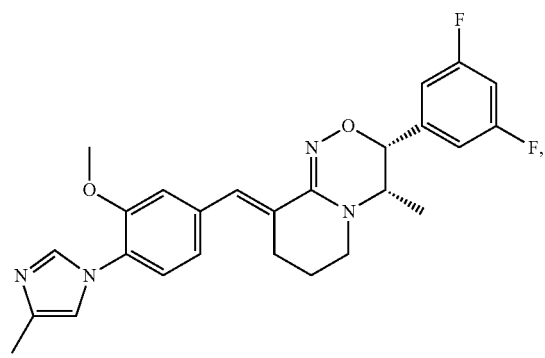
335
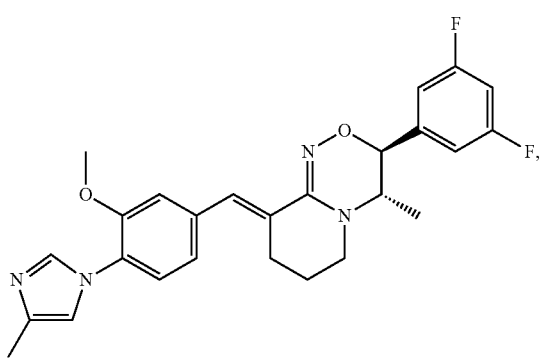
336
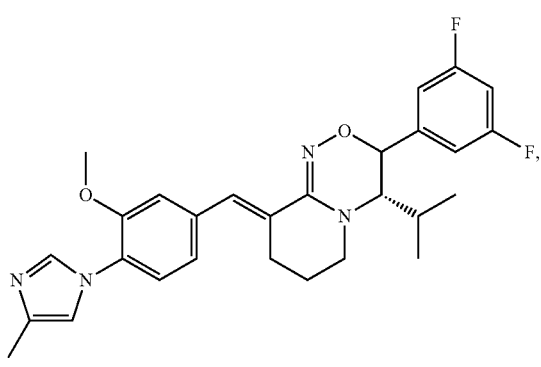
337
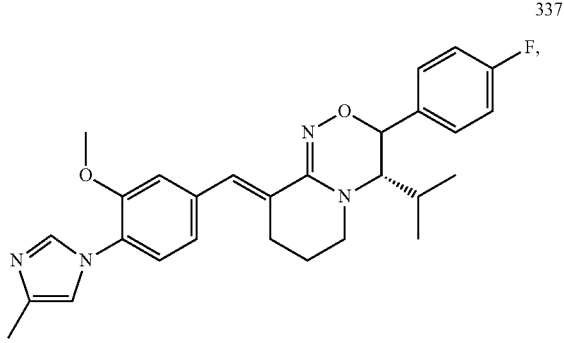
338
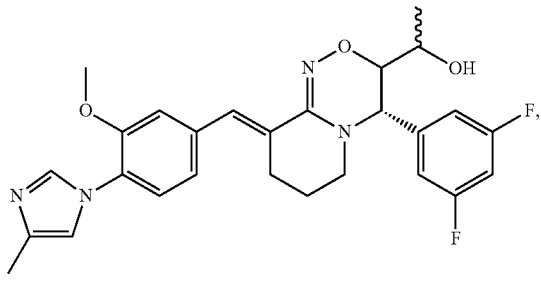

339
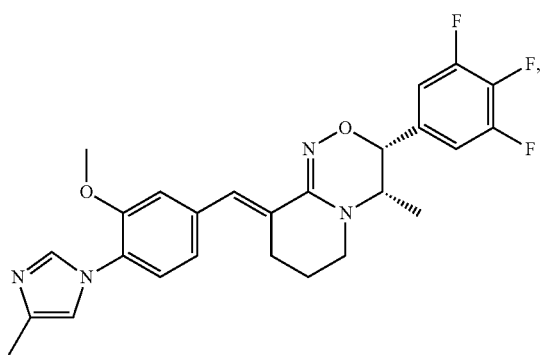
Racemic
340
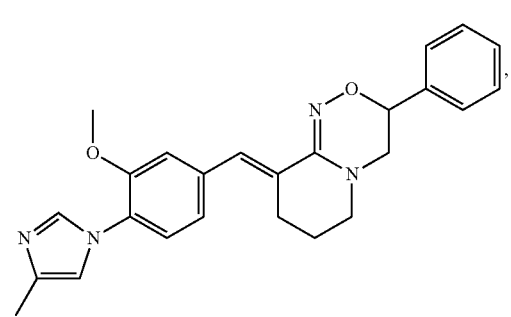
Racemic
341
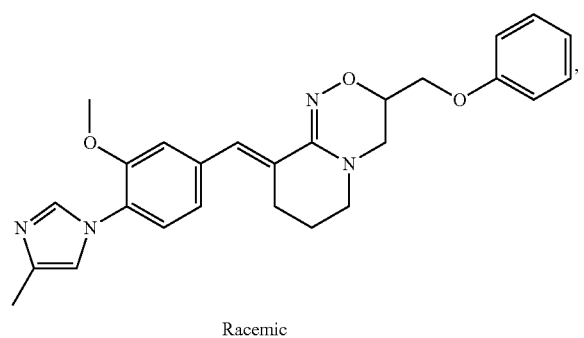
Racemic
342
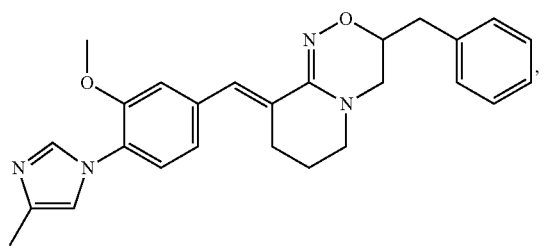
Racemic
343
344
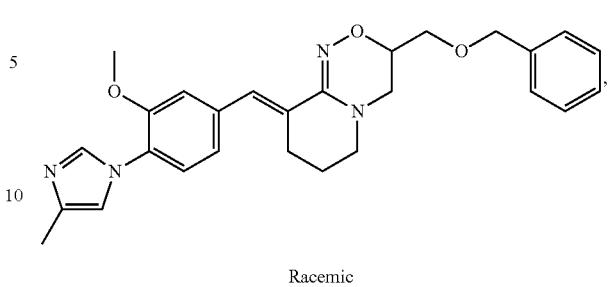
Racemic
345
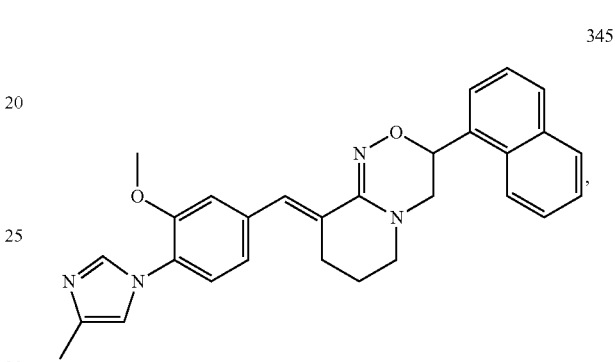
Racemic
346
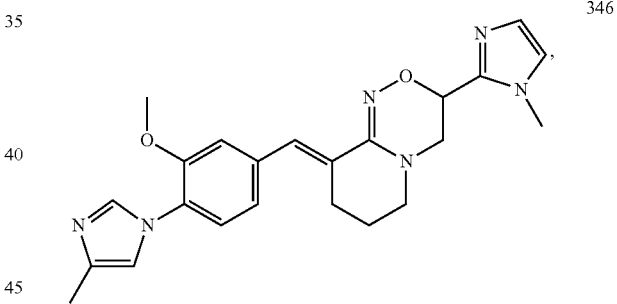
Racemic
347
Enantiomer I
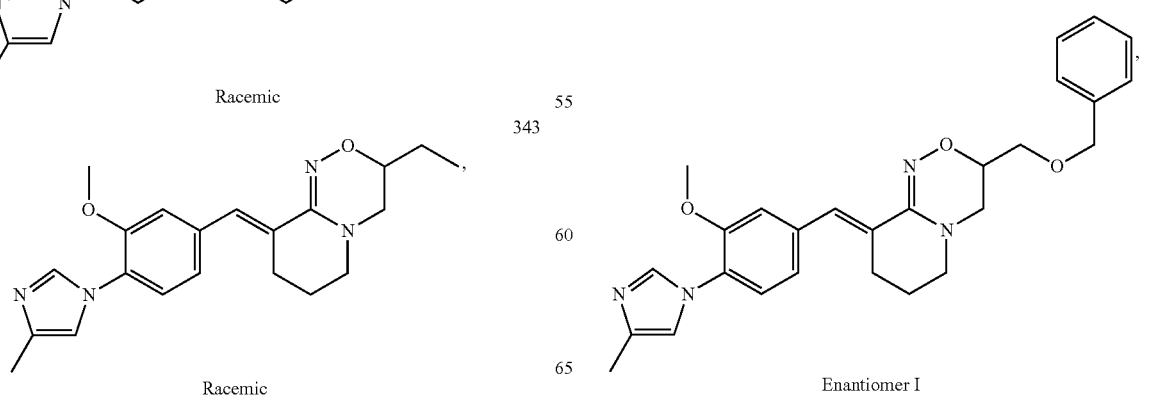

205
-continued
348
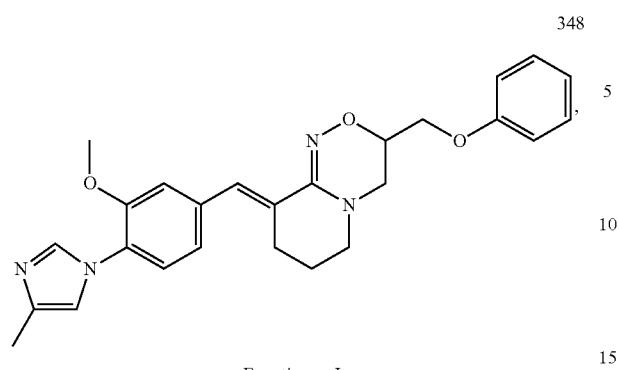
Enantiomer I
349
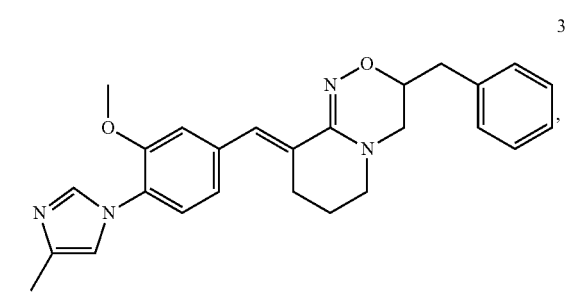
Enantiomer I
350
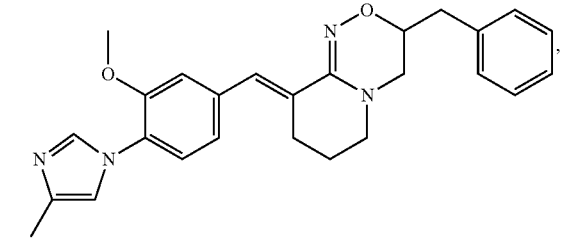
Enantiomer II
351
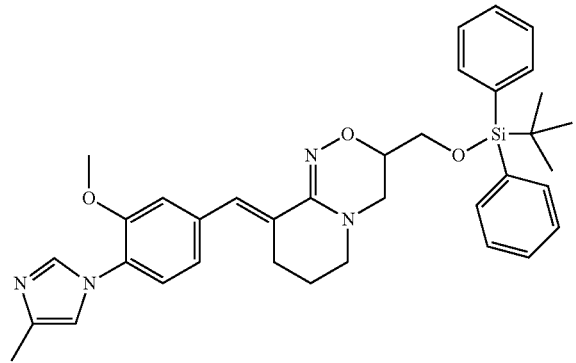
Enantiomer II
206
-continued
352
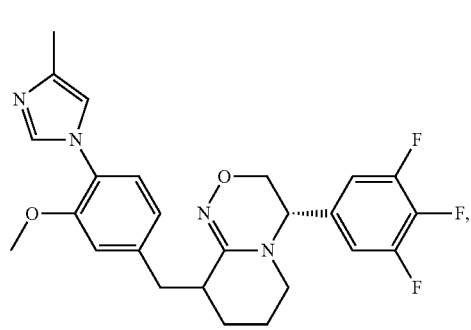
353
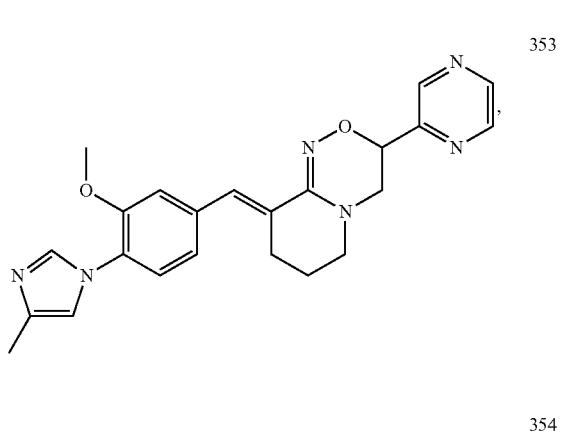
354
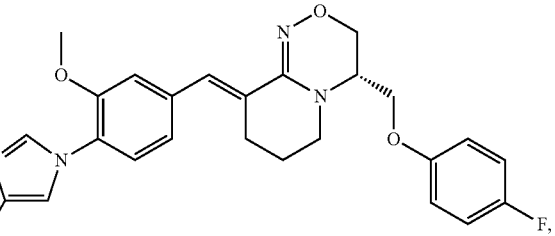
355
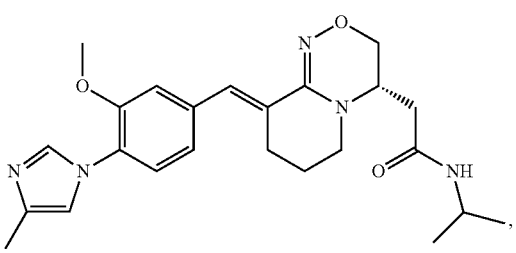
356
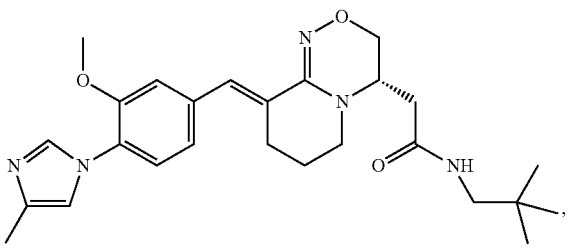

357
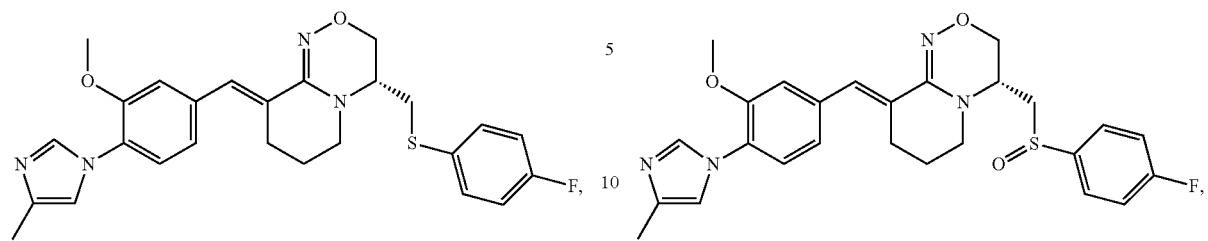
358
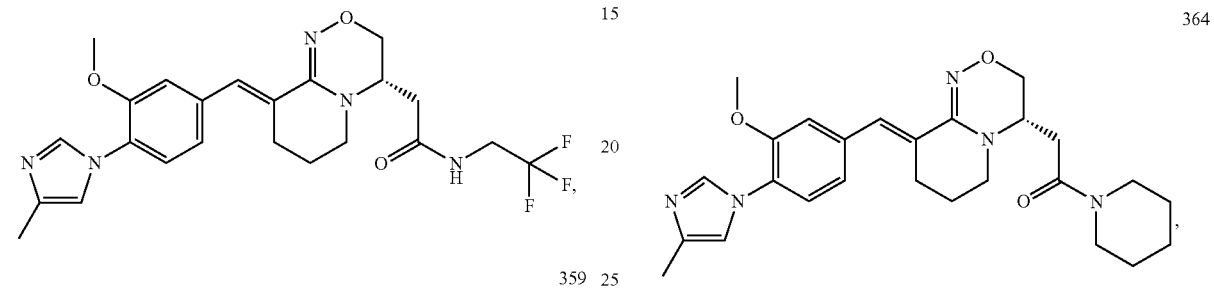
359
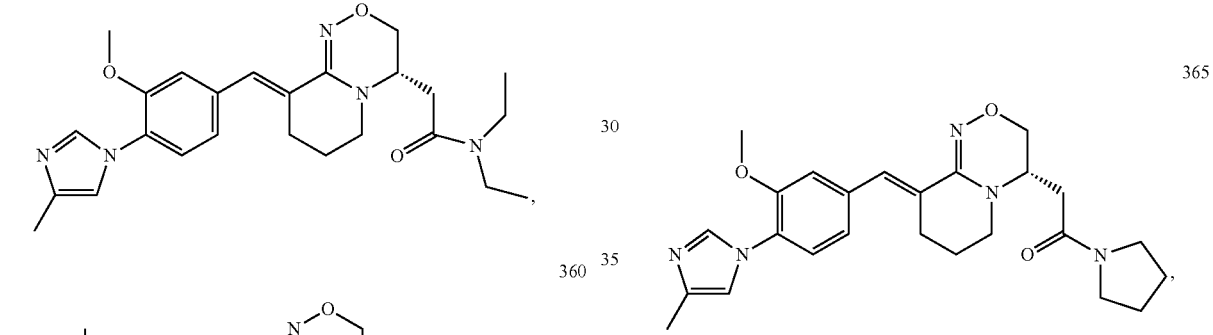
360
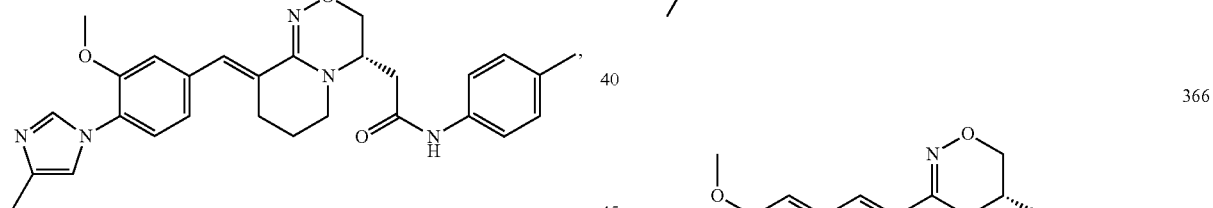
361
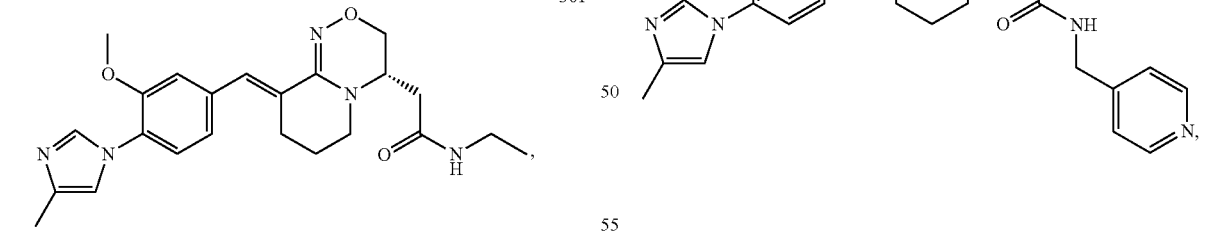
362
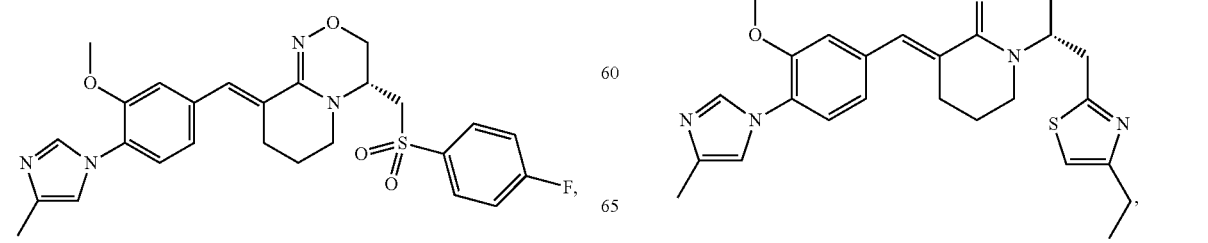
363
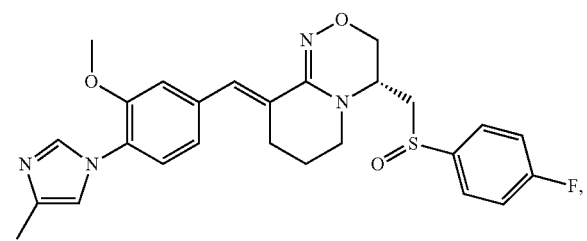
364
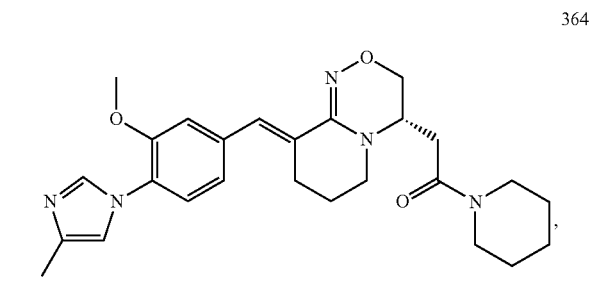
365
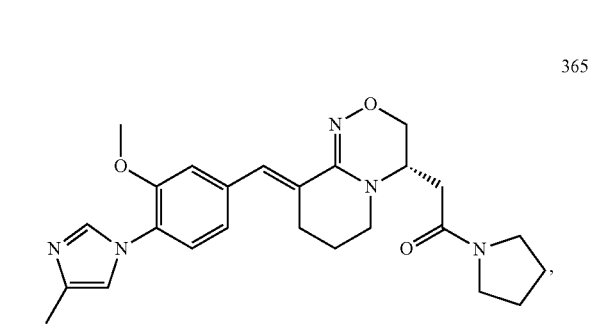
366
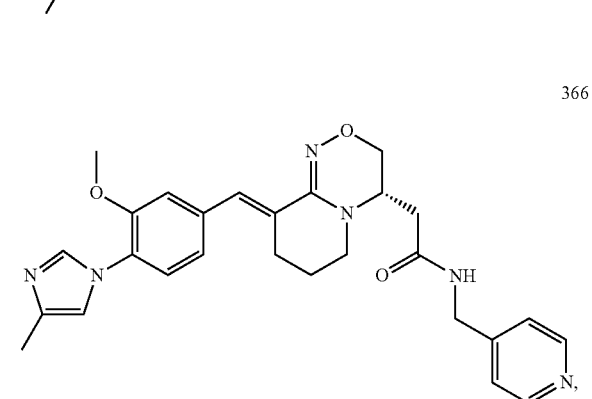
367
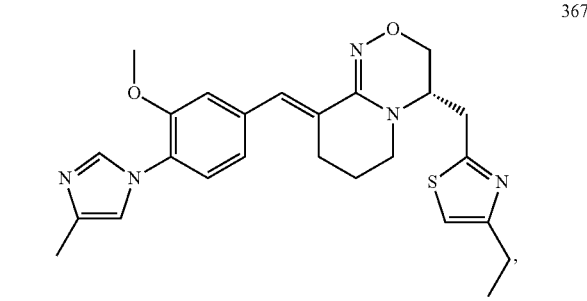

368
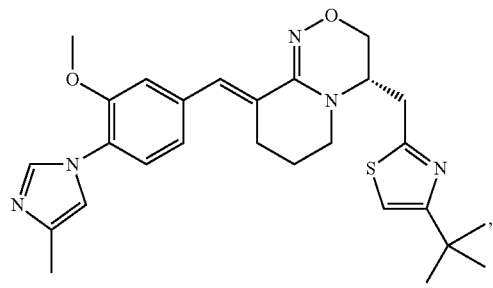
369
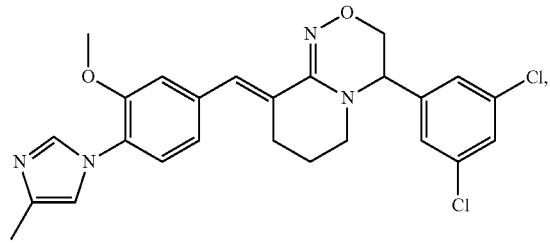
Racemic
370
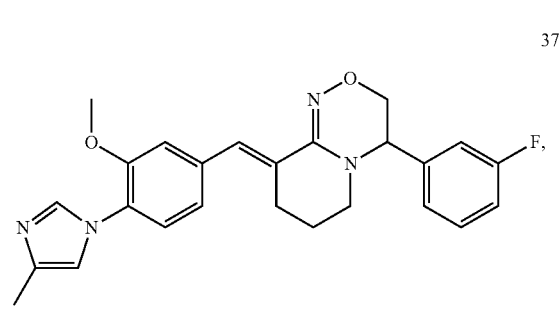
Racemic
371
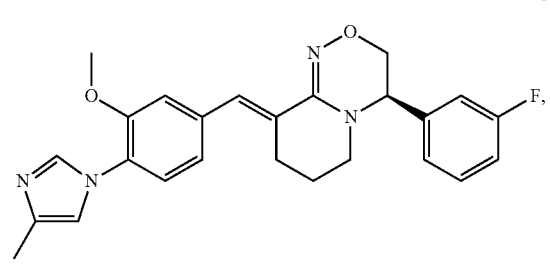
372
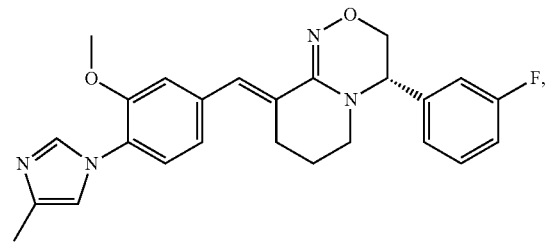
373
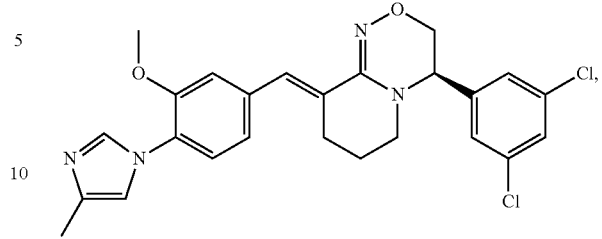
374
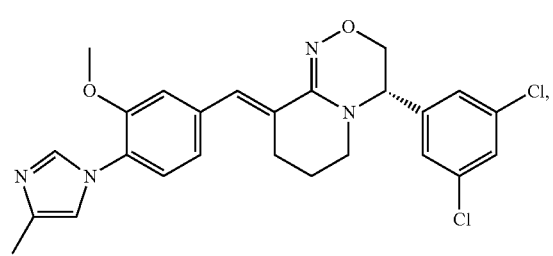
375
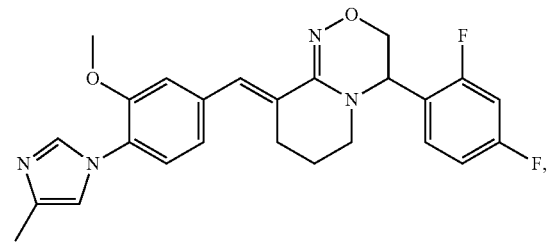
Racemic
376
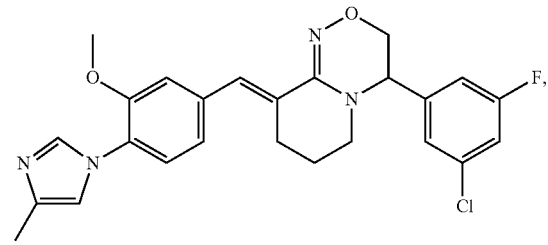
Racemic
377
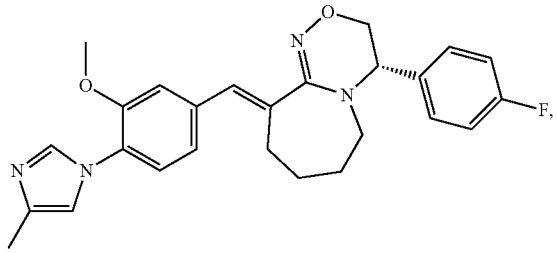

211
-continued
378
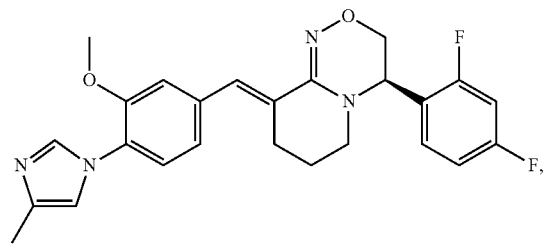
379
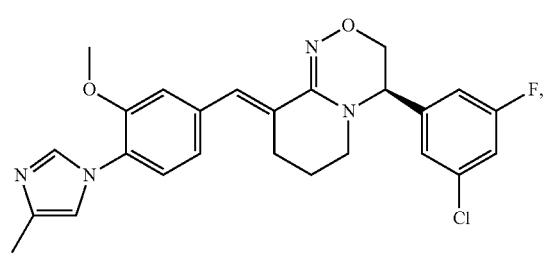
380
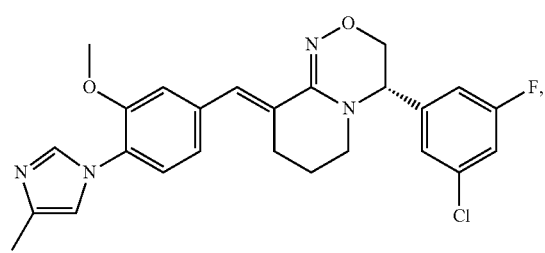
381
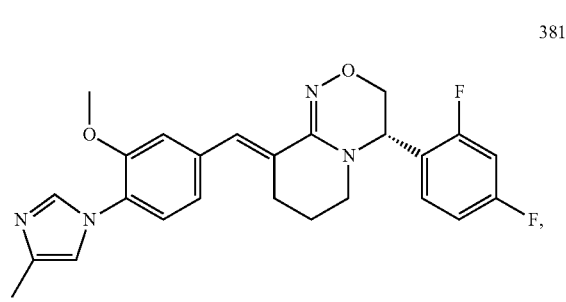
382
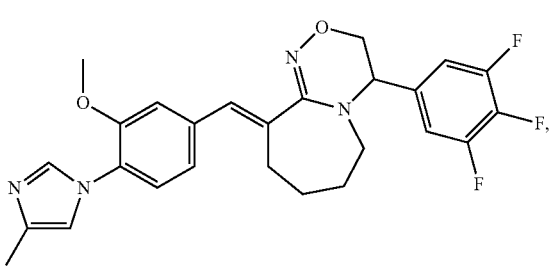
Racemic
212
-continued
383
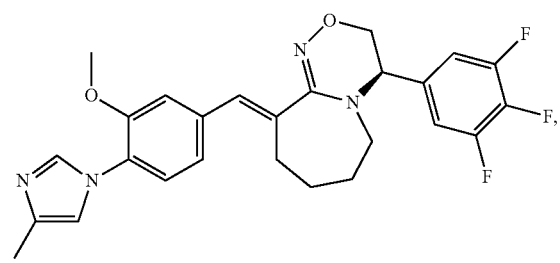
384
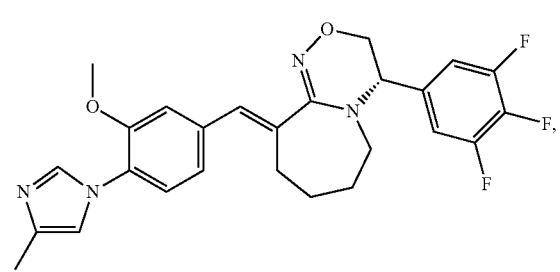
385
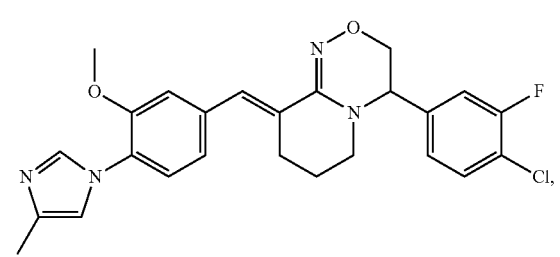
386
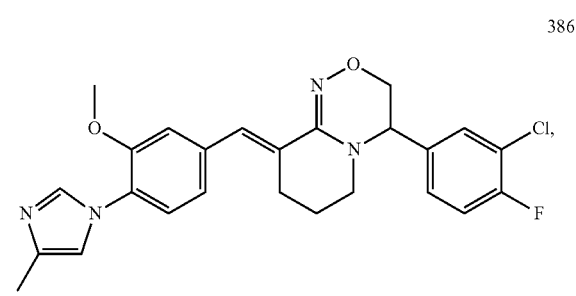
387
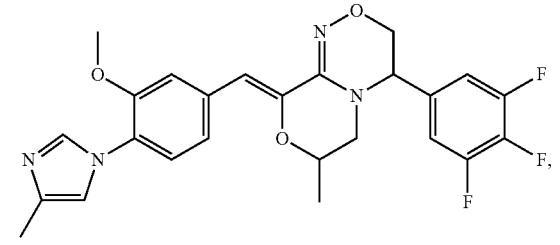
Diastereomer I

388

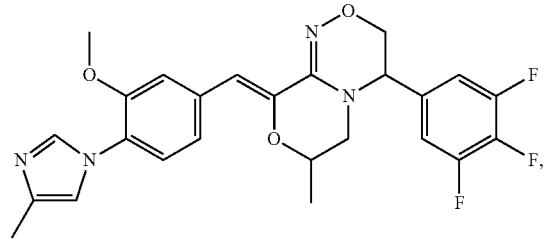

Diastereomer II

389

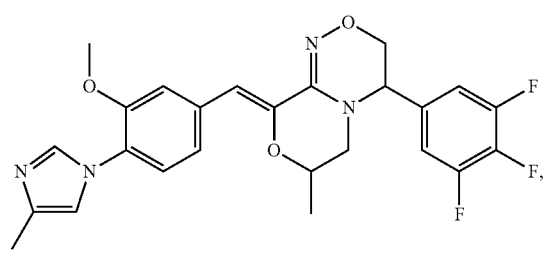

Diastereomer III

390

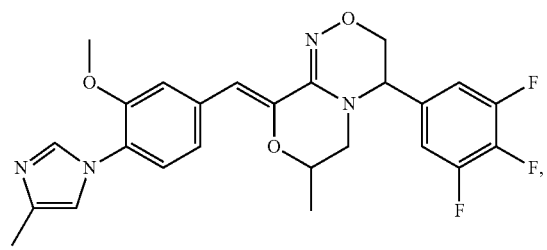

Diastereomer IV

391

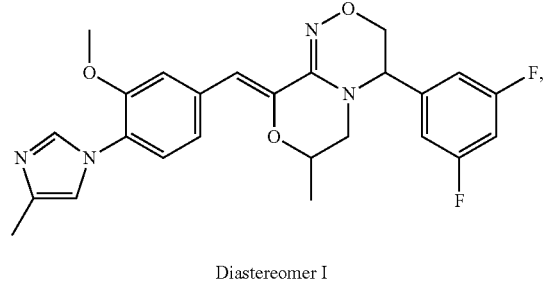

Diastereomer I

392

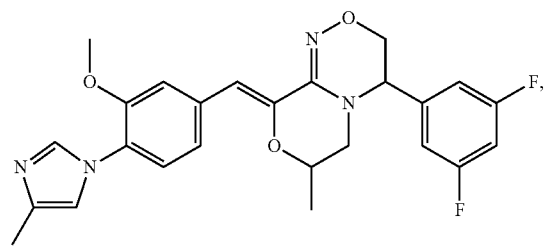

Diastereomer II

393

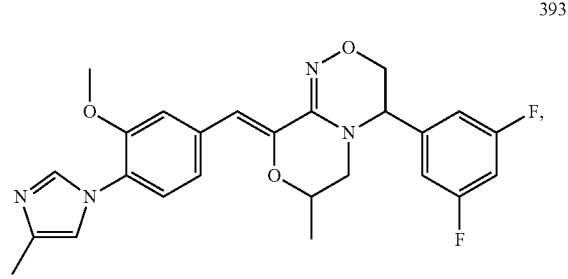

Diastereomer III

394

Diastereomer IV or a pharmaceutically acceptable salt thereof.

2. A pharmaceutical composition comprising a therapeutically effective amount of a compound of claim 1 or a pharmaceutically acceptable salt thereof, and a pharmaceutically acceptable carrier.

* * * * *